US008865707B2

(12) United States Patent
Ali et al.

(10) Patent No.: US 8,865,707 B2
(45) Date of Patent: Oct. 21, 2014

(54) CHOLESTERYL ESTER TRANSFER PROTEIN INHIBITORS

(75) Inventors: Amjad Ali, Freehold, NJ (US); Peter J. Sinclair, Scotch Plains, NJ (US); Gayle E. Taylor, Jersey City, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1480 days.

(21) Appl. No.: 12/087,189

(22) PCT Filed: Dec. 29, 2006

(86) PCT No.: PCT/US2006/049504
§ 371 (c)(1), (2), (4) Date: Jun. 26, 2008

(87) PCT Pub. No.: WO2007/081570
PCT Pub. Date: Jul. 19, 2007

(65) Prior Publication Data

US 2009/0018054 A1 Jan. 15, 2009

Related U.S. Application Data

(60) Provisional application No. 60/755,201, filed on Dec. 30, 2005.

(51) Int. Cl.

| | |
|---|---|
| ***C07D 265/10*** | (2006.01) |
| ***C07D 413/06*** | (2006.01) |
| ***A61K 31/5355*** | (2006.01) |
| ***A61K 31/535*** | (2006.01) |

(52) U.S. Cl.
USPC ............................. 514/228.8; 544/96; 544/97

(58) Field of Classification Search
USPC ................................... 544/96, 97; 514/228.8
See application file for complete search history.

(56) References Cited

U.S. PATENT DOCUMENTS

2006/0040999 A1 2/2006 Ali et al.

FOREIGN PATENT DOCUMENTS

WO WO 00 38725 7/2000

OTHER PUBLICATIONS

Havenaar, Matthias, Sci 336 Medicinal Chemistry Mar. 26, 2007. (retrieved from world wide web on Mar. 11, 2011).*

Brousseau et al. "Raising high-density lipoprotien cholesterol with inhibitors of cholesteryl ester transfer protein—a new approach to coronary artery disease". Expert Opin. Investig. Drugs. 2004. vol. 13, No. 10, pp. 1365-1368.

Clark, et al. "Description of the torcetrapib series of cholesteryl ester transfer protein inhibitors, including mechanism of action". J. Lipid Res. 2006, vol. 47, pp. 537-552.

* cited by examiner

*Primary Examiner* — Kahsay Habte
(74) *Attorney, Agent, or Firm* — James L. McGinnis; Catherine D. Fitch

(57) ABSTRACT

Compounds of Formula (I), including pharmaceutically acceptable salts of the compounds, are CETP inhibitors, and are useful for raising HDL-cholesterol, reducing LDL-cholesterol, and for treating or preventing atherosclerosis. In the compounds of Formula (I), $A^1$ is a cyclic group, and B is a cyclic group which is attached to the heterocyclic ring directly or through a methylene group.

(I)

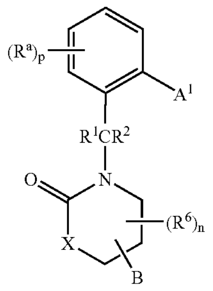

8 Claims, No Drawings

CHOLESTERYL ESTER TRANSFER PROTEIN INHIBITORS

CROSS REFERENCE TO RELATED APPLICATIONS

This application is a U.S. National Phase application under 35 U.S.C. §371 of PCT Application No. PCT/US2006/049504, filed Dec. 29, 2006, which claims priority under 35 U.S.C. §119(e) from U.S. Application No. 60/755,201, filed Dec. 30, 2005.

FIELD OF THE INVENTION

This invention relates to a class of chemical compounds that inhibit cholesterol ester transfer protein (CETP) and therefore may have utility in raising HDL-C, lowering HDL-C, and in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with an increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoBliprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from* 14*vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies or are in clinical trials. No CETP inhibitors are currently being marketed. Phase III clinical trials of torcetrapib were terminated due to an increase in mortality in patients using torcetrapib in a long-term outcomes trial. The mechanism that caused the increase in mortality is not currently known. New compounds are needed to ensure that CETP inhibitors are found that have the best profile of properties that relate to safety and effectiveness. The novel compounds described herein are very potent CETP inhibitors.

SUMMARY OF THE INVENTION

Compounds having Formula I, including pharmaceutically acceptable salts of the compounds, are CETP inhibitors, having the utilities described below:

I

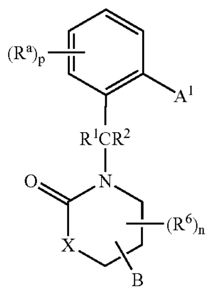

In the compounds of Formula I, the phenyl ring of Formula I may optionally have —N═ in place of —(CH)═ at one of the 4 positions that is not connected to the other parts of the structure of Formula I;

X is selected from —O—, —$(CR^7R^8)$—, and —$NR^5$;

B is —$\{C(R^3)(R^4)\}_q(A^2)$, and is substituted onto one of the —$(CH_2)$— groups of the heterocyclic ring of Figure I;

$A^1$ is selected from the group consisting of:

(a) an aromatic ring selected from phenyl and naphthyl;

(b) a phenyl ring to which is fused a 5-7 membered non-aromatic cycloalkyl ring, which optionally comprises 1-2 double bonds;

(c) a 5-6-membered heterocyclic ring having 1-4 heteroatoms independently selected from N, S, and O, and optionally also comprising 1-3 double bonds and a carbonyl group or —N(O)— group, wherein the point of attachment of $A^1$ to the carbon atom to which $A^1$ is attached is a carbon atom of $A^1$;

(d) a benzoheterocyclic ring comprising a phenyl ring fused to a 5-6-membered heterocyclic ring having 1-3 heteroatoms independently selected from O, N, and S, and optionally 1-2 double bonds, wherein the point of attachment of $A^1$ to the carbon atom to which $A^1$ is attached is a carbon atom of $A^1$; and (e) a —$C_3$-$C_8$ cycloalkyl ring optionally having 1-3 double bonds;

wherein $A^1$ is optionally substituted with 1-5 substituent groups independently selected from $R^b$;

$A^2$ is selected from the group consisting of:

(a) an aromatic ring selected from phenyl and naphthyl;

(b) a phenyl ring to which is fused a 5-7 membered non-aromatic cycloalkyl ring, which optionally comprises 1-2 double bonds;

(c) a 5-6-membered heterocyclic ring having 1-4 heteroatoms independently selected from N, S, and O, and optionally also comprising 1-3 double bonds and a carbonyl group or —N(O)— group, wherein the point of attachment of $A^2$ to the carbon atom to which $A^2$ is attached is a carbon atom of $A^2$;

(d) a benzoheterocyclic ring comprising a phenyl ring fused to a 5-6-membered heterocyclic ring having 1-3 heteroatoms independently selected from O, N, and S, and optionally 1-2 double bonds, wherein the point of attachment of $A^2$ to the carbon atom to which $A^2$ is attached is a carbon atom of $A^2$; and (e) a —$C_3$-$C_8$ cycloalkyl ring optionally having 1-3 double bonds;

wherein $A^2$ is optionally substituted with 1-5 substituent groups independently selected from $R^c$;

Each $R^a$ and $R^c$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)$SC_1$-$C_6$alkyl, —$NR^9R^{10}$, —C(=O)$NR^9R^{10}$, —$NR^9$C(=O)$OC_1$-$C_6$ alkyl, —$NR^9$C(=O)$NR^9R^{10}$, —$S(O)_xC_1$-$C_6$ alkyl, —$S(O)_yNR^9R^{10}$, —$NR^9S(O)_yNR^9R^{10}$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein when $R^a$ and $R^c$ are selected from the group consisting of a heterocyclic ring, —$C_3$-$C_8$ cycloalkyl, —$OC_3$-$C_8$ cycloalkyl, and —C(=O)$C_3$-$C_8$ cycloalkyl, the heterocyclic ring and —$C_3$-$C_8$ cycloalkyl groups of $R^a$ and $R^c$ are optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens and one group —OH, wherein when $R^a$ and $R^c$ are selected from the group consisting of —$C_1$-$C_6$ alkyl, —$C_2$-$C_6$ alkenyl, —$C_2$-$C_6$ alkynyl, —$OC_1$-$C_6$alkyl, —$OC_2$-$C_6$ alkenyl, —$OC_2$-$C_6$ alkynyl, —C(=O)$C_1$-$C_6$alkyl, —$CO_2C_1$-$C_6$alkyl, —C(=O)$SC_1$-$C_6$alkyl, —$NR^9$C(=O)$OC_1$-$C_6$alkyl, and —$S(O)_xC_1$-$C_6$ alkyl, the alkyl, alkenyl, and alkynyl groups of $R^a$ and $R^c$ are optionally substituted with 1-13 halogens and are optionally also substituted with 1-3 substituent groups independently selected from (a) —OH, (b) —CN, (c) —$NR^9R^{10}$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from —$OC_1$-$C_2$ alkyl, (f) —$OC_3$-$C_8$ cycloalkyl optionally having 1-3 double bonds and optionally substituted with 1-15 halogens, (g) —$CO_2$H, (h) —C(=O)$CH_3$, and (i) —$CO_2C_1$-$C_4$alkyl which is optionally substituted with 1-9 halogens;

wherein 2 groups $R^a$ that are on adjacent carbon atoms of the phenyl or optional pyridinyl ring of Formula I may optionally be joined to form a bridging moiety selected from —$CH_2CH_2CH_2$—, —$CH_2CH_2CH_2CH_2$—, and —CH=CH—CH=CH—, thereby yielding a cyclopentyl, cyclohexyl, or phenyl ring fused to the phenyl ring or optional pyridinyl ring of Formula I, wherein said cyclopentyl, cyclohexyl, or phenyl ring that is fused to the phenyl or optional pyridinyl ring of Formula I is optionally substituted with 1-2 groups independently selected from $R^a$, wherein said $R^a$ groups cannot be connected to form a ring, Each $R^b$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)$SC_1$-$C_6$alkyl, —$NR^9R^{10}$, —C(=O)$NR^9R^{10}$, —$NR^9$C(=O)$OC_1$-$C_6$ alkyl, —$NR^9$C(=O)$NR^9R^{10}$, —$S(O)_xC_1$-$C_6$ alkyl, —$S(O)_yNR^9R^{10}$, —$NR^9S(O)_yNR^9R^{10}$, halogen, —CN, —$NO_2$, phenyl, and a 5-6-membered heterocyclic ring having 1-4 heteroatoms independently selected from N, S, and O, said heterocyclic ring optionally also comprising a carbonyl group and optionally also comprising 1-3 double bonds, wherein when $R^b$ is selected from the group consisting of a heterocyclic ring, —$C_3$-$C_8$ cycloalkyl, —$OC_3$-$C_8$ cycloalkyl, and —C(=O)$C_3$-$C_8$ cycloalkyl, the heterocyclic ring and —$C_3$-$C_8$ cycloalkyl groups of $R^b$ are optionally substituted with 1-5 substituent groups independently selected from halogen, —$C_1$-$C_3$ alkyl, —$C_2$-$C_3$ alkenyl, —$NR^9R^{10}$, —$OC_1$-$C_3$ alkyl, —$CO_2$H, —CN, and —$CO_2C_1$-$C_3$alkyl, wherein —$C_1$-$C_3$ alkyl and —$C_2$-$C_3$ alkenyl in all uses are optionally substituted with 1-7 halogens and optionally one group —OH, wherein when $R^b$ is selected from the group consisting of —$C_1$-$C_6$ alkyl, —$C_2$-$C_6$ alkenyl, —$C_2$-$C_6$ alkynyl, —$OC_1$-$C_6$alkyl, —$OC_2$-$C_6$ alkenyl, —$OC_2$-$C_6$ alkynyl, —C(=O)$C_1$-$C_6$alkyl, —$CO_2C_1$-$C_6$alkyl, —C(=O)$SC_1$-$C_6$alkyl, —$NR^9$C(=O)$OC_1$-$C_6$alkyl, and —$S(O)_xC_1$-$C_6$ alkyl, the alkyl, alkenyl, and alkynyl groups of $R^b$ are optionally substituted with 1-13 halogens and are optionally also substituted with 1-3 substituent groups independently selected from (a) —OH, (b) —CN, (c) —$NR^9R^{10}$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from —$OC_1$-$C_2$ alkyl, (f) —$OC_3$-$C_8$ cycloalkyl optionally having 1-3 double bonds and optionally substituted with 1-15 halogens, (g) —$CO_2$H, (h) —C(=O)$CH_3$, and (i) —$CO_2C_1$-$C_4$alkyl which is optionally substituted with 1-9 halogens;

and wherein when $R^b$ is phenyl, said phenyl is optionally substituted with 1-5 halogens and is also optionally substituted with 1-3 substituents independently selected from —$C_1$-$C_4$ alkyl, —$C_2$-$C_4$ alkenyl, —$C_2$-$C_4$ alkynyl, —$C_3$-$C_6$ cycloalkyl, —$OC_1$-$C_4$alkyl, —$OC_2$-$C_4$ alkenyl, —$OC_2$-$C_4$ alkynyl, —$OC_3$-$C_6$ cycloalkyl, —C(═O)$C_1$-$C_4$alkyl, —C(═O)H, —$CO_2$H, —$CO_2C_1$-$C_4$alkyl, —$NR^9R^{10}$, —C(═O)$NR^9R^{10}$, —$NR^9$C(═O)$OC_1$-$C_4$ alkyl, —$NR^9$C(═O)$NR^9R^{10}$, —$S(O)_xC_1$-$C_4$ alkyl, —$S(O)_yNR^9R^{10}$, —$NR^9S(O)_yNR^9R^{10}$, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds and optionally comprising 1-3 substituents independently selected from halogen, —$CH_3$, —$OCH_3$, —$CF_3$, and —$OCF_3$; wherein when the substituents on phenyl when $R^b$ is phenyl are selected from —$C_1$-$C_4$ alkyl, —$C_2$-$C_4$ alkenyl, —$C_2$-$C_4$ alkynyl, —$C_3$-$C_6$ cycloalkyl, —$OC_1$-$C_4$alkyl, —$OC_2$-$C_4$ alkenyl, —$OC_2$-$C_4$ alkynyl, —$OC_3$-$C_6$ cycloalkyl, —C(═O)$C_1$-$C_4$alkyl, —$CO_2C_1$-$C_4$alkyl, —$NR^9$C(═O)$OC_1$-$C_4$ alkyl, and —$S(O)_x$ $C_1$-$C_4$ alkyl, then the alkyl, alkenyl, alkynyl, and cycloalkyl groups of said substituent groups optionally comprise 1-5 halogen substituents and also optionally comprise one substituent selected from —OH, —$NR^9R^{10}$, —$OCH_3$ optionally substituted with 1-3 F, and phenyl which is optionally substituted with 1-3 substituents independently selected from halogen, —$CH_3$, —$OCH_3$, —$CF_3$, and —$OCF_3$;

n is an integer from 0-4;

p is an integer from 0-4;

q is an integer selected from 0 and 1;

x is an integer selected from 0, 1, and 2;

y is an integer selected from 1 and 2;

$R^1$, $R^2$, $R^3$, and $R^4$ are each independently selected from the group consisting of H, halogen, —$C_1$-$C_4$ alkyl, —$C_3$-$C_6$ cycloalkyl, —$OC_1$-$C_4$ alkyl, and —$NR^9R^{10}$, wherein —$C_1$-$C_4$ alkyl, —$C_3$-$C_6$ cycloalkyl, and —$OC_1$-$C_4$ alkyl are each optionally substituted with 1-9 halogens and are each optionally also substituted with 1-2 groups independently selected from —OH, —C(═O)$CH_3$, —OC(═O)$CH_3$, $OC_1$-$C_2$ alkyl, and —$OC_1$-$C_2$ alkylene$OC_1$-$C_2$alkyl;

$R^5$ is selected from the group consisting of H and $C_1$-$C_5$ alkyl, wherein $C_1$-$C_5$ alkyl is optionally substituted with 1-11 halogens;

Each group $R^6$ is optionally substituted for an H atom on a —($CH_2$)— group of the heterocyclic ring in Figure I, wherein each $R^6$ is independently selected from the group consisting of H, —OH, halogen, —CN, —$NO_2$, —$OC_1$-$C_5$ alkyl, —$OC_2$-$C_5$ alkenyl, —$OC_2$-$C_5$ alkynyl, —$C_1$-$C_5$ alkyl, —$C_2$-$C_5$ alkenyl, and —$C_2$-$C_5$ alkynyl, wherein —$OC_1$-$C_5$ alkyl, —$OC_2$-$C_5$ alkenyl, —$OC_2$-$C_5$ alkynyl, —$C_1$-$C_5$ alkyl, —$C_2$-$C_5$ alkenyl, and —$C_2$-$C_5$ alkynyl are optionally substituted with 1-11 substituent groups independently selected from halogen;

$R^7$ and $R^8$ are each independently selected from the group consisting of H, halogen, —OH, and —$C_1$-$C_5$ alkyl, wherein —$C_1$-$C_5$ alkyl is optionally substituted with 1-11 substituent groups independently selected from halogen; and $R^9$ and $R^{10}$ are each independently selected from H, —$C_1$-$C_5$ alkyl, —C(═O)$C_1$-$C_5$ alkyl and —$S(O)_yC_1$-$C_5$ alkyl, wherein —$C_1$-$C_5$ alkyl in all instances is optionally substituted with 1-11 halogens.

DETAILED DESCRIPTION OF THE INVENTION

In embodiments of the compound of Formula I, including a pharmaceutically acceptable salts, the compound may have formula Ia, Ib, Ic, or Id, as shown below:

Ia

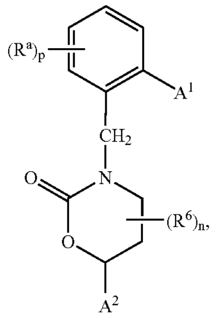

Ib

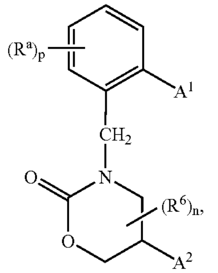

Ic

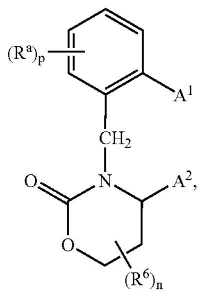

or

Id

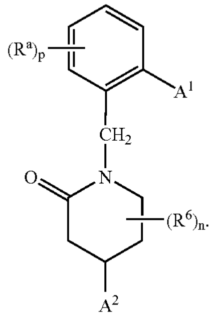

In further embodiments of the compound described by formula I, Ia, Ib, Ic or Ib, including pharmaceutically acceptable salts thereof, $A^1$ is phenyl, which is optionally substituted with 1-3 substituents independently selected from (a) halogen, (b) $C_{1-5}$alkyl optionally substituted with 1-5 halogens and optionally 1 group selected from phenyl, $C_{3-6}$cycloalkyl, and —OH, said phenyl and said $C_{3-6}$cycloalkyl optionally being substituted with 1-3 groups independently selected from halogen, $C_{1-3}$alkyl optionally substituted with 1-3 halogens, and —$OC_{1-3}$alkyl optionally substituted with 1-3 halogens, (c) —$OC_{1-3}$alkyl optionally substituted with 1-3 halogens, (d) $C_{2-4}$alkenyl optionally substituted with 1-3 halogens, and (e) optionally one group selected from phenyl and $C_{3-6}$cycloalkyl, said phenyl and cycloalkyl being optionally substituted with 1-3 substituents independently selected from halogen, —$CO_2$H, —$CO_2C_{1-3}$alkyl optionally substituted with 1-3 halogens, $C_{1-3}$alkyl optionally substituted with 1-3 halogens and optionally one —OH, and —$OC_{1-3}$alkyl optionally substituted with 1-3 halogens.

In embodiments of the compounds described above, including pharmaceutically acceptable salts thereof, each $R^a$ is independently selected from the group consisting of halogen, $C_{1-4}$alkyl optionally substituted with 1-3 halogens, $C_{2-3}$alkenyl optionally substituted with 1-3 halogens, —$OCH_3$, and $OCF_3$, wherein two $R^a$ groups on adjacent carbon atoms of the phenyl ring optionally may be joined to form a bridging moiety selected from —$CH_2CH_2CH_2$—, —$CH_2CH_2CH_2CH_2$—, and —CH═CH—CH═CH—, thereby yielding a cyclopentyl, cyclohexyl, or phenyl ring fused to the phenyl ring, said cyclopentyl, cyclohexyl, and phenyl ring being optionally substituted with 1-2 groups independently selected from halogen, $CH_3$, $CF_3$, —$OCH_3$, and —$OCF_3$.

In embodiments of the compounds described above, including pharmaceutically acceptable salts thereof, $R^6$ is $C_{1-3}$alkyl optionally substituted with 1-3 halogens; n is an integer from 0-2; B is $A^2$; and $A^2$ is phenyl optionally substituted with 1-3 groups independently selected from halogen, $C_{1-3}$alkyl optionally substituted with 1-3 halogens, —$OCH_3$ and —$OCF_3$.

In embodiments of the compounds described above, including pharmaceutically acceptable salts thereof, the phenyl ring of formula I, Ia, Ib, Ic, and Id cannot have —N═ in place of —CH═ at any of the 4 positions that is not connected to the rest of the structure.

In embodiments of the compounds described above, including pharmaceutically acceptable salts thereof, two groups Ra on adjacent carbon atoms of the phenyl ring cannot be connected to form a bridging moiety.

In embodiments of the compounds described above, including pharmaceutically acceptable salts thereof, $A^1$ is phenyl, which is optionally substituted with 1-3 substituents independently selected from (a) halogen, (b) $C_{1-5}$alkyl optionally substituted with 1-5 halogens and optionally 1 group selected from phenyl, $C_{3-6}$cycloalkyl, and —OH, said phenyl and said $C_{3-6}$cycloalkyl optionally being substituted with 1-3 groups independently selected from halogen, $C_{1-3}$alkyl optionally substituted with 1-3 halogens, and —$OC_{1-3}$alkyl optionally substituted with 1-3 halogens, (c) —$OC_{1-3}$alkyl optionally substituted with 1-3 halogens, (d) $C_2$-$C_4$alkenyl optionally substituted with 1-3 halogens, and (e) optionally one group selected from phenyl and $C_{3-6}$cycloalkyl, said phenyl and cycloalkyl being optionally substituted with 1-3 substituents independently selected from halogen, —$CO_2H$, —$CO_2C_{1-3}$alkyl optionally substituted with 1-3 halogens, $C_{1-3}$alkyl optionally substituted with 1-3 halogens and optionally one —OH, and —$OC_{1-3}$alkyl optionally substituted with 1-3 halogens;

$A^2$ is phenyl optionally substituted with 1-3 groups independently selected from halogen, $C_{1-3}$alkyl optionally substituted with 1-3 halogens, —$OCH_3$ and —$OCF_3$;

each $R^a$ is independently selected from the group consisting of halogen, $C_{1-4}$alkyl optionally substituted with 1-3 halogens, $C_{2-3}$alkenyl optionally substituted with 1-3 halogens, —$OCH_3$, and $OCF_3$, wherein two $R^a$ groups on adjacent carbon atoms of the phenyl ring optionally may be joined to form a bridging moiety selected from $CH_2CH_2CH_2$—, —$CH_2CH_2CH_2CH_2$—, and —CH═CH—CH═CH—, thereby yielding a cyclopentyl, cyclohexyl, or phenyl ring fused to the phenyl ring, said cyclopentyl, cyclohexyl, and phenyl ring being optionally substituted with 1-2 groups independently selected from halogen, $CH_3$, $CF_3$, —$OCH_3$, and $OCF_3$;

$R^6$ is $C_{1-3}$alkyl optionally substituted with 1-3 halogens;

p is an integer from 1-3; and n is an integer from 0-2.

In embodiments of the compounds described above, including pharmaceutically acceptable salts thereof, p is 1-3.

In embodiments of the compounds described above, including pharmaceutically acceptable salts thereof, n is 0-2.

In embodiments of the compounds described above, including pharmaceutically acceptable salts thereof, $R^6$ is $CH_3$.

In the compounds of Formula I, including subsets of the compounds, alkyl alkenyl, and alkynyl groups can be either linear or branched, unless otherwise stated.

DEFINITIONS

"Ac" is acetyl, which is $CH_3C(═O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkyl" may also be defined to have one or more double bonds, such as cyclohexenyl or cyclohexadienyl, but cannot have the number of double bonds that would make the cycloalkyl group aromatic.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocyclyl," "heterocycle," and "heterocyclic" means a fully or partially saturated or aromatic 5-6 membered ring containing 1-4 heteroatoms in the ring independently selected from N, S and O, unless otherwise stated. The heterocyclic ring may also be defined to include an optional carbonyl group or —N(O)-group as part of the ring structure. An example of the latter is pyridine N-oxide.

"Benzoheterocycle" represents a phenyl ring fused to a 5-6-membered heterocyclic ring having 1-2 heteroatoms, each of which is O, N, or S, where the heterocyclic ring may be saturated or unsaturated (i.e. the heterocyclic ring may have 1-2 double bonds in addition to the double bond of the phenyl ring). Examples include indole, 2,3-dihydroindole, benzofuran, 2,3-dihydrobenzofuran, quinoline, and isoquinoline. When the fused heterocycle is aromatic, the benzoheterocycle may also be referred to as benzoheteroaromatic or benzheteroaryl.

"Halogen" includes fluorine, chlorine, bromine and iodine. Halogen substitutents are most often fluorine or chlorine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to include all such isomeric forms of the compounds of Formula I and all mixtures of such isomeric forms. When structures are shown with a stereochemical representation, other stereochemical structures are also included individually and collectively, such as enantiomers, diastereoisomers (where diastereomers are possible), and mixtures of the enantiomers and/or diastereomers, including racemic mixtures.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the biphenyl and biaryl compounds herein may comprise mixtures of atropisomers (rotamers) in the NMR spectra. The individual atropisomers as well as mixtures thereof are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds of this invention are particularly effective in raising HDL-C and/or increasing the ratio of HDL-C to LDL-C. They are also effective in reducing LDL-C These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier without other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I and Ia-Ij) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) ricrosomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for use in improving a patient's lipid profile (i.e. raising HDL-C and lowering LDL-C) include one or both of statins and cholesterol absorption inhibitors. Particularly preferred are combinations of compounds of this invention with simvastatin, ezetimibe, or both simvastatin and ezetimibe. Also preferred are combinations of compounds of this invention with statins other than simvastatin, such as lovastatin, rosuvastatin, pravastatin, fluvastatin, atorvastatin, rivastatin, itavastatin, and ZD-4522.

Finally compounds of this invention can be used with compounds that are useful for treating other diseases, such as diabetes, hypertension and obesity, as well as other anti-atherosclerostic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these disease, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, including vildagliptin, sitagliptin, and saxagliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1; and (m) Non-sulfonylurea insulin secretagogues, such as the meglitinides (e.g. nateglinide and rapeglinide).

These other active ingredients that may be used in combination with the current invention also include antiobesity compounds, including 5-HT (serotonin) inhibitors, neuropeptide Y5 (NPY5) inhibitors, melanocortin 4 receptor (Mc4r) agonists, cannabinoid receptor 1 (CB-1) antagonists/inverse agonists, and $\beta_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as losartan; (2) angiotensin converting enzyme inhibitors (ACE inhibitors), such as enalapril and captopril; (3) calcium channel blockers such as nifedipine and diltiazam; and (4) endothelian antagonists.

Anti-obesity compounds may be administered in combination with the compounds of this invention, including: (1) growth hormone secretagogues and growth hormone secretagogue receptor agonists/antagonists, such as NN703, hexarelin, and MK-0677; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR11339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystolcinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, aminone, milrinone, cilostamide, rolipram, and cilomilast; (26) phosphodiesterase-3B' (PDE3B) inhibitors; (27) NE (norepinephrine) transport inhibitors, such as GW 320659, despiramine, talsupram, and nonmifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14]Bn(6-14) and [D-Phe6, Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

CETP Assay

An in vitro continuous assay for determining $IC_{50}$'s to identify compounds that are CETP inhibitors was performed based on a modification of the method described by Epps et al. employing BODIPY®-CE as the cholesteryl ester lipid donor. See Epps et al. (1995) *Method for measuring the activities of cholesteryl ester transfer protein* (*lipid transfer protein*), *Chem. Phys. Lipids.* 77, 51-63.

Particles used in the assay were created from the following sources: Synthetic donor HDL particles containing DOPC (Dioleoyl Phosphatidyl Choline), BODIPY®-CE (Molecular Probes C-3927), triolein (a triglyceride), and apoHDL were essentially created by probe sonication as described by Epps et al, but with the addition of a non-diffusable quencher molecule, dabcyl dicetylamide, in order to reduce background fluorescence. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat #7205). An assay cocktail containing CETP, 1×CETP buffer (50 mM Tris, pH 7.4, 100 mM NaCl, 1 mM EDTA), and half the final concentration of acceptor particles was prepared, and 100 μL of the assay cocktail was added to each well of the plate. Test compounds in DMSO were added in a volume of 3 μL. The plate was mixed on a plate shaker and then incubated at 25° C. for 1 hour. A second assay cocktail containing donor particles, the remaining acceptor particles and 1×CETP buffer was prepared. 47 μL of the second assay cocktail was added to the reaction wells to start the assay. Assays were performed at 25° C. in a final volume of 150 μL. Final concentrations of materials were: 5 ng/μL donor particles, 30 ng/μL acceptor particles (each expressed by protein content), 1×CETP buffer, 0.8 nM recombinant human CETP (expressed in CHO cells and partially purified), and up to 2% DMSO when testing compounds. The assay was followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well.

Data were evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate $IC_{50}$.

EXAMPLES

The following schemes and examples are provided so that the invention will be more fully appreciated and understood. Starting materials are made using known procedures or as shown below.

The examples should not be construed as limiting the invention in any way. The scope of the invention is defined only by the appended claims. Compounds of this invention have an $IC_{50}$ value as measured using the assay described above of less than or equal to 50 μM. Compounds preferably have an $IC_{50}$ in the range of 5 nM to 15 μM, more preferably in the range of 5 nM to 5 μM, even more preferably in the range of 5 nM to 200 nM, and even more preferably in the range of 5 nM to 100 nM.

Several methods for preparing the compounds in this invention are illustrated in the following Schemes and Examples. Starting materials are made from known procedures or as illustrated.

SCHEME 1

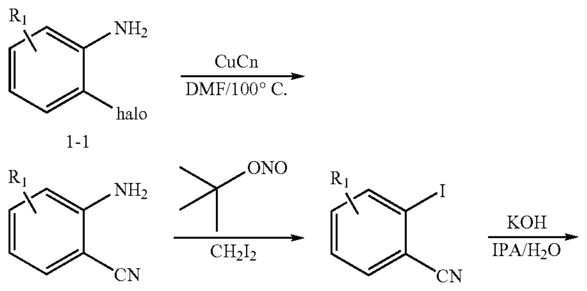

1-1

1-2

1-3

-continued

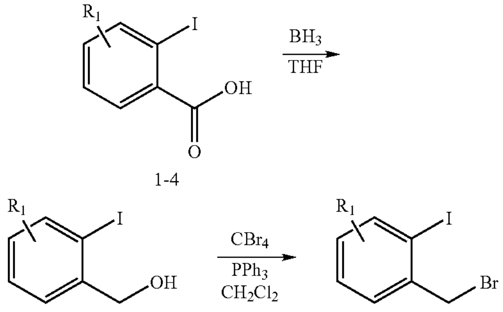

1-4

1-5

1-6

Intermediates 1-2, 1-3 and 1-4 utilized in the present invention can be purchased or prepared as shown in Scheme 1. An appropriately substituted 2-haloaniline 1-1 where the halogen is preferably iodo or bromo is treated with CuCN in DMF at elevated temperature to afford the corresponding 2-cyanoaniline 1-2. Alternatively, the nitrile can be prepared by treatment of 1-1 with KCN and CuI in the presence of a palladium (II) salt or in the presence of certain copper or nickel complexes (See: Smith, M. B. and March, J. "March's Advanced Organic Chemistry", 5th Ed., John Wiley and Sons, New York, pp. 867 (2001) and references therein). Iodides 1-3 are prepared by treatment of 1-2 with isoamylnitrite, n-pentylnitrite, t-butyl nitrite or the like in diiodomethane (see for example: Smith et al., *J. Org. Chem.* 55, 2543, (1990) and references cited therein). Alternatively, the iodide can be prepared first by diazonium formation using isoamylnitrite, n-pentylnitrite, t-butyl nitrite, sodium nitrite, nitrous acid or the like followed by heating in the presence of an iodide salt such as copper iodide, sodium iodide, potassium iodide, tetrabutylammonium iodide or the like. Hydrolysis of iodo-nitrile 1-3 is carried out using potassium hydroxide in isopropanol and water to afford the iodoacid 1-4. Further reduction with borane, lithium aluminum hydride, lithium borohydride or the like in ether, tetrahydrofuran, dimethoxyethane or the like affords the 2-iodo alcohols 1-5. Intermediates 1-5 can be transformed into benzyl bromides 1-6 using reagents such as triphenylphosphine and carbon tetrabromide in solvents such as dichloromethane or the like (see Smith, M. B. and March, J. "March's Advanced Organic Chemistry", 5th Ed., John Wiley and Sons, New York, pp. 518-199 (2001) and references therein).

SCHEME 2

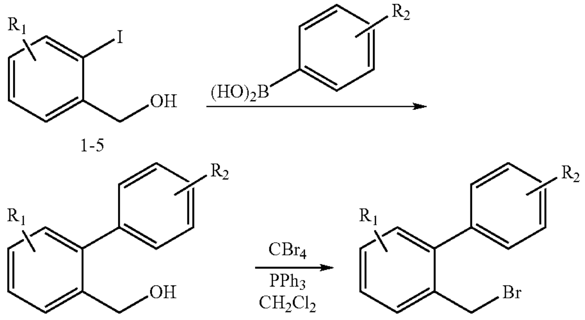

1-5

2-1

2-2

Intermediates 2-2 utilized in the present invention can be prepared as shown in Scheme 2. Benzyl alcohols 1-5 can be purchased or prepared according to the procedure outlined in Scheme 1. Intermediates 2-1 can be prepared via Suzuki reaction wherein 1-5 is coupled with an appropriately substituted aryl boronic acid or aryl boronate ester in the presence of a palladium catalyst. The coupling reaction may be carried out using Pd(n)acetate and potassium carbonate in aqueous acetone at reflux. Alternatively the reaction may employ tetrakis(triphenylphosphine)palladium in an ethanol/toluene mix in the presence of sodium carbonate. Alternatively, as practiced by those skilled in the art the reaction can employ a number of Palladium (0) compounds and Palladium (II) salts in a number of solvents and in the presence of a variety of ligands, bases, and promoters, generally but not exclusively, with heating and/or microwave irradiation. Some appropriate reaction conditions can be found described in Miyaua et al., *Chem. Rev.* 95, 2457 (1995) and references cited within and as described in Smith, M. B. and March, J. "March's Advanced Organic Chemistry", 5th Ed., John Wiley and Sons, New York, pp. 868-869 (2001) and references cited therein. Compounds 2-2 are prepared from intermediates 2-1 as described in Scheme 1.

SCHEME 3

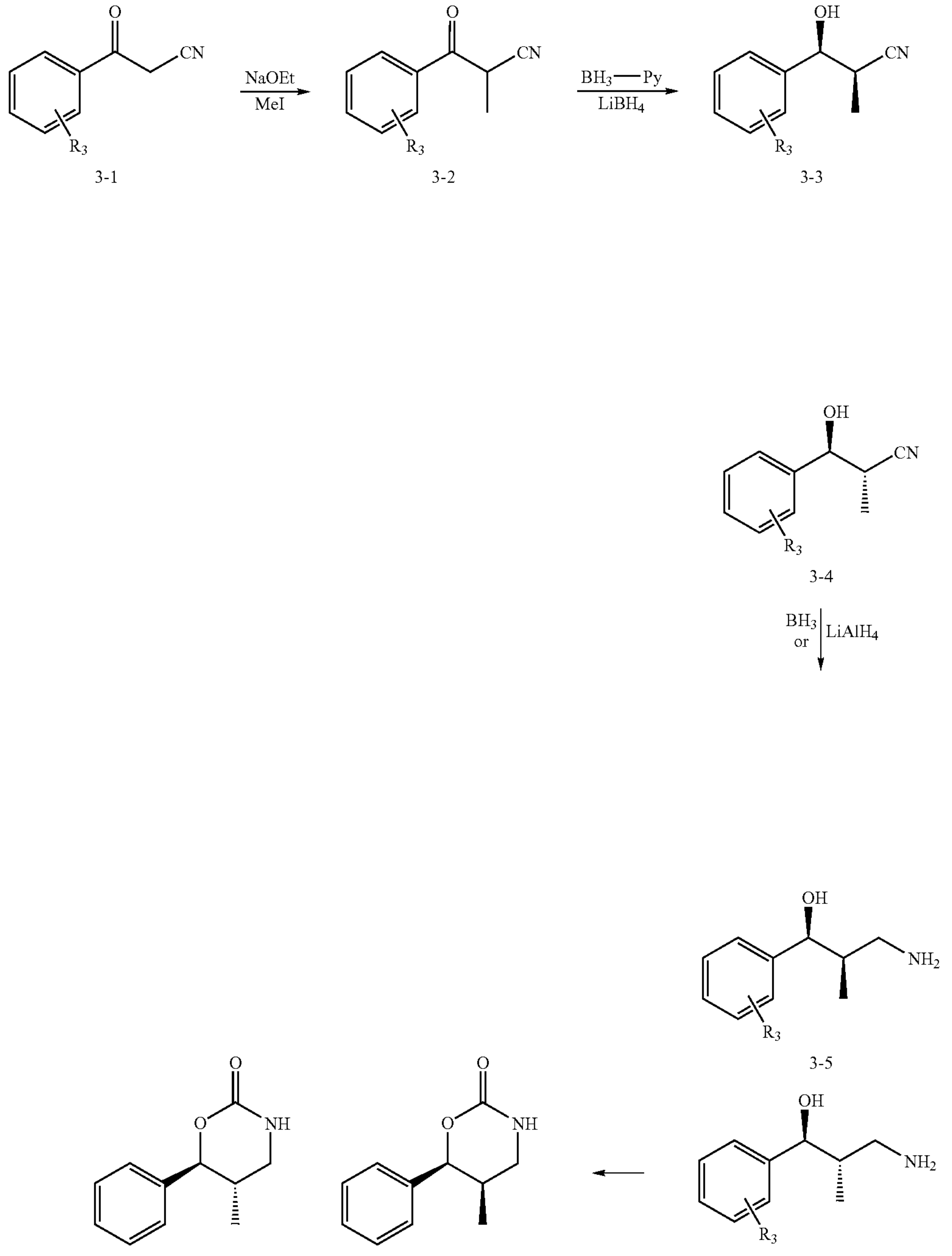

3-1 3-2 3-3 3-4 3-5 3-6 3-7 3-8

Compounds of the present invention can be prepared as shown in Scheme 3. Benzoyl acetonitrile derivatives 3-2 can be prepared by treatment of 3-1 with methyl iodide in the presence of a base such as sodium ethoxide in solvents such as ethanol, methanol or the like. Reduction of 3-2 can be carried out selectively by treatment with an appropriate reducing agent such as borane-pyridine complex or lithium borohydride in the presence of Lewis acids such as titanium tetrachloride, cerium chloride or the like or according to methods described in Smith, M. B. and March, J. "March's Advanced Organic Chemistry", 5th Ed., John Wiley and Sons, New York, pp. 1191-1203 (2001) and references cited therein. Further reduction of nitrites 3-3 and 3-4 can be carried out using reducing agents such as borane, lithium aluminum hydride or the like in solvents such as tetrahydrofuran and diethyl ether and the like. Amines 3-5 and 3-6 can be cyclized to the 1,3-oxazinan-2-ones with reagents such as 1,1-carbonyldiimidazole or triphosgene in the presence of triethylamine or the like in solvents such as tetrahydrofuran, benzene, methylene chloride or the like.

SCHEME 4

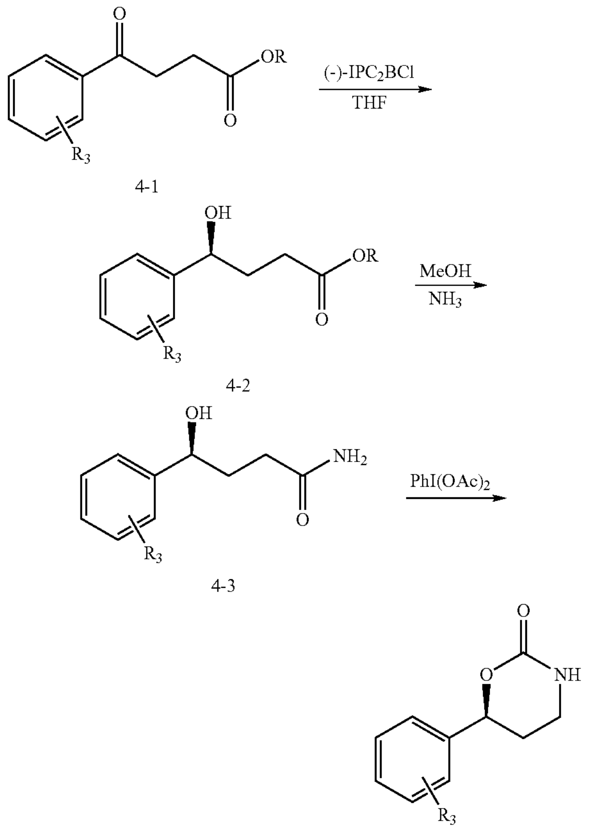

4-1

4-2

4-3

4-4

Compounds of the present invention can be prepared as shown in Scheme 4. Acetophenone derivatives 4-1 can be selectively reduced with chiral reducing agents such as (−)-chlorodiisopinecampheyl borane in solvents such as THF or the like or according to methods described in Smith, M. B. and March, J. "March's Advanced Organic Chemistry", 5th Ed., John Wiley and Sons, New York, pp. 510-511 (2001) Amides 4-3 can be cyclized to 1,3-oxazinan-2-ones by treatment with reagents such as iodophenyl diacetate or the like in solvents such as acetonitrile.

SCHEME 5

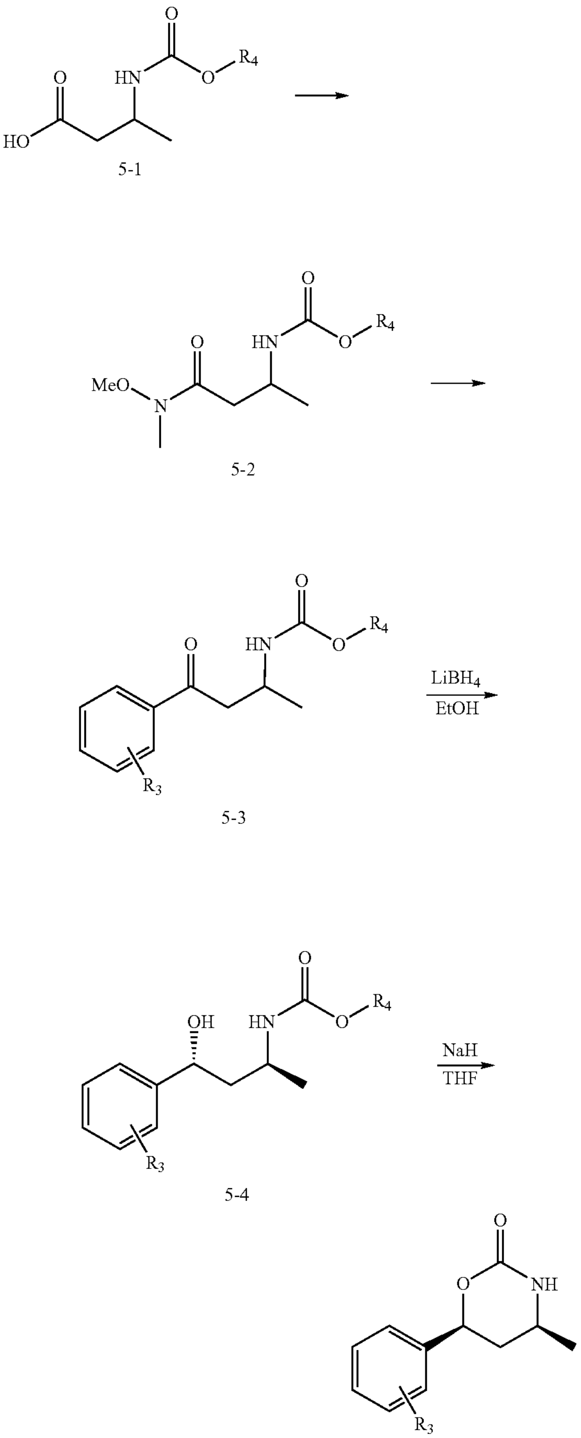

5-1

5-2

5-3

5-4

5-5

Compounds in the present invention can be prepared according to Scheme 5. 3-Amino butyric acid derivatives 5-1 can be converted to their corresponding Weinreb amides 5-2 under standard coupling conditions using reagents such as N—O-dimethyl hydroxylamine, isobutyl chloroformate, N-methyl morpholine in solvents such as methylene chlorideor the like or according to methods described in Smith, M. B.

and March, J. "March's Advanced Organic Chemistry", 5th Ed., John Wiley and Sons, New York, pp. 508-509 (2001) and references cited therein. Selective reduction of acetophenone derivatives 5-3 can be achieved by the use of reducing agents such as lithium borohydride or the like to afford alcohols 5-4 which can be cyclized to the corresponding 4-methyl-6-phenyl-1,3-oxazinan-2-ones by treatment with weak organic bases such as sodium hydride in the presence of solvents such as tetrahydrofuran or the like.

SCHEME 6

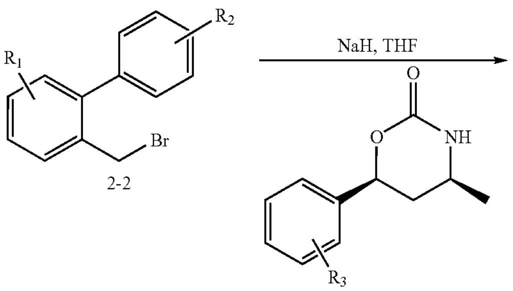

2-2

5-5

-continued

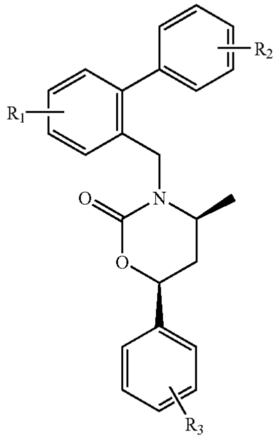

6-1

Compounds of the present invention can be prepared as shown in Scheme 6. 2-halobenzylbromides 2-2 wherein the halo is preferably iodo or bromo can be purchased or prepared as described in Schemes 1 and 2. Treatment of 2-2 with an appropriately substituted 1,3-oxazinan-2-ones such as 5-5 in the presence of a base such as sodium hydride or potassium tert-butoxide or the like in tetrahydrofuran, DMF or the like affords biaryl 1,3-oxazinan-2-ones.

SCHEME 7

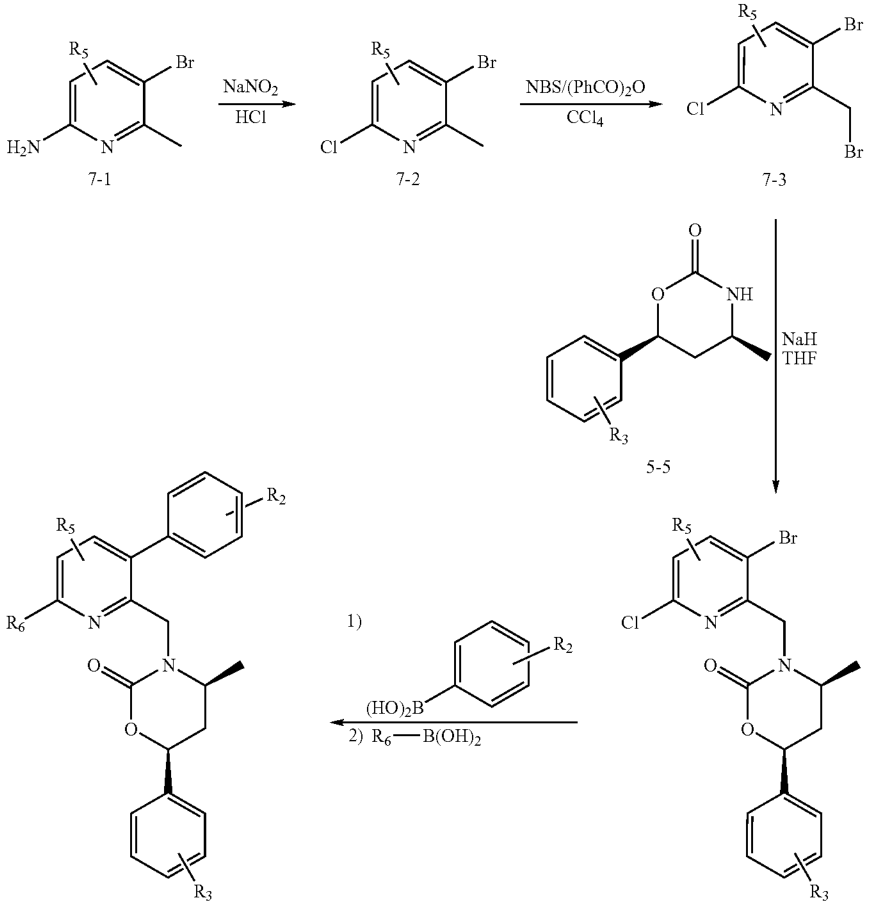

7-1

7-2

7-3

5-5

7-5

7-4

Heterocyclic biarylamines 7-5 can be prepared as shown in Scheme 7. An appropriately substituted amino pyridine 7-1 can be converted to the corresponding chloro pyridine 7-2 by diazonium formation using isoamylnitrite, n-pentylnitrite, t-butyl nitrite, sodium nitrite, nitrous acid or the like followed by treatment with concentrated HCl. Subsequent bromination of 7-2 is carried out using N-bromosuccinimide and benzoyl peroxide in solvents such as carbon tetrachloride and the like to afford the benzyl bromide 7-3. Other methods for benzylic halogenation can be found in Smith, M. B. and March, J. "March's Advanced Organic Chemistry", 5*th* Ed., John Wiley and Sons, New York, pp. 911 (2001) and references cited therein. Conversion to the heterocyclic 1,3-oxazinan-2-ones 7-4 can be carried out by treatment of 7-3 with appropriately substituted 1,3-oxazinan-2-ones such as 5-5 in the presence of a base such as sodium hydride or potassium tert-butoxide or the like in tetrahydrofuran, DMF or the like. Subsequent Suzuki reaction, as described previously in Scheme 2, affords 7-5.

INTERMEDIATE 1

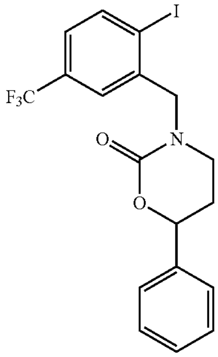

3-[2-iodo-5-(trifluoromethyl)benzyl]-6-phenyl-1,3-oxazinan-2-one

A stirred and cooled (0° C.) suspension of sodium hydride (60% suspension in mineral oil, 14 mg, 0.34 mmol) in THF (2 mL) was treated dropwise with a solution of 6-phenyl-1,3-oxazinan-2-one (24 mg, 0.137 mmol) in THF (2 mL), under an atmosphere of nitrogen. The reaction was stirred for 20 min at 0° C. and 2-(bromomethyl)-1-iodo-4-(trifluoromethyl)benzene (Intermediate 11; 50 mg, 0.137 mmol) was added. The reaction was allowed to warm to room temperature and stirred for an additional 3 h. Saturated $NH_4Cl$ (1 mL) was added and the resultant mixture was partitioned between $H_2O$ (20 mL) and EtOAC (20 mL). The aqueous layer was re-extracted with EtOAc (3×20 mL) and the combined extracts were washed with brine (40 mL), dried ($Na_2SO_4$), filtered and concentrated in vacuo to afford 3-[2-iodo-5-(trifluoromethyl)benzyl]-6-phenyl-1,3-oxazinan-2-one as a colorless oil. LCMS=462.0 $(M+1)^+$.

INTERMEDIATE 2

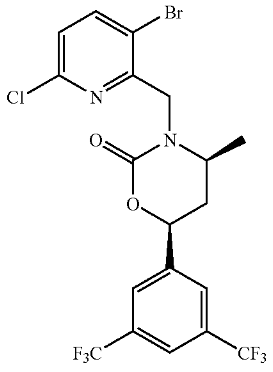

(4S,6S)-6-[3,5-bis(trifluoromethyl)phenyl]-3-[(3-bromo-6-chloropyridin-2-yl)methyl]-4-methyl-1,3-oxazinan-2-one To a stirred suspension of sodium hydride (60% in oil; 105 mg, 2.53 mmol) in THF (10 mL) at 0° C. under an atmosphere of $N_2$ was added a solution of (4S,6S)-6-[3,5-bis(trifluoromethyl)phenyl]-4-methyl-1,3-oxazinan-2-one (Intermediate 20; 68 mg, 0.21 mmol) in THF (2 mL) dropwise. The resultant mixture was stirred at 0° C. for 20 min prior to the addition of 3-bromo-2-bromomethyl-6-chloropyridine (59 mg, 0.21 mmol) as a solution in THF (1 mL). The reaction was allowed to warm to room temperature and stirred for 14 h. The reaction was quenched with $H_2O$ and was partitioned between $H_2O$ (25 mL) and EtOAC (35 mL). The aqueous layer was re-extracted with EtOAc (3×35 mL) and the combined extracts were washed with brine (25 mL), dried ($MgSO_4$), filtered and concentrated in vacuo. The residue was purified by flash silica gel chromatography (0-25% EtOAc/hexanes gradient) to afford (4S,6S)-6-[3,5-bis(trifluoromethyl)phenyl]-3-[(3-bromo-6-chloropyridin-2-yl)methyl]-4-methyl-1,3-oxazinan-2-one as a clear oil. LCMS=625.2 $(M+1)^+$. $^1H$ NMR ($CDCl_3$, 500 MHz): δ 7.94-7.90 (brs, 2H), 7.83 (s, 1H), 7.80 (d, J=8.2 Hz, 1H), 7.19 (d, J=8.2 Hz, 1H), 5.64 (m, 1H), 5.36 (d, J=17.6 Hz, 1H), 4.46 (d, J=17.6 Hz, 1H), 3.84 (m, 1H), 2.44 (m, 1H), 2.14 (m, 1H), 1.34 (d, J=6.2 Hz, 3H).

INTERMEDIATE 3

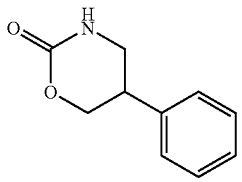

5-phenyl-1,3-oxazinan-2-one

Step A. 2-phenylpropane-1,3-diol

A cooled (0° C.) suspension of lithium aluminum hydride (1.61 g, 0.021 mol) in anhydrous ether (80 mL) was treated dropwise with diethyl malonate (5 g, 0.021 mol) under an atmosphere of nitrogen. The mixture was allowed to warm to room temperature, stirred for 10 h and refluxed for an additional 2 h. The reaction was quenched with 20% aqueous NaOH (5 mL), the inorganic substances removed by filtration and organic layer was separated, washed with brine (30 mL), dried ($MgSO_4$), filtered and concentrated. The title compound was obtained after flash column on silica gel using EtOAc:hexane 50:50 as the elute. $^1$H NMR ($CDCl_3$, 500 MHz) δ 7.41-7.21 (m, 5H), 4.05 (dd, J=7.5, 3.2 Hz, 2H), 3.97 (dd, J=5.8, 5.2 Hz, 1H), 3.12 (m, 1H).

Step B. 3-{[tert-butyl(dimethyl)silyl]oxy]-2-phenylpropanol-1-ol

A stirred and cooled (0° C.) suspension of sodium hydride (60% suspension in mineral oil, 290 mg, 7.24 mmol) in THF (5 mL) was treated dropwise with a solution of 2-phenylpropane-1,3-diol (1.10 g, 7.24 mmol) in THF (5 mL), under an atmosphere of nitrogen. The reaction was stirred for 20 min at 0° C. and a solution of tert-butyldimethyl silyl chloride in THF (10 mL) was added under ice-cooling. The reaction was allowed to warm to room temperature and stirred for an additional 18 h. Saturated $NH_4Cl$ (5 mL) was added and the resultant mixture was partitioned between $H_2O$ (80 mL) and EtOAC (120 mL). The aqueous layer was re-extracted with EtOAc (3×50 mL) and the combined extracts were washed with brine (100 mL), dried ($Na_2SO_4$), filtered and concentrated in vacuo. The crude product was purified by flash column chromatography using EtOAc:hexane=30:70 as the elute to afford 3-{[tert-butyl(dimethyl)silyl]oxy]-2-phenylpropanol-1-ol as a colorless oil. LCMS=267.3 $(M+)^+$.

Step C. 2-(3{[tert-butyl(dimethyl)silyl]oxy}-2-phenylpropyl)-1H-isoindole-1,3(2H)-dione A solution of diethyl azodicarboxylate (1.37 g, 7.87 mmol) in THF (5 mL) was added dropwise to an ice-cooled stirred solution of 3-{[tert-butyl(dimethyl)silyl]oxy]-2-phenylpropanol-1-ol (1.91 g, 7.15 mmol), phthalimide (1.16 g, 7.87 mmol) and triphenyl phosphine (2.06 g, 7.87 mmol) in THF (25 mL). The reaction was allowed to warm to room temperature and stirred for an additional 18 h. The solvent was removed in vacuo and the crude product was purified by flash column chromatography using EtOAc:hexane=30:70 as the elute to afford the title compound as a colorless oil. LCMS=396.3 $(M+1)^+$. $^1$H NMR ($CDCl_3$, 500 MHz): δ 7.80 (d, J=3.0 Hz, 1H), 7.79 (d, J=3.2 Hz, 1H), 7.69 (d, J=3.0 Hz, 1H), 7.67 (d, J=3.0 Hz, 1H), 7.28 s, 2H), 7.24 (s, 2H), 7.20 (m, 1H), 4." (m, 2H), 3.86 (m, 2H), 3.45 (m, 1H), 0.89 (s, 9H), −0.05 (s, 6H).

Step D. 3-amino-2-phenylpropan-1-ol

A cooled (0° C.) solution of 2-(3 {[tert-butyl(dimethyl) silyl]oxy}-2-phenylpropyl)-1H-isoindole-1,3(2H)-dione (0.900 g, 2.28 mmol) in EtOH (10 mL) was treated with hydrazine hydrate (1.41 mL, 3.42 mmol) and the resultant solution was allowed to warm to room temperature and stirred for 18 h. A solution of 5 N aqueous HCl in EtOH (25 mL) was added and the resulting biphasic mixture was stirred for 3 h. The mixture was treated with sat. $NaHCO_3$, until PH=9 attained and then extracted with EtOAC (3×60 ml). The combined organic extracts were washed with brine (50 mL), dried ($MgSO_4$), filtered and concentrated to afford the title compound as a white solid. LCMS=152.2 $(M+1)^+$.

Step E. 5-phenyl-1,3-oxazinan-2-one

A cooled (0° C.) solution of 3-amino-2-phenylpropan-1-ol (245 mg, 1.62 mmol) in $CH_2Cl_2$ (10 mL) was treated with diisopropylethylamine (1.65 mL, 9.72 mmol) and triphosgene (241 mg, 0.81 mmol), under an atmosphere of nitrogen. The reaction was stirred at 0° C. for an additional 2 h. The reaction was quenched with sat. $NaHCO_3$ (2 mL) and then extracted with EtOAc (3×40 mL). The combined organic extracts were washed with brine (30 mL), dried ($MgSO_4$), filtered and concentrated to afford the title compound as a colorless oil. LCMS=178.2 $(M+1)^+$.

INTERMEDIATE 4

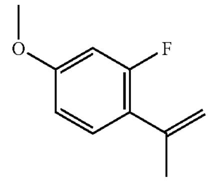

2-fluoro-1-isopropenyl-4-methoxybenzene

Step A: 2-(2-fluoro-4-methoxyphenyl)propan-2-ol

To a solution of 2-fluoro-4-methoxyacetophenone (4.45 g, 26.5 mmol) in THF (50 mL) at 0° C., a solution of 2.4 M MeMgBr (11.6 mL, 27.8 mmol) was added. The mixture was stirred at 0° C. and then room temperature for 4 h. The reaction was quenched with saturated ammonium chloride solution. The organic layer was extracted with ethyl acetate (3×50 mL). The combined ethyl acetate layers were washed with brine and dried over sodium sulfate. The title compound was obtained as an oil after flash column using EtOAc:hexane=2:8 as the elute.

Step B: 2-fluoro-1-isopropenyl-4-methoxybenzene

To a solution of 2-(2-fluoro-4-methoxyphenyl)propan-2-ol from Step A (3.89 g, 21.14 mmol) in methylene chloride (50 mL) at 0° C., MsCl (1.95 mL, 25.4 mmol) and triethylamine (6.52 mL, 46.5 mmol) were added. The solution was stirred at 0° C. and then room temperature for 2 h. The solution was diluted with methylene chloride (100 mL), washed with water, and dried over sodium sulfate. The title compound was obtained as an oil after flash column using EtOAc:hexane=1:9 as the elute. $^1$H NMR ($CDCl_3$, 500 MHz) δ 7.25 (t, J=9.0 Hz, 1H), 6.68 (dd, J=8.5, 2.5 Hz, 1H), 6.63 (dd, J=13, 2.5 Hz, 1H), 5.20 (d, J=17.0 Hz, 2H), 3.82 (s, 3H), 2.18 (s, 3H).

INTERMEDIATE 5

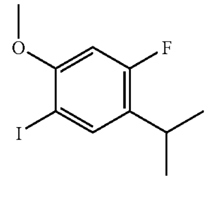

1-fluoro-4-iodo-2-isopropyl-5-methoxybenzene

A solution of the 2-fluoro-1-isopropenyl-4-methoxybenzene (Intermediate 4, 1.96 g, 11.81 mmol) in MeOH (30 mL) was charged with hydrogen at 1 atm and a catalytic amount of Pd/C. The mixture was stirred at room temperature for 1 h.

The mixture was filtered through Celite. The filtrate was then added to a mixture of silver sulfate (3.68 g, 11.81 mmol) and iodine (3.00 g, 11.81 mmol) in MeOH (10 mL). The mixture was stirred at room temperature for 3 h until the color of solution became light yellow. The mixture was filtered and the filtrate was concentrated. The title compound was obtained after flash column on silica gel using EtOAc:hexane 5:95 as the elute. $^1$H NMR ($CDCl_3$, 500 MHz) δ 7.61 (d, J=8.0 Hz, 1H), 6.56 (d, J=12.5 Hz, 1H), 3.90 (s, 3H), 3.18 (m, 1H), 1.28 (m, 6H).

INTERMEDIATE 6

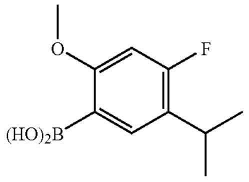

(4-fluoro-5-isopropyl-2-methoxyphenyl)boronic acid

To a solution of 1-fluoro-4-iodo-2-isopropyl-5-methoxybenzene (Intermediate 5, 2.61 g, 8.88 mmol) in THF at −78° C., n-BuLi (4.26 mL, 10.65 mmol, 2.5 M) was added dropwise. The solution was stirred at −78° C. for 30 min. Trimethyl borate (2.98 mL, 26.6 mmol) was added. The solution was then stirred at −78° C. for 3 h. The reaction was quenched at −78° C. with saturated ammonium chloride and the mixture was warmed to room temperature. The organic layer was extracted with ethyl acetate (3×50 mL). The combined ethyl acetate layers were washed with brine and dried over sodium sulfate. The title compound was obtained as a white solid. $^1$H NMR ($CDCl_3$, 500 MHz) δ 7.74 (d, J=10.0 Hz, 1H), 6.62 (d, J=12.5 Hz, 1H), 5.65 (br s, 2H), 3.92 (s, 3H), 3.20 (m, 1H), 1.22 (m, 6H).

INTERMEDIATE 7

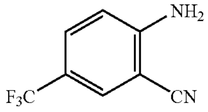

2-Amino-5-(trifluoromethyl)benzonitrile

A 2-liter flask was charged with 100 g (0.348 mol) of 4-amino-3-iodobenzotrifluoride, 40 g of CuCN and 750 mL of DMF. The mixture was heated to and then maintained at reflux for 1 hour. The reaction was cooled and poured into 3 L of water containing 300 mL of concentrated ammonium hydroxide. To the mixture was added 1 L $CH_2Cl_2$. The mixture was then filtered through Celite. The layers were separated and the aqueous layer was back extracted with $CH_2Cl_2$. The organic extracts were combined and the solvent removed under reduced pressure. The residue was dissolved in 1.5 L of ether and the resulting solution was washed with 1N ammonium hydroxide, aqueous sodium bisulfite, 1N aqueous HCl and brine. The solution was dried over anhydrous $MgSO_4$ and filtered through a silica gel plug containing a layer of $MgSO_4$ on top. The plug was washed with 0.5 L ether. The ether solutions were combined and concentrated to 750 mL and let stand at room temperature. After 2 days the resulting solids were collected, washed with hexanes and dried under reduced pressure to afford 2-amino-5-(trifluoromethyl)benzonitrile. $^1$H NMR ($CDCl_3$, 500 MHz) δ 7.68 (s, 1H), 7.58 (d, J=8.5 Hz, 1H), 6.81 (d, J=8.5 Hz, 1H), 4.80 (br s, 2H).

INTERMEDIATE 8

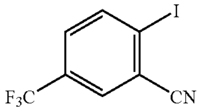

2-Iodo-5-(trifluoromethyl)benzonitrile

To a solution of 2-amino-5-(trifluoromethyl)benzonitrile (Intermediate 7, 15.1 g) and diiodomethane (24 mL) in acetonitrile (150 mL) at 35° C. was added t-butyl nitrite (21 mL) dropwise. The reaction was maintained at approximately 35° C. during the addition. The reaction was aged for 30 min and then heated to 60° C. for 30 minutes. The reaction mixture was cooled, diluted with ether and washed twice with water, twice with aqueous sodium bisulfite, water and then brine. The solution was dried over anhydrous $MgSO_4$, filtered through a silica gel plug and then concentrated giving afford a red oil. The product was purified by silica gel chromatography eluting sequentially with hexanes, 3:1 hexanes/$CH_2Cl_2$ and 1:1 hexanes/$CH_2Cl_2$ to afford 2-iodo-5-(trifluoromethyl) benzonitrile. $^1$H NMR ($CDCl_3$, 500 MHz) δ 8.10 (d, J=8.5 Hz, 1H), 7.85 (d, J=1.8 Hz, 1H), 7.52 (dd, J=8.5, 1.8 Hz, 1H).

INTERMEDIATE 9

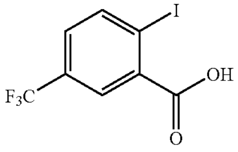

2-Iodo-5-(trifluoromethyl)benzoic acid

Potassium hydroxide (3.78 g; 0.0673 mol) was added to a stirred solution of 2-iodo-5-(trifluoromethyl)benzonitrile (Intermediate 8; 4 g; 0.0135 mol) in a 1:1 isopropanol:$H_2O$ solution (60 mL). The reaction was heated at reflux for 14 h and then partitioned between $H_2O$ (50 mL) and EtOAc (50 mL). The aqueous layer was extracted with EtOAc (50 mL) and acidified to pH 5 with 6N HCl. The aqueous layer was further extracted with EtOAc (4×50 mL) and the combined extracts were washed with brine (50 mL), dried over $MgSO_4$, filtered, and concentrated in vacuo to afford 2-iodo-5-(trifluoromethyl)benzoic acid as a yellow solid. LCMS=317.0 $(M+1)^+$. $^1$H NMR ($CDCl_3$, 500 MHz): δ 8.27 (d, J=1.6 Hz, 1H), 8.25 (d, J=8.2 Hz, 1H), 7.47 (dd, J=8.2, 1.8 Hz, 1H).

INTERMEDIATE 10

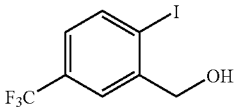

[2-Iodo-5-(trifluoromethyl)phenyl]methanol

Borane-THF (1.0M solution in THF; 94 mL; 94 mmol) was added to a stirred solution of 2-iodo-5-(trifluoromethyl)benzoic acid (Intermediate 9, 2.97 g; 9.4 mmol) in THF (300 mL) at 0° C. under $N_2$. The reaction was heated at reflux for 90 min and then carefully quenched with 6N HCl until no further gas evolution. The reaction was diluted with $H_2O$ (250 mL) and extracted with EtOAc (3×250 mL). The combined extracts were washed with brine (300 mL), dried over $MgSO_4$, filtered, and concentrated in vacuo. The crude material was purified by flash chromatography on silica gel (0-25% EtOAc/hexanes gradient) to afford [2-iodo-5-(trifluoromethyl)phenyl]methanol as a white solid. LCMS=285.0 $(M-17)^+$. $^1H$ NMR ($CDCl_3$, 500 MHz): δ 7.97 (d, J=8.3 Hz, 1H), 7.79 (s, 1H), 7.28 (d, J=8.4 Hz, 1H), 4.75 (s, 2H).

INTERMEDIATE 11

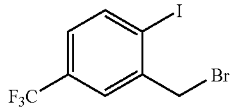

2-(Bromomethyl)-1-iodo-4-(trifluoromethyl)benzene

Carbon tetrabromide (1.86 g; 5.6 mmol) and triphenylphosphine (1.47 g; 5.6 mmol) were added successively to a stirred solution of [2-iodo-5-(trifluoromethyl)phenyl] methanol (Intermediate 10, 1.13 g; 3.74 mmol) in $CH_2Cl_2$ (25 mL) at 0° C. under $N_2$. The reaction was stirred at room temperature for 48 h. A second equivalent of carbon tetrabromide (1.2 g; 3.74 mmol) and triphenylphosphine (0.98 g; 3.74 mmol) was added and the reaction was stirred an additional 14 h. The solvent was removed in vacuo and the residue was purified by flash chromatography on silica gel (0-25% EtOAc/hexanes gradient) to afford 2-(bromomethyl)-1-iodo-4-(trifluoromethyl)benzene as a clear oil. $^1H$ NMR ($CDCl_3$, 500 MHz): δ 8.02 (d, J=8.2 Hz, 1H), 7.73 (d, J=1.8 Hz, 1H), 7.26 (dd, J=8.3, 1.8 Hz, 1H), 4.64 (s, 2H).

INTERMEDIATE 12

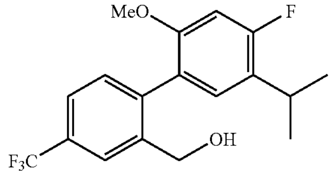

[4'-fluoro-5'-isopropyl-2'-methoxy-4-(trifluoromethyl)biphenyl-2-yl]methanol

A mixture of [2-iodo-5-(trifluoromethyl)phenyl]methanol (Intermediate 11, 3.09 g, 10.2 mmol), (4-fluoro-5-isopropyl-2-methoxyphenyl)boronic acid (Intermediate 6, 4.34 g, 20.5 mmol), $(Ph_3P)_4Pd$ (1.42 g, 1.23 mmol) and $Na_2CO_3$ (9.11 g, 85.9 mmol) in benzene/EtOH/$H_2O$ (7:1:3, 250 mL) was heated at reflux for 24 h under $N_2$. After cooling to room temperature, the aqueous phase was separated and extracted with $CH_2Cl_2$ (3×50 mL). The combined organic layers were dried ($Na_2SO_4$) and concentrated in vacuo to give the crude product. This was purified by flash chromatography on silica gel (65×200 mm, 0-20% EtOAc in hexanes gradient) to afford 4'-fluoro-5'-isopropyl-2'-methoxy-4-(trifluoromethyl)biphenyl-2-yl]methanol. $R_f$=0.50 (20% EtOAc in hexanes). $^1H$ NMR (500 MHz, $CDCl_3$) δ 7.86 (s, 1H), 7.59 (d, J=6.7 Hz, 1H), 7.30 (d, J=7.9 Hz, 1H), 6.99 (d, J=8.6 Hz, 1H), 6.68 (d, J=12.0 Hz, 1H), 4.52 (br s, 1H), 4.46 (br s, 1H), 3.73 (s, 3H), 3.25-3.17 (m, 1H), 1.82 (br s, 1H), 1.24 (d, J=6.8 Hz, 6H).

INTERMEDIATE 13

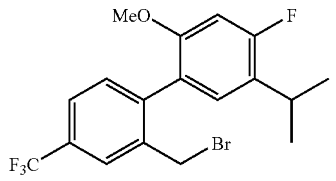

2'-(bromomethyl)-4-fluoro-5-isopropyl-2-methoxy-4'-trifluoromethyl)biphenyl

A solution of triphenylphosphine (3.11 g, 11.8 mmol) in dry $CH_2Cl_2$ (7 mL) was added by cannula to a stirred solution of carbon tetrabromide (3.93 g, 11.8 mmol) and 4'-fluoro-5'-isopropyl-2'-methoxy-4-(trifluoromethyl)biphenyl-2-yl] methanol (Intermediate 12, 3.38 g, 9.87 mmol) in dry $CH_2Cl_2$ (56 mL) at 0° C. under $N_2$. The reaction was allowed to warm to room temperature. After 2 h, the reaction mixture was concentrated in vacuo to give the crude product. This was purified by flash chromatography on silica gel (65×200 mm, 0-20% EtOAc in hexanes gradient) to afford 2'-(bromomethyl)-4-fluoro-5-isopropyl-2-methoxy-4'-(trifluoromethyl) biphenyl. $^1H$ NMR (500 MHz, $CDCl_3$) δ 7.83 (s, 1H), 7.61 (d, J=8.0 Hz, 1H), 7.35 (d, J=8.0 Hz, 1H), 7.15 (d, J=8.6 Hz, 1H), 6.72 (d, J=12.0 Hz, 1H), 4.43 (br d, J=10.0 Hz, 1H), 4.30 (br d, J=10.2 Hz, 1H), 3.76 (s, 3H), 3.30-3.22 (m, 1H), 1.29 (d, J=6.9 Hz, 6H).

INTERMEDIATE 14

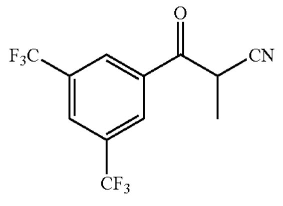

3-[3,5-bis(trifluoromethyl)phenyl]-2-methyl-3-oxo-propanenitrile

A solution of sodium ethoxide (0.127 g, 1.87 mmol) in EtOH (5 mL) was treated with 3,5-bis(trifluoromethyl)benzoyl acetonitrile (0.500 g, 1.78 mmol) portionwise over 5 min. The reaction was heated at reflux for 30 min before the addition of methyl iodide (0.41 mL, 6.6 mmol). Heating at reflux was continued for a further 2 h before the reaction mixture was allowed to cool and concentrated in vacuo. The residue was partitioned between $H_2O$ (10 mL) and EtOAC (20 mL) and the aqueous phase was separated and re-extracted with EtOAC (2×20 mL). The combined organic extracts were washed with brine (25 mL), dried (MgSO4), filtered and concentrated. The crude product was purified by flash chromatography on silica gel (0-20% EtOAc in hexanes gradient) to afford 3-[3,5-bis(trifluoromethyl)phenyl]-2-methyl-3-oxopropanenitrile. $^1H$ NMR (500 MHz, $CDCl_3$) δ 8.21 (s, 2H), 8.10 (s, 1H), 4.42 (q, J=7.1 Hz, 1H), 1.71 (d, J=7.1 Hz, 6H).

INTERMEDIATE 15

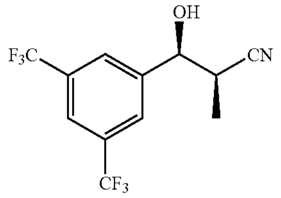

syn 3-[3,5-bis(trifluoromethyl)-phenyl]-3-hydroxy-2-methyl propanenitrile

A stirred and cooled (−30° C.) solution of 3-[3,5-bis(trifluoromethyl)phenyl]-2-methyl-3-oxopropanenitrile (intermediate 14, 309 mg, 1.05 mmol) was treated with $TiCl_4$ (1M solution in $CH_2Cl_2$, 1.58 mL, 1.58 mmol) and stirred for 1 h. The mixture was cooled to −78° C. and borane (8M complex with pyridine) dissolved in $CH_2Cl_2$ (210 uL) was added dropwise over 5 min. The mixture was allowed to stir for an additional 2 h, quenched with 1N HCl (2 mL) and allowed to warm to room temperature. The mixture was diluted with $H_2O$ (10 mL) and extracted with $CH_2Cl_2$ (3×30 mL). The combined organic extracts were washed with 1N HCl (3×15 mL), $H_2O$ (15 mL), brine (15 mL), dried over $MgSO_4$, filtered and concentrated. The crude product was purified by flash chromatography on silica gel (0-40% EtOAc in hexanes gradient) to afford syn 3-[3,5-bis(trifluoromethyl)phenyl]-3-hydroxy-2-methylpropanenitrile. LCMS=298.3 $(M-17)^+$. $^1H$ NMR ($CDCl_3$, 500 MHz): δ 7.91 (s, 3H), 4.95 (m, 1H), 3.11 (m, 1H), 2.74 (br d, J=4.1 Hz, 1H), 1.24 (d, J=5.9 Hz, 3H).

INTERMEDIATE 16

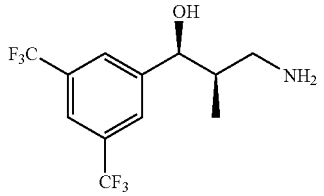

syn 3-amino-1-[3,5-bis(trifluoromethyl)phenyl]-2-methylpropan-ol

A solution of $BH_3$ in THF (1.0 M in THF, 1.08 mL, 1.08 mmol) was added dropwise to a cooled (0° C.) solution of syn 3-[3,5-bis(trifluoromethyl)phenyl]-3-hydroxy-2-methylpropanenitrile (intermediate 15, 140 mg, 0.47 mmol) in THF (2 mL). The solution was allowed to warm to room temperature and stirred for an additional 2 h. The reaction was quenched by the slow addition of 1N HCl (ca 2 mL) and then neutralized with sat. $NaHCO_3$. The mixture was extracted with EtOAc (3×20 mL) and the combined organic extracts were washed with brine (20 mL), dried over $MgSO_4$, filtered and concentrated to afford syn 3-amino-1-[3,5-bis(trifluoromethyl)phenyl]-2-methylpropan-1-ol. LCMS=302.1 $(M+1)^+$.

INTERMEDIATE 17

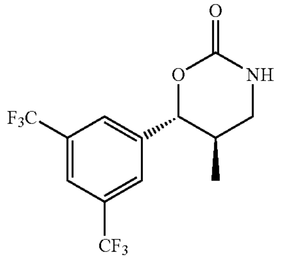

anti 6-[3,5-bis(trifluoromethyl)phenyl]-5-methyl-1,3-oxazinan-2-one

A solution of syn 3-amino-1-[3,5-bis(trifluoromethyl)phenyl]-2-methylpropan-1-ol (139 mg, 0.47 mmol) and 1',1'-carbonyldiimidazole (86 mg, 0.53 mmol) in 1:1 THF/$C_6H_6$ (6 mL) was stirred at room temperature for 16 h. The reaction was quenched with 1N HCl (2 mL) and then partitioned between $H_2O$ (15 mL) and $CH_2Cl_2$ (30 mL). The aqueous phase was separated and re-extracted with $CH_2Cl_2$ (2×30 mL). The combined organic extracts were washed with brine (15 mL), dried over $MgSO_4$, filtered and concentrated. The crude product was purified by flash chromatography on silica gel (0-30% EtOAc in hexanes gradient) to afford syn 6-[3,5-bis(trifluoromethyl)phenyl]-5-methyl-1,3-oxazinan-2-one. LCMS=328.3 $(M+1)^+$. $^1H$ NMR ($CDCl_3$, 500 MHz): δ 7.82 (s, 1H), 7.79 (s, 2H), 5.60 (s, 1H), 5.54 (br s, 1H), 3.83 (dd, J=4.8, 4.6 Hz, 1H), 3.28 (dq, J=5.2, 2.0 Hz, 1H), 2.45 (m, 1H), 0.94 (d, J=6.9 Hz, 3H).

INTERMEDIATE 18

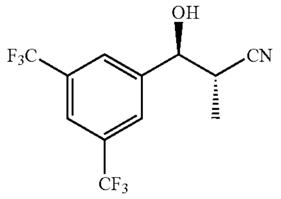

anti 3-[3,5-bis(trifluoromethyl)phenyl]-3-hydroxy-2-methylpropanenitrile

A stirred and cooled (−30° C.) solution of 3-{3,5-bis(trifluoromethyl)phenyl}-2-methyl-3-oxopropanenitrile (intermediate 14, 371 mg, 1.26 mmol) was treated with $CeCl_3$ (466 mg, 1.89 mmol) and stirred for 1 h. The mixture was cooled to −78° C. and $LiBH_4$ (2M solution in THF, 0.95 mL, 1.89 mmol) was added dropwise over 1 min. The mixture was allowed to stir for an additional 2 h, quenched with 1N HCl (2 mL) and allowed to warm to room temperature. The mixture was diluted with $H_2O$ (10 mL) and extracted with $CH_2Cl_2$ (3×30 mL). The combined organic extracts were washed with 1N HCl (3×15 mL), $H_2O$ (15 mL), brine (15 mL), dried over $MgSO_4$, filtered and concentrated. The crude product was purified by flash chromatography on silica gel (0-40% EtOAc in hexanes gradient) to afford anti 3-[3,5-bis(trifluoromethyl)phenyl]-3-hydroxy-2-methylpropanenitrile. LCMS=298.3 $(M+1)^+$. $^1H$ NMR ($CDCl_3$, 500 MHz): δ 7.85 (s, 3H), 4.95 (m, 1H), 3.04 (m, 1H), 2.81 (br d, J=4.1 Hz, 1H), 1.38 (d, J=7.1 Hz, 3H).

INTERMEDIATE 19

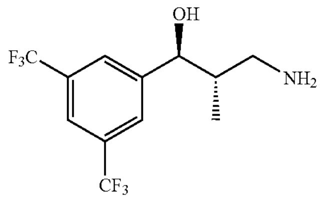

anti 3-amino-1-[3,5-bis(trifluoromethyl)phenyl]-2-methylpropan-1-ol

A solution of $BH_3$ in THF (1.0 M in THF, 1.32 mL, 1.32 mmol) was added dropwise to a cooled (0° C.) solution of anti 3-[3,5-bis(trifluoromethyl)phenyl]-3-hydroxy-2-methylpropanenitrile (intermediate 18, 170 mg, 0.57 mmol) in THF (2 mL). The solution was allowed to warm to room temperature and stirred for an additional 2 h. The reaction was quenched by the slow addition of 1N HCl (ca 2 mL) and then neutralized with sat. $NaHCO_3$. The mixture was extracted with EtOAc (3×20 mL) and the combined organic extracts were washed with brine (20 mL), dried over $MgSO_4$, filtered and concentrated to afford anti 3-amino-1-[3,5-bis(trifluoromethyl)phenyl]-2-methylpropan-1-ol. LCMS=302.3 $(M+1)^+$.

INTERMEDIATE 20

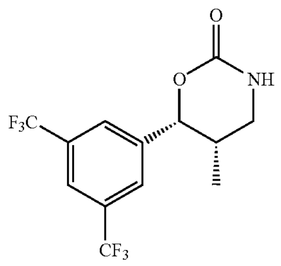

syn 6-[3,5-bis(trifluoromethyl)phenyl]-5-methyl-1,3-oxazinan-2-one

A solution of anti 3-amino-1-[3,5-bis(trifluoromethyl)phenyl]-2-methylpropan-1-ol (164 mg, 0.54 mmol) and 1',1'-carbonyldiimidazole (99 mg, 0.61 mmol) in 1:1 THF/$C_6H_6$ (6 mL) was stirred at room temperature for 16 h. The reaction was quenched with 1N HCl (2 mL) and then partitioned between $H_2O$ (15 mL) and $CH_2Cl_2$ (30 mL). The aqueous phase was separated and re-extracted with $CH_2Cl_2$ (2×30 mL). The combined organic extracts were washed with brine (15 mL), dried over $MgSO_4$, filtered and concentrated. The crude product was purified by flash chromatography on silica gel (0-30% EtOAc in hexanes gradient) to afford anti 6-[3,5-bis(trifluoromethyl)phenyl]-5-methyl-1,3-oxazinan-2-one. LCMS=328.3 $(M+1)^+$. $^1H$ NMR ($CDCl_3$, 500 MHz): δ 7.82 (s, 1H), 7.84 (s, 2H), 5.61 (br d, J=2.3 Hz, 1H), 5.41 (d, J=9.9 Hz, 1H), 3.54 (m, 1H), 3.26 (m, 1H), 2.24 (m, 1H), 0.94 (d, J=6.7 Hz, 3H).

INTERMEDIATE 21

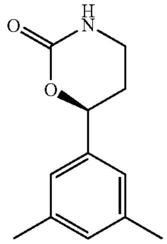

(6S)-6-(3,5-dimethylphenyl)-1,3-oxazinan-2-one

Step A: ethyl (4S)-4-(3,5-dimethylphenyl)-4-hydroxybutanoate

To a stirred solution of ethyl-4-(3,5-dimethylphenyl)-4-oxobutyrate (0.5 g; 2.14 mmol) in THF (5 mL) was added a solution of (−)-chlorodiisopinocampheylborane (1.71 g; 5.34 mmol) in THF (1 mL). The resultant solution stirred at room temperature for 4 days. The reaction was concentrated in vacuo and dried under high vacuo for 1 h. The residue was dissolved in ethyl acetate (10 mL) and diethanolamine (470 mL) was added. A white precipitate formed and the resultant mixture was stirred for 2 h, after which the solid was filtered off and washed with pentane. The filtrate was concentrated in vacuo and purified by flash silica gel chromatography (0-20% EtOAc/hexanes gradient) to afford ethyl (4S)-4-(3,5-dimethylphenyl)-4-hydroxybutanoate as a clear oil. LCMS=219.3 $(M+1-18)^+$. $^1H$ NMR ($CDCl_3$, 500 MHz): δ 6.99 (s, 2H), 6.95 (s, 1H), 4.72-4.69 (m, 1H), 4.16 (q, J=7.1 Hz, 2H), 2.45 (t, J=7.3 Hz, 2H), 2.34 (s, 6H), 2.11-2.06 (m, 2H), 1.29 (t, J=7.2 Hz, 3H).

Step B: (4S)-4-(3,5-dimethylphenyl)-4-hydroxybutanamide

A solution of ammonia in methanol (2.0M; 4.02 mL; 8.03 mmol) was treated with ethyl (4S)-4-(3,5-dimethylphenyl)-4-hydroxybutanoate (Step A; 474 mg; 2.01 mmol) and the resultant solution was stirred at 50° C. for 16 h. The reaction was concentrated in vacuo and the residue purified by flash silica gel chromatography (0-100% EtOAc/hexanes gradient) to afford (4S)-4-(3,5-dimethylphenyl)-4-hydroxybutanamide as a white solid. LCMS=190.3 $(M+1-18)^+$. $^1H$ NMR ($CDCl_3$, 500 MHz): δ 7.00 (s, 2H), 6.94 (s, 1H), 5.61 (br s, 1H), 5.40 (br s, 1H), 4.75 (dd, J=7.6, 2.8 Hz, 1H), 2.43-2.39 (m, 2H), 2.34 (s, 6H), 2.12-2.07 (m, 2H).

Step C: (6S)-6-(3,5-dimethylphenyl)-1,3-oxazinan-2-one

A stirred solution of (4S)-4-(3,5-dimethylphenyl)-4-hydroxybutanamide (Step B; 204 mg; 0.99 mmol) and iodobenzene diacetate (317 mg; 0.99 mmol) in acetonitrile (8 mL) was heated at 40° C. for 16 h. The reaction was concentrated in vacuo and the residue purified by flash silica gel chromatography (0-100% EtOAc/hexanes gradient) to afford (6S)-6-(3,5-dimethylphenyl)-1,3-oxazinan-2-one as a white solid. LCMS=206.3 $(M+1)^+$. $^1H$ NMR ($CDCl_3$, 500 MHz): δ 7.01 (s, 2H), 7.00 (s, 1H), 5.73 (s, 1H), 5.30 (dd, J=9.8, 2.8 Hz, 1H), 3.50 (dt, J=11, 4.8 Hz, 1H), 3.43-3.38 (m, 1H), 2.35 (s, 6H), 2.26-2.21 (m, 1H), 2.14-2.06 (m, 1H).

INTERMEDIATE 22

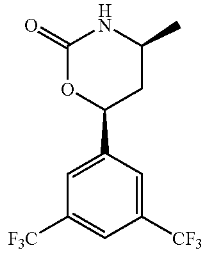

(4S,6S)-6-[3,5-bis(trifluoromethyl)phenyl]-4-methyl-1,3-oxazinan-2-one

Step A: 3-{[(benzyloxy)carbonyl]amino}-butanoic acid

To a stirred and cooled (0° C.) suspension of (+/−)-3-aminobutanoic acid (5 g; 48.5 mmol) in $H_2O$ (30 mL) was added NaOH pellets (3.88 g; 97 mmol) portionwise. The resultant mixture was stirred for 15 min to obtain a clear solution. Benzyl chloroformate (7.1 mL; 50 mmol) as a solution in acetone (30 mL) was added dropwise over 15 min. The reaction was allowed to warm to room temperature and stirred for 3.5 h. The reaction was washed twice with EtOAc (20 mL). The aqueous layer was separated and acidified to pH 2 with 6 N HCl. A precipitate formed and was collected by filtration, washed with $H_2O$ and dried in a vacuum oven to afford 3-{[(benzyloxy)carbonyl]amino}-butanoic acid as a white solid. LCMS=238.2 $(M+1)^+$. $^1H$ NMR ($CDCl_3$, 500 MHz): δ 7.34-7.30 (m, 5H), 5.18 (br s, 1H), 5.10 (s, 2H), 4.15-4.10 (m, 1H), 2.59 (s, 2H), 1.27 (d, J=6.9 Hz, 3H).

Step B: benzyl-{3-[methoxy(methyl)amino]-1-methyl-3-oxopropyl}carbamate

To a stirred solution of 3-{[(benzyloxy)carbonyl]amino}-butanoic acid (Step A; 9.0 g; 38 mmol) in $CH_2Cl_2$ (90 mL) at 0° C. under $N_2$ were added N-methylmorpholine (10.4 mL; 95 mmol) and isobutyl chloroformate (6.2 ml; 47.5 mmol). The resultant yellow solution was stirred at 0° C. for 5 min prior to portionwise addition of N,O-dimethylhydroxylamine hydrochloride (4.45 g; 45.6 mmol) over 5 min. The reaction was allowed to warm to room temperature and stirred for 14 h, then poured into 1 N HCl (200 mL) and extracted with $CH_2Cl_2$ (3×100 mL). The combined extracts were washed with 1 N HCl (100 mL), dried ($MgSO_4$), filtered and concentrated in vacuo. The residue was purified by flash silica gel chromatography (0-50% EtOAc/hexanes gradient) to afford benzyl-{3-[methoxy(methyl)amino]-1-methyl-3-oxopropyl}carbamate as a clear oil. LCMS=281.3 $(M+1)^+$. $^1H$ NMR ($CDCl_3$, 500 MHz): δ 7.35-7.29 (m, 5H), 5.61 (br s, 1H), 5.09 (s, 2H), 4.16-4.10 (m, 1H), 3.66 (s, 3H), 3.16 (s, 3H), 2.77-2.72 (m, 1H), 2.59-2.54 (m, 1H), 1.27 (d, J=6.6 Hz, 3H).

Step C: benzyl {3-[3,5-bis(trifluoromethyl)phenyl]-1-methyl-3-oxopropyl}carbamate To a stirred suspension of magnesium turnings (1.55 g; 63.76 mmol) in THF (50 mL) under an atmosphere of $N_2$ was added 1,2-dibromoethane (135 uL). The mixture was heated to 75° C. and 3,5-bis(trifluoromethyl)bromo benzene (4.59 mL; 26.79 mmol) was slowly added to maintain a gentle reflux. The reaction was heated at gentle reflux for 2.5 h and then cooled to room temperature. In a separate flask, isopropyl magnesium chloride (18 mL; 36 mmol) was added dropwise to a stirred solution of benzyl-{3-[methoxy(methyl)amino]-1-methyl-3-oxopropyl}carbamate (Step B; 5 g; 17.86 mmol) in THF (30 mL) at −20° C. The resultant solution was stirred at −20° C. for 40 min prior to dropwise addition of the Grignard solution. The reaction was allowed to warm to room temperature and stirred for 14 h. The reaction was quenched with 1 N HCl (100 mL) and extracted with EtOAc (3×100 mL). The combined extracts were washed with brine (100 mL), dried ($MgSO_4$), filtered and concentrated in vacuo. The residue was purified by flash silica gel chromatography (0-10% acetone/hexanes gradient) to afford benzyl {3-[3,5-bis(trifluoromethyl)phenyl]-1-methyl-3-oxopropyl}carbamate as a white solid. LCMS=434.2 $(M+1)^+$. $^1H$ NMR ($CDCl_3$, 500 MHz): δ 8.39 (s, 2H), 8.07 (s, 1H), 7.37-7.29 (m, 5H), 5.16-5.04 (m, 3 h), 4.31-4.23 (m, 1H), 4.16-4.10 (m, 1H), 3.19 (dd, J=16.8, 6.5 Hz, 1H), 1.34 (d, J=6.9 Hz, 3H).

Step D: benzyl {3-[3,5-bis(trifluoromethyl)phenyl]-3-hydroxy-1-methylpropyl}carbamate To a stirred solution of benzyl {3-[3,5-bis(trifluoromethyl)phenyl]-1-methyl-3-oxopropyl}carbamate (Step C; 1 g; 2.31 mmol) in anhydrous EtOH/THF (30 mL/15 mL) at −78° C. under an atmosphere of $N_2$ was added lithium borohydride (2.0 M in THF; 2.31 mL; 4.62 mmol) dropwise. The reaction was stirred at −78° C. for 1 h, then warmed to −30° C. over 1 h. The reaction was quenched at −30° C. with 1 N HCl (30 mL), warmed to room temperature, and partitioned between 1 N HCl (50 mL) and EtOAc (100 mL). The aqueous layer was re-extracted with EtOAc (3×50 mL) and the combined extracts were washed with brine (50 mL), dried ($MgSO_4$), filtered and concentrated in vacuo. The residue was purified by flash silica gel chromatography (0-25% EtOAc/hexanes gradient) to afford syn benzyl {3-[3,5-bis(trifluoromethyl)phenyl]-3-hydroxy-1-methylpropyl}carbamate and anti benzyl {3-[3,5-bis(trifluoromethyl)phenyl]-3-hydroxy-1-methylpropyl}carbamate in a 1:2.1 ratio as a white solid and a clear oil, respectively. Syn benzyl {3-[3,5-bis(trifluoromethyl)phenyl]-3-hydroxy-1-methylpropyl}carbamate: LCMS=436.2 $(M+1)^+$. $^1H$ NMR ($CDCl_3$, 500 MHz): δ 7.82 (s, 2H), 7.76 (s, 1H), 7.39-7.33 (m, 5H), 5.18-5.13 (m, 2H), 4.78-4.74 (m, 2H), 4.68 (br s, 1H), 4.17-4.11 (m, 1H), 1.82-1.75 (m, 1H), 1.64-1.58 (m, 1H), 1.26 (d, J=6.8 Hz, 3H). Anti benzyl {3-[3,5-bis(trifluoromethyl)phenyl]-3-hydroxy-1-methylpropyl}carbamate: LCMS=436.2 $(M+1)^+$. $^1H$ NMR ($CDCl_3$, 500 MHz): δ 7.84 (s, 2H), 7.78 (s, 1H), 7.38-7.31 (m, 5H), 5.13-5.04 (m, 2H), 4.94-4.91 (m, 1H), 4.81 (br s, 1H), 3.96-3.90 (m, 1H), 3.41 (br s, 1H), 1.99-1.93 (m, 1H), 1.87-1.82 (m, 1H), 1.26 (d, J=6.2 Hz, 3H).

Step E: syn 6-[3,5-bis(trifluoromethyl)phenyl]-4-methyl-1,3-oxazinan-2-one

To a stirred suspension of sodium hydride (24 mg; 0.61 mmol) in THF (4 mL), at 0° C. under an atmosphere of $N_2$ was added a solution of anti benzyl {3-[3,5-bis(trifluoromethyl)phenyl]-3-hydroxy-1-methylpropyl}carbamate (Step D; 177 mg; 0.41 mmol) in THF (6 mL) dropwise over 5 min. The reaction stirred at room temperature for 14 h. The reaction was quenched with 1 N HCl and partitioned between EtOAc (50 mL) and $H_2O$ (25 mL). The aqueous layer was extracted with EtOAc (3×50 mL) and the combined extracts were washed with brine (50 mL), dried ($MgSO_4$), filtered, and concentrated in vacuo. The residue was purified by flash silica gel chromatography (0-75% EtOAc/hexanes gradient) to afford syn 6-[3,5-bis(trifluoromethyl)phenyl]-4-methyl-1,3-oxazinan-2-one as a white solid. LCMS 328.1 $(M+1)^+$. $^1H$ NMR ($CDCl_3$, 500 MHz): δ 7.88 (s, 3H), 5.54 (s, 1H), 5.42 (dd, J=12, 1.9 Hz, 1H), 3.87-3.82 (m, 1H), 2.33-2.29 (m, 1H), 1.77-1.70 (m, 1H), 1.33 (d, J=6.3 Hz, 3H).

This compound was separated into its enantiomers (4R,6R)-6-[3,5-bis(trifluoromethyl)phenyl]-4-methyl-1,3-oxazinan-2-one and (4S,6S)-6-[3,5-bis(trifluoromethyl)phenyl]-4-methyl-1,3-oxazinan-2-one using chiral HPLC (5% IPA/heptane, ChiralPak IA column).

INTERMEDIATE 23

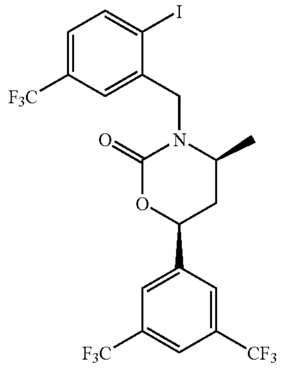

(4S,6S)-6-[3,5-bis(trifluoromethyl)phenyl]-3-[2-iodo-5-(trifluoromethyl)benzyl]-4-methyl-1,3-oxazinan-2-one To a stirred suspension of sodium hydride (60% in oil; 5.6 mg; 0.139 mmol) in THF (0.5 mL) at 0° C. under an atmosphere of $N_2$ was added a solution of (4S,6S)-6-[3,5-bis(trifluoromethyl)phenyl]-4-methyl-1,3-oxazinan-2-one (Intermediate 22; 50 mg; 0.153 mmol) in THF (1 mL) dropwise. The resultant mixture stirred at 0° C. for 15 min prior to dropwise addition of 2-(bromomethyl)-1-iodo-4-trifluoromethyl)benzene (Intermediate 11; 50.7 mg; 0.139 mmol) as a solution in THF (0.5 mL). The reaction was allowed to warm to room temperature and stirred for 14 h. The reaction was quenched with $H_2O$ and partitioned between EtOAc (25 mL) and $H_2O$ (15 mL). The aqueous layer was re-extracted with EtOAc (3×25 mL) and the combined extracts were washed with brine (25 mL), dried ($MgSO_4$), filtered and concentrated in vacuo. The residue was purified by flash silica gel chromatography (0-25% EtOAc/hexanes gradient) to afford (4S,6S)-6-[3,5-bis(trifluoromethyl)phenyl]-3-[2-iodo-5-(trifluoromethyl)benzyl]-4-methyl-1,3-oxazinan-2-one as a clear oil. LCMS=611.7 $(M+1)^+$. $^1H$ NMR ($CDCl_3$, 500 MHz): δ 8.02 (d, J=8.2 Hz, 1H), 7.91 (s, 2H), 7.89 (s, 1H), 7.52 (s, 1H), 7.29-7.26 (m, 1H), 5.44 (d, J=10.8 Hz, 1H), 4.88 (d, J=16.5 Hz, 1H), 4.62 (d, J=16.5 Hz, 1H), 3.77-3.70 (m, 1H), 2.45 (dd, J=14.1, 5.4 Hz, 1H), 2.06-1.98 (m, 1H), 1.22 (d, J=6.2 Hz, 3H).

INTERMEDIATE 24

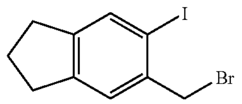

5-(Bromomethyl)-6-iodoindane

Step A: 6-iodoindan-5-amine

A mixture of 5-aminoindan (423 mg, 3.17 mmol), silver sulfate (990 mg, 3.17 mmol) and iodide (805 mg, 3.17 mmol) in methanol (20 mL) was stirred at room temperature overnight. The mixture was filtered and the solid was washed with a small amount of methanol. The filtrate was quenched with saturated $Na_2S_2O_3$ and then diluted with water. The aqueous layer was extracted with EtOAc (3×). The combined organic layers were washed with brine (1×), dried ($Na_2SO_4$) and concentrated in vacuo. Flash chromatography (Si, hexanes/EtOAc) of the residue yielded 6-iodoindan-5-amine (354 mg, 43%). LCMS calc.=258.99; found=260.0 $(M+1)^+$. $^1H$ NMR (500 MHz, $CDCl_3$) δ 7.51 (s, 1H), 6.69 (s, 1H), 3.97 (br, s, 2H), 3.02-2.90 (m, 1H), 2.81 (d, J=7.1 Hz, 3H), 2.12-2.02 (m, 2H).

Step B: 6-aminoindane-5-carbonitrile

To a solution of 6-iodoindan-5-amine (135 mg, 0.52 mmol) in DMF (2 mL), was added copper (I) cyanide (93 mg, 1.04 mmol). The mixture was heated at 160° C. for 1.5 h. The reaction mixture was poured into 10% $NH_4OH$. An equal amount of dichloromethane was added and resulting mixture was filtered. The filtrate was partitioned between two layers. The aqueous layer was extracted with dichloromethane (1×). The combined organic layers were concentrated in vacuo. The residue was dissolved in ethyl ether. The ether layer was washed with aqueous sodium bisulfite, dried with $Na_2SO_4$ and concentrated in vacuo. The residue was purified by flash chromatography (Si, hexanes/EtOAc) yielding 6-aminoindane-5-carbonitrile (48.5 mg, 59%). LCMS calc.=158.08; found=159.1 $(M+1)^+$. $^1H$ NMR (500 MHz, $CDCl_3$) δ 7.22 (s, 1H), 6.64 (s, 1H), 4.25 (br, s, 2H), 2.85 (t, J=7.4 Hz, 2H), 2.80 (t, J=7.4 Hz, 2H), 2.09-2.03 (m, 2H).

Step C: 6-iodoindane-5-carbonitrile

A mixture of 6-aminoindane-5-carbonitrile (48.5 mg, 0.307 mmol), isoamyl nitrite (82 μL, 0.614 mmol) and iodide (85.7 mg, 0.338 mmol) was stirred at room temperature for 0.5 h. The mixture was then heated at 80° C. under $N_2$ for 2 h. The reaction mixture was quenched with saturated $Na_2S_2O_3$ and partitioned between dichloromethane and water. The organic layer was dried ($Na_2SO_4$) and concentrated in vacuo. The residue was purified by flash chromatography (Si, 1% EtOAc in hexanes) to yield 6-iodoindane-5-carbonitrile (39.7 mg, 50%). LCMS calc.=268.97; found=270.0 $(M+1)^+$. $^1H$ NMR (500 MHz, $CDCl_3$) δ 7.78 (s, 1H), 7.48 (s, 1H), 2.96 (t, J=7.5 Hz, 2H), 2.92 (t, J=7.5 Hz, 2H), 2.16-2.10 (m, 2H).

Step D: 6-iodoindane-5-carbaldehyde

To a solution of 6-iodoindane-5-carbonitrile (36.5 mg, 0.136 mmol) in dichloromethane (1.0 mL) under $N_2$ at −78° C. was added a solution of 1N DIBALH in toluene (272 μL, 0.272 mmol) dropwise. The reaction was stirred at −78° C. for 15 min. Keeping the temperature at −78° C., another two portions of DIBALH (100 μL each) were added until the starting material disappeared by TLC. The reaction mixture was poured into 2N HCl (45 mL) and diluted with $Et_2O$. The mixture was stirred for 0.5 h. The $Et_2O$ layer was separated. The aqueous layer was extracted with $Et_2O$ (2×). The organic extracts were combined, dried ($Na_2SO_4$) and concentrated in vacuo. The residue was purified by flash chromatography (Si, hexanes/EtOAc) to afford 6-iodoindane-5-carbaldehyde (27 mg, 73%). $^1$H NMR (500 MHz, $CDCl_3$) δ 10.08 (s, 1H), 7.83 (s, 1H), 7.79 (s, 1H), 2.98 (t, J=7.5 Hz, 2H), 2.94 (t, J=7.5 Hz, 2H,), 2.19-2.13 (m, 2H).

Step, E: (6-iodo-2,3-dihydro-1H-inden-5-yl)methanol

To a solution of 6-iodoindane-5-carbaldehyde (35.5 mg, 0.131 mmol) in EtOH anhydrous (3 mL) under $N_2$ at 0° C., was added $NaBH_4$ (20 mg, 0.522 mmol) as a powder. The mixture was warmed to room temperature and stirred for 0.5 h. The mixture was quenched with water. The aqueous layer was extracted with EtOAc (3×). The combined organic extracts were dried ($Na_2SO_4$) and concentrated in vacuo. The residue was purified by flash chromatography (Si, hexanes/EtOAc) to afford (6-iodo-2,3-dihydro-1H-inden-5-yl)methanol (36.3 mg, 100%). $^1$H NMR (500 MHz, $CDCl_3$) δ 7.70 (s, 1H), 7.33 (s, 1H), 4.68 (d, J=6.3 Hz, 2H), 2.92-2.88 (m, 4H), 2.12-2.06 (m, 2H), 1.96 (t, J=6.4 Hz, 1H).

Step F: 5-(bromomethyl)-6-iodoindane

To a solution of (6-iodo-2,3-dihydro-1H-inden-5-yl) methanol (36 mg, 0.131 mmol) and carbon tetrabromide (52 mg, 0.158 mmol) in dichloromethane (1 mL) at 0° C. under $N_2$, was added triphenylphosphine (41 mg, 0.158 mmol). The resulting solution was allowed to warm to room temperature and was stirred for 4 h. Another portion of carbon tetrabromide (52 mg, 0.158 mmol) and triphenylphosphine (41 mg, 0.158 mmol) was added to the mixture at 0° C. The reaction mixture was stirred at room temperature overnight. The reaction mixture was concentrated in vacuo. The residue was purified by flash chromatography (Si, 1% EtOAc in hexanes) to afford 5-(bromomethyl)-6-iodoindane (44.4 mg, 100%). $^1$H NMR (500 MHz, $CDCl_3$) δ 7.72 (s, 1H), 7.36 (s, 1H), 4.62 (s, 2H), 2.89 (m, 4H), 2.11-2.07 (m, 2H).

INTERMEDIATE 25

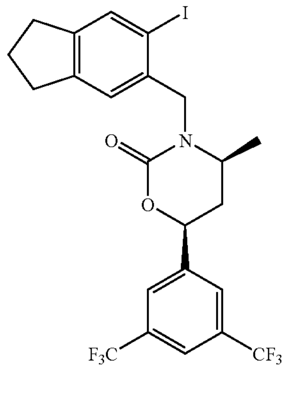

(4S,6S)-6-[3,5-bis(trifluoromethyl)phenyl]-3-[(6-iodo-2,3-dihydro-1H-inden-5-yl)methyl]-4-methyl-1,3-oxazinan-2-one (4S,6S)-6-[3,5-bis(trifluoromethyl)phenyl]-4-methyl-1,3-oxazinan-2-one (Intermediate 22; 104 mg; 0.318 mmol) was treated with sodium hydride (60% in oil; 11.9 mg; 0.297 mmol) and 5-(bromomethyl)-6-iodoindane (Intermediate 24; 100 mg; 0.297 mmol) as described for Intermediate 23 to afford (4S,6S)-6-[3,5-bis(trifluoromethyl)phenyl]-3-[(6-iodo-2,3-dihydro-1H-inden-5-yl)methyl]-4-methyl-1,3-oxazinan-2-one as a white solid. LCMS=583.8 $(M+1)^+$. $^1$H NMR ($CDCl_3$, 500 MHz): δ 7.90 (s, 2H), 7.87 (s, 1H), 7.72 (s, 1H), 7.19 (s, 1H), 5.43 (dd, J=11.8, 1.7 Hz, 1H), 4.96 (d, J=15-8 Hz, 1H), 4.47 (d, J=16 Hz, 1H), 3.69-3.62 (m, 1H), 2.90-2.86 (m, 4H), 2.43-2.38 (m, 1H), 2.12-2.05 (m, 2H), 2.00-1.92 (m, 1H), 1.25 (d, J=6.2 Hz, 3H).

INTERMEDIATE 26

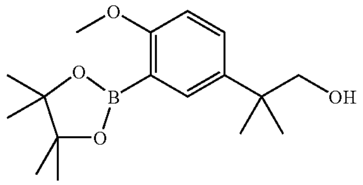

2-[4-methoxy-3-(4,4,5,5-tetramethyl-1,3,2-dioxaborolan-2-yl)phenyl]-2-methylpropan-1-ol Step, A: 2-(3-iodo-4-methoxyphenyl)-2-methylpropan-1-ol To a solution of 2-(4-methoxyphenyl)-2-methylpropan-1-ol (661.7 mg, 3.68 mmol) (2-(4-methoxyphenyl)-2-methylpropan-1-ol has been described in the literature. See *Helv. Chim. Acta.* 1971, 54, p. 868-897.) in EtOH (40 mL) was added $Ag_2SO_4$ (1.15 g, 3.68 mmol) followed by $I_2$ (934 mg, 3.68 mmol). The reaction was stirred at room temperature for 2 hours, and then the solids were filtered off through a pad of Celite. The filtrate was concentrated to ~10 mL and then diluted with EtOAc (50 mL). The organic solution was washed with water, aq. $NaHSO_3$, and brine (15 mL each). The organic layer was then diluted with 50 mL of hexanes and filtered through a short plug of silica gel with (50/50 EtOAc/hexanes). The filtrate was concentrated to afford 2-(3-iodo-4-methoxyphenyl)-2-methylpropan-1-ol. $^1$H NMR ($CDCl_3$, 500 MHz) δ 7.76 (d, J=2.3 Hz, 1H), 7.32 (dd, J=8.7, 2.3 Hz, 1H), 6.79 (d, J=8.7 Hz, 1H), 3.87 (s, 3H), 3.57 (s, 2H), 1.30 (s, 6H).

Step B: 2-[4-methoxy-3-(4,4,5,5-tetramethyl-1,3,2-dioxaborolan-2-yl)phenyl]-2-methylpropan-1-ol In a dry flask were placed 2-(3-iodo-4-methoxyphenyl)-2-methylpropan-1-ol (Step A; 180.0 mg, 0.584 mmol), [1,1'-bis (diphenylphosphino)-ferrocene]dichloropalladium(II). $CH_2Cl_2$ (47.7 mg, 0.0584 mmol), KOAc (115 mg, 1.17 mmol), and DMSO (8 mL). Bis(pinacolato)diboron (185.6 mg, 0.731 mmol) was dissolved in THF (340 μL) and added to the reaction. The reaction was degassed with $N_2$ and heated to 40° C. for 1 hour, then 60° C. for 1 hour, then at 80° C. for 12 hours. The reaction was then cooled to room temperature, diluted with EtOAc (75 mL), and washed with water (3×25 mL) and brine (25 mL). The organic layer was dried over $Na_2SO_4$, filtered, and concentrated. Purification of the residue by flash chromatography on silica gel (5 to 100% EtOAc/hexanes) afforded 2-[4-methoxy-3-(4,4,5,5-tetramethyl-1,3,2-dioxaborolan-2-yl)phenyl]-2-methylpropan-1-ol. $R_f$=0.25 (40% EtOAc/hexanes). $^1$H NMR ($CDCl_3$, 600 MHz) δ 7.64 (d, J=2.6 Hz, 1H), 7.40 (dd, J=8.6, 2.7 Hz, 1H), 6.83 (d, J=8.7 Hz, 1H), 3.82 (s, 3H), 3.59 (d, J=6.6 Hz, 2H), 1.35 (s, 12H), 1.32 (s, 6H).

INTERMEDIATE 27

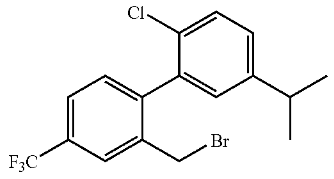

INTERMEDIATE 28

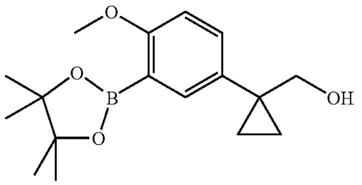

{1-[4-methoxy-3-(4,4,5,5-tetramethyl-1,3,2-dioxaborolan-2-yl)phenyl]cyclopropyl}methanol To a solution of 1-(4-methoxyphenyl)cyclopropanecarboxylic acid (1.0 g, 5.20 mmol) in THF (50 mL) was added $BH_3$ (7.8 mL of a 1M solution in THF, 7.8 mmol). The reaction was stirred at room temperature for 15 hours, and then quenched carefully by dropwise addition of water (10 mL). The solution volume was reduced to ~20 mL and then the mixture was extracted with EtOAc (75 mL). The organic layer was washed with water and brine (25 mL each), dried over $Na_2SO_4$, filtered, and concentrated, to afford [1-(3-iodo-4-methoxyphenyl)cyclopropyl]methanol. $^1$H NMR ($CDCl_3$, 500 MHz) δ 7.26-7.31 (m, 2H), 6.84-6.88 (m, 2H), 3.79 (s, 3H), 3.62 (s, 2H), 0.79-0.85 (m, 4H). This material was processed as described for Intermediate 26 to afford {1-[4-methoxy-3-(4,4,5,5-tetramethyl-1,3,2-dioxaborolan-2-yl)phenyl]cyclopropyl}methanol in two steps.

INTERMEDIATE 29

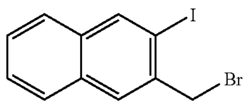

2-(Bromomethyl)-3-iodonaphthalene

Step A: (3-amino-2-naphthyl)methanol

A solution of 3-amino-2-naphthoic acid (85%, 1.17 g, 5.34 mmol) in dry THF (20 mL) was added dropwise over 30 min to a stirred solution of $LiAlH_4$ (95%, 0.53 g, 13.4 mmol) in dry THF (20 mL) at 0° C. under $N_2$. The mixture was stirred at room temperature overnight. Water (20 mL) was added and the mixture was adjusted to basic pH with 1N NaOH (20 mL). The mixture was filtered and extracted with $Et_2O$ (4×100 mL). The combined extracts were dried ($MgSO_4$) and concentrated in vacuo to afford (3-amino-2-naphthyl)methanol (0.88 g, 95%). LCMS calc.=174.1; found=174.2 $(M+1)^+$. $^1$H NMR (500 MHz, $CD_3OD$): δ 7.66 (d, J=8.0 Hz, 1H); 7.61 (s, 1H); 7.55 (d, J=8.2 Hz, 1H); 7.30-7.27 (m, 1H); 7.18-7.14 (m, 1H); 7.08 (s, 1H); 4.74 (s, 2H).

Step B: (3-iodo-2-naphthyl)methanol

A solution of (3-amino-2-naphthyl)methanol (500 mg, 2.89 mmol) in water (3 mL), acetone (3 mL) and concentrated HCl (1.6 mL) was cooled to 0° C. and a solution of $NaNO_2$ (219 mg, 3.18 mmol) in water (0.7 mL) was added. The reaction was stirred for 2 h at 0° C. and a solution of KI (719 mg, 4.33 mmol) and concentrated $H_2SO_4$ (0.16 mL) in water (1.2 mL) was added. The reaction mixture was heated at 60° C. for 2-3 h. The reaction mixture was cooled to room temperature and 50% saturated $Na_2SO_3$ (30 mL) was added. The mixture was extracted with $CH_2Cl_2$ (3×20 mL) and the combined extracts were washed with brine (20 mL), dried ($Na_2SO_4$) and concentrated in vacuo to give the crude product. This was purified by flash chromatography (Si, 25×160 mm, 0-40% EtOAc in hexanes gradient) to afford (3-iodo-2-naphthyl)methanol (423 mg, 52%). $R_f$=0.47 (20% EtOAc/hexanes). $^1$H NMR (600 MHz, $CD_3OD$): δ 8.35 (s, 1H); 7.91 (s, 1H); 7.81 (d, J=8.0 Hz, 1H); 7.71 (d, J=8.0 Hz, 1H); 7.47-7.42 (m, 2H); 4.69 (s, 2H).

Step C: 2-(bromomethyl)-3-iodonaphthalene

A solution of triphenylphosphine (469 mg, 1.79 mmol) in dry $CH_2Cl_2$ (2 mL) was added dropwise to a stirred solution of carbon tetrabromide (592 mg, 1.79 mmol) and (3-iodo-2-naphthyl)methanol (423 mg, 1.49 mmol) in dry $CH_2Cl_2$ (11 mL) at room temperature under $N_2$. The reaction was stirred for 4 h at room temperature and was concentrated in vacuo to give the crude product. This was purified by flash chromatography (Si, 25×160 mm, 0-50% EtOAc in hexanes gradient) to afford 2-(bromomethyl)-3-iodonaphthalene (469 mg, 91%), as a colorless solid. $R_f$=0.84 (20% EtOAc/hexanes). $^1$H NMR (600 MHz, $CDCl_3$): δ 8.39 (s, 1H); 7.94 (s, 1H); 7.78-7.76 (m, 1H); 7.71-7.69 (m, 1H); 7.52-7.48 (m, 2H); 4.76 (s, 2H).

INTERMEDIATE 30

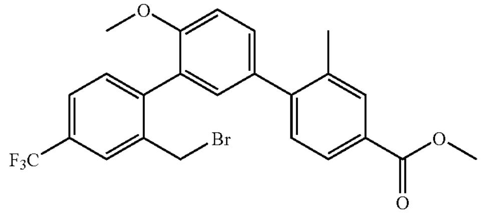

methyl 2"-(bromomethyl)-4'-methoxy-2-methyl-4"-(trifluoromethyl)-1,1':3',1"-terphenyl-4-carboxylate Step 1: methyl 4'-methoxy-2-methylbiphenyl-4-carboxylate To methyl 4-bromo-3-methyl benzoate (92 g, 0.402 mol), (4-methoxyphenyl)boronic acid (61.1 g, 0.402 mol), $Na_2CO_3$ (85.2 g, 0.804 mol), and $PdCl_2(PPh_3)_2$ (1410 mg, 2.01 mmol) was added EtOH (1.23 L) and water (0.61 L). The reaction was then heated to 80° C. for 1 hour. The reaction was cooled to room temperature, 550 ml of water was added, and the mixture was left standing for 1 hour. The resulting solids were filtered and washed with a solution of EtOH and $H_2O$ (1:1, 750 mL). The solids were ground using a mortar and pestle and then slurried in 250 mL $H_2O$ at room temperature for 1 h, then filtered and washed with water (2×125 mL) and dried to give methyl 4'-methoxy-2-methylbiphenyl-4-carboxylate. $^1$H NMR ($CDCl_3$, 400 MHz) δ 7.95 (s, 1H), 7.89 (d, J=7.9 Hz, 1H), 7.29 (d, J=7.9 Hz, 1H), 7.27 (d, J=8.7 Hz, 2H), 6.98 (d, J=8.7 Hz, 2H), 3.94 (s, 3H), 3.87 (s, 3H), 2.33 (s, 3H).

Step 2: methyl 3'-bromo-4'-methoxy-2-methylbiphenyl-4-carboxylate

To a solution of methyl 4'-methoxy-2-methylbiphenyl-4-carboxylate (71.5 g, 0.279 mol) in acetonitrile (1.43 L) and water (572 mL) was added oxone (180.1 g, 0.293 mol). Then a solution of KBr (38.2 g, 0.321 mol) in water (143 mL) was slowly added over 30 minutes. The reaction was stirred for 2.5 hours, then water (715 mL) was added and the mixture was left standing for 1 hour. The solids were filtered and washed as follows: with a solution of MeCN/water (1:1, 350 mL, twice), water (700 mL, twice, then 350 mL) and dried to afford methyl 3'-bromo-4'-methoxy-2-methylbiphenyl-4-carboxylate. $^1$H NMR ($CDCl_3$, 400 MHz) δ 7.94 (s, 1H), 7.89 (d, J=8.1 Hz, 1H), 7.53 (d, J=2.2 Hz, 1H), 7.3-7.2 (m, 2H), 6.97 (d, J=8.4 Hz, 1H), 3.96 (s, 3H), 3.94 (s, 3H), 2.32 (s, 3H).

Step 3: methyl 2"-(hydroxymethyl)-4'-methoxy-2-methyl-4"-(trifluoromethyl)-1,1':3',1"-terphenyl-4-carboxylate To methyl 3'-bromo-4'-methoxy-2-methylbiphenyl-4-carboxylate (80.0 g, 0.239 mol), pinacole borane (72.8 g, 0.287 mol), $Pd(dba)_2$ (4120 mg, 7.17 mmol), $P(Cy)_3$ (2140 mg, 7.65 mmol), and KOAc (70.3 g, 0.717 mol) was added dioxane (1.2 L). The reaction was heated to 80° C. and stirred for 3 hours. The reaction was then cooled to room temperature and filtered. The solids were dissolved with EtOAc (800 mL), washed with brine (400 mL, twice), and concentrated.

The residue was dissolved in THF (300 mL), and [2-chloro-5-(trifluoromethyl)phenyl]methanol (47.1 g, 0.223 mol) and $(t\text{-}Bu_2P)_2$ferrocene $PdCl_2$ were added. A solution of $K_2CO_3$ (83.7 g, 0.606 mol in water (214 mL) was added and the mixture was heated to 45° C. and stirred for 9 hours. The reaction was cooled to room temperature and diluted with EtOAc (428 mL), then washed with water (428 mL) and brine (428 mL). To the organic material was added 21.5 g charcoal (Darco KB—100 mesh) and the mixture was stirred for 1 hour. The mixture was filtered, and the solid material was washed with EtOAc (428 mL). The filtrate was concentrated and then re-dissolved in MeOH (677 mL) and left to stand for 1 hour. To the mixture was added water (169 mL) over 2 hours, and then the mixture was left to stand for 1 hour. The resulting solids were washed with a solution of MeOH and water (4:1, 170 mL, three times) and dried to afford methyl 2"-(hydroxymethyl)-4'-methoxy-2-methyl-4"-(trifluoromethyl)-1,1':3',1"-terphenyl-4-carboxylate.

Step 4: methyl 2"-(bromomethyl)-4'-methoxy-2-methyl-4"-(trifluoromethyl)-1,1':3',1"-terphenyl-4-carboxylate To a 0° C. solution of methyl 2"-(hydroxymethyl)-4'-methoxy-2-methyl-4"-(trifluoromethyl)-1,1':3',1"-terphenyl-4-carboxylate (1.500 g, 3.49 mmol) in $CH_2Cl_2$ (14 mL) was added $CBr_4$ (2.429 g, 7.33 mmol), and then a solution of triphenyl phosphine (1.830 g, 6.98 mmol) in $CH_2Cl_2$ (15 mL).

The solution was warmed to room temperature and stirred for twelve hours. The reaction was concentrated, and the residue was purified by flash chromatography on silica gel (0 to 25% EtOAc/hexanes) to afford methyl 2"-(bromomethyl)-4'-methoxy-2-methyl-4"-(trifluoromethyl)-1,1':3',1"-terphenyl-4-carboxylate. $R_f$=0.59 (50% EtOAc/hexanes). LCMS=494.8 $(M+1)^+$. $^1$H NMR ($CDCl_3$, 500 MHz), δ 7.95 (s, 1H), 7.89 (d, J=8.0 Hz, 1H), 7.80 (s, 1H), 7.59 (d, J=7.6 Hz, 1H), 7.40-7.33 (m, 3H), 7.21 (d, J=2.3 Hz, 1H), 7.06 (d, J=8.5 Hz, 1H), 4.44-4.39 (m, 2H), 3.93 (s, 3H), 3.82 (s, 3H), 2.37 (s, 3H).

Example 1

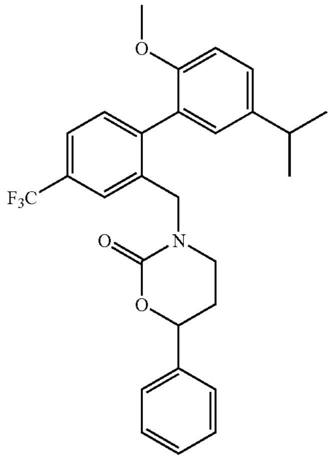 [SMILES: COc1ccc(C(C)C)cc1-c1ccc(C(F)(F)F)cc1CN1CCC(c2ccccc2)OC1=O]

3-{[5'-isopropyl-2'-methoxy-4-(trifluoromethyl)biphenyl-2-yl]methyl}-6-phenyl-1,3-oxazinan-2-one A mixture of 3-[2-iodo-5-(trifluoromethyl)benzyl]-6-phenyl-1,3-oxazinan-2-one (Intermediate 1, 51 mg, 0.11 mmol), 2-methoxy-5-isopropylphenyl boronic acid (86 mg, 0.11 mmol), potassium carbonate (76 mg, 0.55 mmol) and palladium acetate (7.4 mg, 0.011 mmol) in acetone (5 mL) and $H_2O$ (1 mL) was degassed and heated at reflux under $N_2$ for 1 h. The reaction mixture was concentrated, diluted with water (10 mL) and extracted with EtOAc (3×20 mL). The combined extracts were dried ($Na_2SO_4$) and concentrated in vacuo to give the crude product. This was purified by flash chromatography on silica gel (0-20% EtOAc in hexanes gradient) to afford 3-{[5'-isopropyl-2'-methoxy-4-(trifluoromethyl)biphenyl-2-yl]methyl}-6-phenyl-1,3-oxazinan-2-one as a colorless solid. LCMS=484.2 $(M+1)^+$. $^1$H NMR present (500 MHz, $CDCl_3$): δ 7.69 (br d, J=3.5 Hz, 1H), 7.62 (br d, J=8.0 Hz, 1H), 7.41-7.30 (m, 5H), 7.28 (d, J=2.5 Hz, 1H), 7.26 (d, J=2.5 Hz, 1H), 7.02 (d, J=2.3 Hz, 1H), 6.92 (d, J=8.5 Hz, 1H), 5.24 (dd, J=9.6, 2.5 Hz, 1H), 4.68 (d, J=3.2 Hz, 1H), 4.59 (d, J=15.5 Hz, 1H), 3.81 (s, 3H), 3.18-3.04 (m, 1H), 3.04-2.88 (m, 2H), 2.11 (m, 1H), 2.02 (m, 1H), 1.12 (d, J=7.1 Hz, 6H). The racemic material was separated by chiral HPLC using 15% IPA/heptane and an AD column.

Example 1A

The compound below was made following the general procedure described in Example 1. LC/MS (M+1) is 462.0.

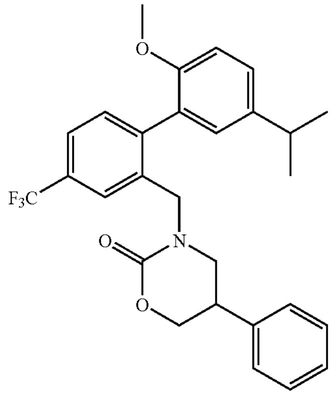 [SMILES: COc1ccc(C(C)C)cc1-c1ccc(C(F)(F)F)cc1CN1CC(c2ccccc2)COC1=O]

Example 2

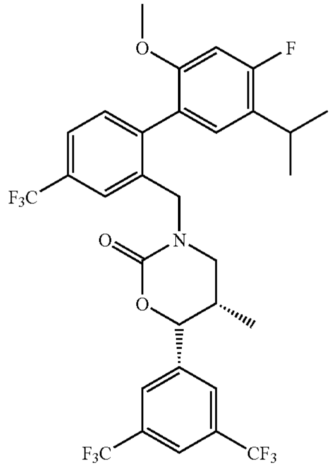

syn-6-[3,5-bis(trifluoromethyl)phenyl]-3-{[4'-fluoro-5'-isopropyl-2'-methoxy-4-(trifluoromethyl)biphenyl-2-yl]-methyl]-5-methyl-1,3-oxazinan-2-one To a stirred suspension of sodium hydride (60% in oil; 18 mg, 0.45 mmol) in THF (6 mL) at 0° C. under an atmosphere of $N_2$ was added syn 6-[3,5-bis(trifluoromethyl)phenyl]-5-methyl-1,3-oxazinan-2-one (Intermediate 20; 97 mg, 0.30 mmol) portionwise. The resultant solution was stirred at 0° C. for 20 min prior to the addition of a solution of 2'-(bromomethyl)-4-fluoro-5-isopropyl-2-methoxy-4'-(trifluoromethyl) biphenyl (Intermediate 13; 122 mg, 0.30 mmol) in THF (1 mL). The reaction was allowed to warm to room temperature and stirred for 14 h. The reaction was quenched with $H_2O$ and was partitioned between $H_2O$ (15 mL) and EtOAC (25 mL). The aqueous layer was re-extracted with EtOAc (3x25 mL) and the combined extracts were washed with brine (25 mL), dried ($MgSO_4$), filtered and concentrated in vacuo. The residue was purified by flash silica gel chromatography (0-10% EtOAc/hexanes gradient) to afford syn-3-{[4'-fluoro-5'-isopropyl-2'-methoxy-4-(trifluoromethyl)biphenyl-2-yl]methyl}-5-methyl-6-phenyl-1,3-oxazinan-2-one as a white solid LCMS=652.4 $(M+1)^+$. $^1H$ NMR ($CDCl_3$, 500 MHz, 1:1 mixture of atropisomers): δ 7.85 (s, 1H), 7.83 (s, 1H), 7.79 (s, 1H), 7.35-7.31 (m, 1H), 7.01-6.97 (m, 1H), 5.50 (br s, 0.5H), 5.37 (br s, 0.5H), 4.76 (d, J=15.6 Hz, 0.5H), 4.59 (d, J=15.6 Hz, 1H), 4.51 (d, J=15.8 Hz, 1H), 4.44 (d, J=15.5 Hz), 3.49 (dd, J=11.8, 4.9 Hz, 0.5H), 3.41 (dd, J=11.8, 4.9 Hz, 0.5H), 3.25 (m, 1H), 2.87 (d, J=11.6 Hz, 1H), 2.74 (d, J=11.6 Hz), 2.41-2.30 (m, 1H), 1.22 (m, 6H), 0.84 (d, J=7.0 Hz, 1.5H), 0.79 (d, J=6.9 Hz, 1H). The racemic material was separated by chiral HPLC using 3% IPA/heptane and an AD column.

Example 3

The compound below was made using the method described in Example 2. LC/MS (M+1) is 652.4.

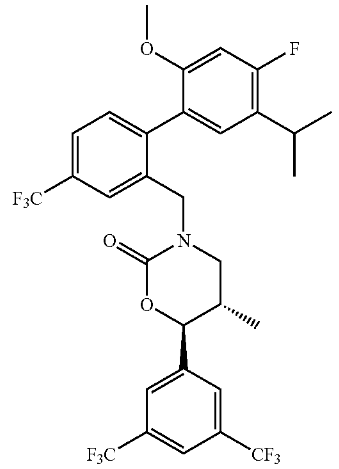 [SMILES: COc1cc(F)c(C(C)C)cc1-c1ccc(C(F)(F)F)cc1CN1C[C@H](C)[C@@H](c2cc(C(F)(F)F)cc(C(F)(F)F)c2)OC1=O]

Example 4

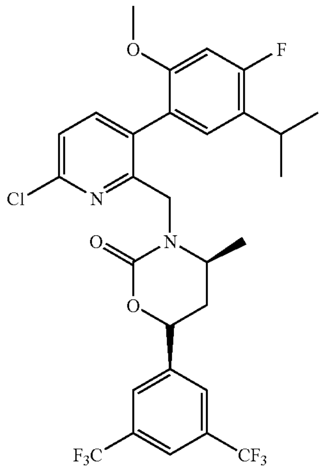

(4S,6S)-6-[3,5-bis(trifluoromethyl)phenyl]-3-{[6-chloro-3-(4-fluoro-5-isopropyl-2-methoxyphenyl) pyridine-2-yl]methyl}-4-methyl-1,3-oxazinan-2-one A mixture of (4S,6S)-6-[3,5-bis(trifluoromethyl)phenyl]-3-[(3-bromo-6-chloropyridin-2-yl)methyl]-4-methyl-1,3-oxazinan-2-one (Intermediate 2, 49 mg, 0-092 mmol), (4-fluoro-5-isopropyl-2-methoxyphenyl)boronic acid (Intermediate 6, 21 mg, 0.101 mmol) and 1,1-bis(di$^{t}$butylphosphino)ferrocene palladium dichloride (6 mg, 0.0092 mmol) in aqueous potassium carbonate/THF (3 mL, 3 mL) was heated at reflux for 2 h under $N_2$. After cooling to room temperature, the aqueous phase was separated and extracted with EtOAc (3×20 mL). The combined organic layers were dried ($Na_2SO_4$) and concentrated in vacuo to give the crude product. This was purified by flash chromatography on silica gel (0-15% EtOAc in hexanes gradient) to afford (4S,6S)-6-[3,5-bis(trifluoromethyl)phenyl]-3-{[6-chloro-3-(4-fluoro-5-isopropyl-2-methoxyphenyl)pyridin-2-yl]methyl}-4-methyl-1,3-oxazinan-2-one as a colorless oil. LCMS=619.0 $(M+1)^+$. $^1$H NMR ($CDCl_3$, 500 MHz): δ 7.88 (br s, 2H), 7.84 (s, 1H), 7.68 (brs, 2H), 7.49 (d, J=8.0 Hz, 1H), 7.31 (d, J=8.0 Hz, 1H), 7.28 (br s, 1H), 6.71 (d, J=12.1 Hz, 1H), 5.88 (brs, 1H), 5.25 (br d, J=16.7 Hz, 1H), 4.21 (br m, 2H), 3.95 (br m, 2H), 3.81 (s, 3H), 3.21 (m, 1H), 2.39 (m, 2H), 1.92 (m, 1H), 2.11 (3H, s), 1.29 (br d, 9H).

Example 5

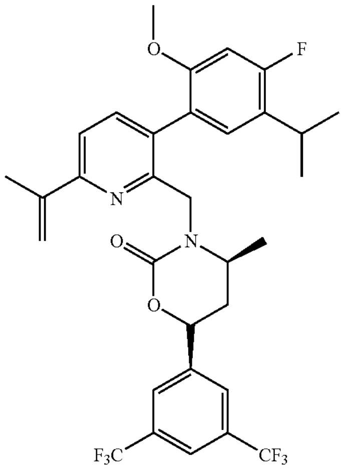

(4S,6S)-6-[3,5-bis(trifluoromethyl)phenyl]-3-{[3-(4-fluoro-5-isopropyl-2-methoxyphenyl)-6-isopropenylpyridin-2-yl]methyl}-4-methyl-1,3-oxazinan-2-one A mixture of (4S,6S)-6-[3,5-bis(trifluoromethyl)phenyl]-3-{[6-chloro-3-(4-fluoro-5-isopropyl-2-methoxyphenyl)pyridin-2-yl]methyl)}-4-methyl-1,3-oxazinan-2-one (Example 4, 16 mg, 0.026 mmol), isopropenyl boronic acid (22 mg, 0.26 mmol) and 1,1-bis(di$^t$butylphosphino)ferrocene palladium dichloride (2 mg, 0.0026 mmol) in aqueous potassium carbonate/THF (1 mL, 1 mL) was heated at reflux for 2.5 h under $N_2$. After cooling to room temperature, the aqueous phase was separated and extracted with EtOAc (3×20 mL). The combined organic layers were dried ($Na_2SO_4$) and concentrated in vacuo to give the crude product. This was purified by flash chromatography on silica gel (0-15% EtOAc in hexanes gradient) to afford (4S,6S)-6-[3,5-bis(trifluoromethyl)phenyl]-3-{[3-(4-fluoro-5-isopropyl-2-methoxyphenyl)-6-isopropenylpyridin-2-yl]methyl}-4-methyl-1,3-oxazinan-2-one. LCMS=625.2 $(M+1)^+$. $^1$H NMR ($CDCl_3$, 500 MHz): δ 7.85 (br s, 3H), 7.51 (m, 2H), 7.05 (m, 1H), 6.71 (d, J=11.9 Hz, 1H), 5.98 (br s, 1H), 5.35 (br s, 1H), 5.31 (br m, 1H), 4.32 (br m, 1H), 3.79 (s, 3H), 3.22 (br m, 1H), 2.28 (s, 3H), 1.89 (m, 2H), 1.27 (br m, 9H).

Example 6

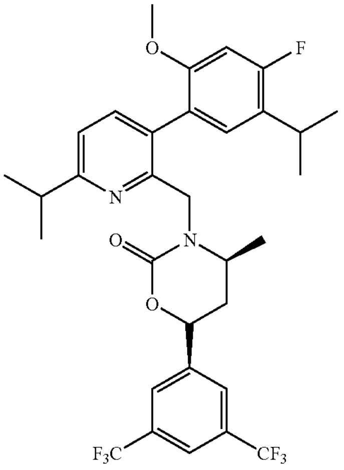

(4S,6S)-6-[3,5-bis(trifluoromethyl)phenyl]-3-{[3-(4-fluoro-5-isopropyl-2-methoxyphenyl)-6-isopropylpyridin-2-yl]methyl}-4-methyl-1,3-oxazinan-2-one A solution of (4S,6S)-6-[3,5-bis(trifluoromethyl)phenyl]-3-{[3-(4-fluoro-5-isopropyl-2-methoxyphenyl)-6-isopropenylpyridin-2-yl]methyl}-4-methyl-1,3-oxazinan-2-one (Example 5, 8.0 mg, 0.011 mmol) in EtOH (2 mL) was charged with hydrogen at 1 atm with catalytic amount of Pd/C. The mixture was stirred at room temperature for 1 h. The mixture was filtered through Celite and concentrated. The title compound was obtained after flash chromatography on silica gel using EtOAc:hexane 10:90 as the elute to afford 4S,6S)-6-[3,5-bis(trifluoromethyl)phenyl]-3-{[3-(4-fluoro-5-isopropyl-2-methoxyphenyl)-6-isopropylpyridin-2-yl]methyl}-4-methyl-1,3-oxazinan-2-one. LCMS=627.2 $(M+1)^+$. $^1$H NMR ($CDCl_3$, 500 MHz): δ 7.86 (s, 3H), 7.68 (brs, 1H), 7.18 (brs, 1H), 7.14 (br m, 1H), 6.71 (d, J=11.9 Hz, 1H), 5.31-5.27 (m, 2H), 4.31-4.24 (m, 2H), 3.80 (s, 3H), 2.21 (m, 1H), 1.82 (m, 1H), 1.26 (br s, 3H), 1.21 (br m, 12H).

Example 7

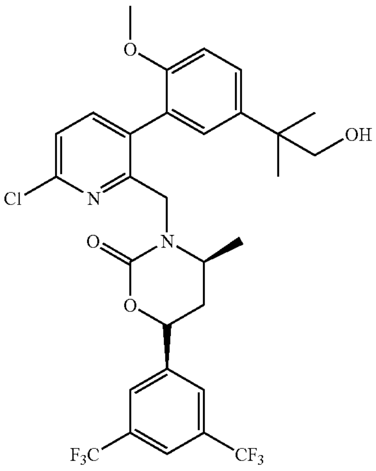

(4S,6S)-6-[3,5-bis(trifluoromethyl)phenyl]-3-({6-chloro-3-[5-(2-hydroxy-1,1-dimethylethyl)-2-methoxyphenyl]pyridine-2-yl}methyl)-4-methyl-1,3-oxazinan-2-one A mixture of (4S,6S)-6-[3,5-bis(trifluoromethyl)phenyl]-3-[(3-bromo-6-chloropyridin-2-yl)methyl]-4-methyl-1,3-oxazinan-2-one (intermediate 2, 32 mg, 0.06 mmol), 2-[4-methoxy-3-(4,4,5,5-tetramethyl-1,3,2-dioxaborolan-2-yl)phenyl]-2-methylpropan-1-ol (Intermediate x, 18 mg, 0.06 mmol) and 1,1-bis(di$^t$butylphosphino)ferrocene palladium dichloride (4 mg, 0.006 mmol) in aqueous potassium carbonate/THF (3 mL, 3 mL) was heated at reflux for 2 h under $N_2$. After cooling to room temperature, the aqueous phase was separated and extracted with EtOAc (3×20 mL). The combined organic layers were dried ($Na_2SO_4$) and concentrated in vacuo to give the crude product. This was purified by flash chromatography on silica gel (0-15% EtOAc in hexanes gradient) to (4S,6S)-6-[3,5-bis(trifluoromethyl)phenyl]-3-({6-chloro-3-[5-(2-hydroxy-1,1-dimethylethyl)-2-methoxyphenyl]pyridine-2-yl}methyl)-4-methyl-1,3-oxazinan-2-one as a colorless oil. LCMS=631.1 $(M+1)^+$. $^1$H NMR ($CDCl_3$, 500 MHz, 1:1 mixture of atroisomers): δ 7.87 (br s, 2H), 7.82 (s, 1H), 7.58 (brs, 1H), 7.44 (br d, J=6.8 Hz, 1H), 7.32 (brs, 1H), 7.24 (brs, 1H), 7.02 (d, J=8.7 Hz, 1H), 5.62-5.41 (br m, 0.5H), 5.26-5.20 (brm, 0.5H), 5.16-5.11 (brm, 1H), 4.34 (brm, 3H), 3.80 (s, 3H), 3.62-3.44 (brm, 3H), 1.34 (brs, 3H), 1.22 (brm, 6H).

Example 10

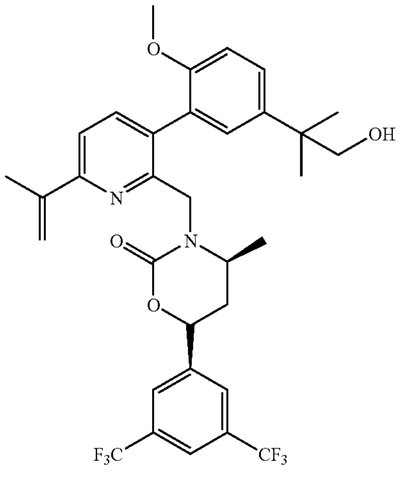

(4S,6S)-6-[3,5-bis(trifluoromethyl)phenyl]-3-({3-[5-(2-hydroxy-1,1-dimethylethyl)-2-methoxyphenyl]-6-isopropenylpyridin-2-yl}methyl-4-methyl-1,3-oxazinan-2-one A mixture of (4S,6S)-6-[3,5-bis(trifluoromethyl)phenyl]-3-({6-chloro-3-[5-(2-hydroxy-1,1-dimethylethyl)-2-methoxyphenyl]pyridine-2-yl}methyl)-4-methyl-1,3-oxazinan-2-one (Example 10, 8 mg, 0.013 mmol), isopropenyl boronic acid (12 mg, 0.14 mmol) and 1,1-bis(di$^t$butylphosphino)ferrocene palladium dichloride (1 mg, 0.0013 mmol) in aqueous potassium carbonate/THF (1 mL, 1 mL) was heated at reflux for 2.5 h under $N_2$. After cooling to room temperature, the aqueous phase was separated and extracted with EtOAc (3×15 mL). The combined organic layers were dried ($Na_2SO_4$) and concentrated in vacuo to give the crude product. This was purified by flash chromatography on silica gel (0-15% EtOAc in hexanes gradient) to afford (4S,6S)-6-[3,5-bis(trifluoromethyl)phenyl]-3-{[3-(4-fluoro-5-isopropyl-2-methoxyphenyl)-6-isopropenylpyridin-2-yl]methyl}-4-methyl-1,3-oxazinan-2-one. LCMS=637.2 $(M+1)^+$. $^1$H NMR ($CDCl_3$, 500 MHz, 1:1 mixture of atroisomers): δ 7.87 (br s, 2H), 7.81 (s, 1H), 7.60 (brs, 1H), 7.44 (br d, J=6.8 Hz, 1H), 7.35 (brs, 1H), 7.21 (brs, 1H), 7.01 (d, J=8.7 Hz, 1H), 5.16-5.11 (brm, 1H), 4.31 (brm, 3H), 3.76 (s, 3H), 3.61-3.46 (brm, 3H), 1.34 (brs, 3H), 1.32 (brm, 6H), 1.20 (br s, 6H).

Example 11

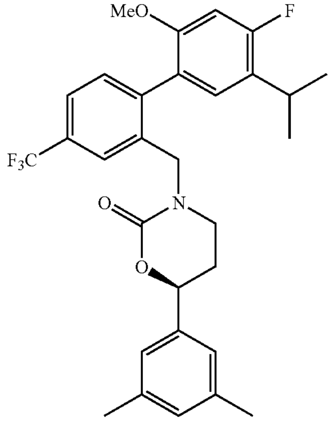 [SMILES: COc1cc(F)c(C(C)C)cc1-c1ccc(C(F)(F)F)cc1CN1CC[C@@H](c2cc(C)cc(C)c2)OC1=O]

(6S)-6-(3,5-dimethylphenyl)-3-{[4'-fluoro-5'-isopropyl-2'-methoxy-4-(trifluoromethyl)biphenyl-2-yl]methyl}-1,3-oxazinan-2-one To a stirred suspension of sodium hydride (60% in oil; 7.4 mg; 0.185 mmol) in THF (1.5 mL) at 0° C. under $N_2$ was added a solution of (6S)-6-(3,5-dimethylphenyl)-1,3-oxazinan-2-one (Intermediate 21; 30 mg; 0.148 mmol) in THF (2 mL) dropwise. The reaction was stirred at 0° C. for 20 min prior to addition of 2'-(bromomethyl)-4-fluoro-5-isopropyl-2-methoxy-4'-(trifluoromethyl)biphenyl (Intermediate 13; 50 mg; 0.123 mmol) as a solution in THF (1.5 mL). The reaction was allowed to warm to room temperature and stirred for 72 h, then quenched with $H_2O$ and partitioned between EtOAc (25 mL) and $H_2O$ (10 mL). The aqueous layer was extracted with EtOAc (3×25 mL). The combined organic layers were washed with brine (25 mL), dried over $MgSO_4$, filtered, and concentrated in vacuo. The crude product was purified first by flash silica gel chromatography (0-25% EtOAc/hexanes gradient) and then by chiral HPLC (Chiralpak AD column; 15% IPA/heptane) to afford (6S)-6-(3,5-dimethylphenyl)-3-{[4'-fluoro-5'-isopropyl-2'-methoxy-4-(trifluoromethyl)biphenyl-2-yl]methyl}-1,3-oxazinan-2-one as a clear oil. LCMS=530.3 $(M+1)^+$. $^1$H NMR ($CDCl_3$, 500 MHz): δ 7.66 (d, J=7.8 Hz, 1H), 7.61 (d, J=8 Hz, 1H), 7.34 (d, J=8 Hz, 1H), 7.01-6.96 (m, 4H), 6.70 (d, J=12.1 Hz, 1H), 5.23-5.13 (m, 1H), 4.66-4.49 (m, 2H), 3.78 (s, 3H), 3.26-3.20 (m, 1H), 3.17-3.06 (m, 1H), 3.01-2.93 (m, 1H), 2.34 (s, 6H), 2.18-2.13 (m, 1H), 2.09-2.02 (m, 1H), 1.29-1.24 (m, 6H).

Example 12

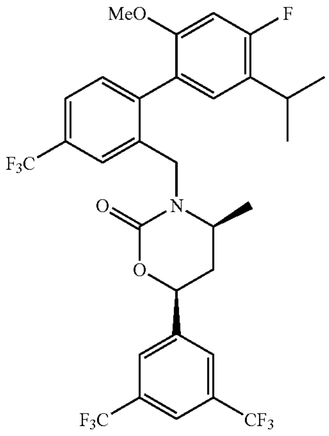 [SMILES: COc1cc(F)c(C(C)C)cc1-c1ccc(C(F)(F)F)cc1CN1C(=O)O[C@H](c2cc(C(F)(F)F)cc(C(F)(F)F)c2)C[C@@H]1C]

(4S,6S)-6-[3,5-bis(trifluoromethyl)phenyl]-3-{[4'-fluoro-5'-isopropyl-2'-methoxy-4-(trifluoromethyl)biphenyl-2-yl]methyl}-4-methyl-1,3-oxazinan-2-one To a stirred solution of 2'-(bromomethyl)-4-fluoro-5-isopropyl-2-methoxy-4'-(trifluoromethyl)biphenyl (Intermediate 13; 61.7 mg; 0.152 mmol) and (4S,6S)-6-[3,5-bis(trifluoromethyl)phenyl]-4-methyl-1,3-oxazinan-2-one (Intermediate 22; 41.5 mg; 0.127 mmol) in DMF (1 mL) under an atmosphere of $N_2$ was added potassium tert-butoxide (14.2 mg; 0.127 mmol). The reaction stirred at room temperature for 1 h and was quenched with sat. $NH_4Cl$. The reaction was partitioned between EtOAc (15 mL) and sat. $NH_4Cl$ (10 mL). The aqueous layer was re-extracted with EtOAc (4×25 mL), and the combined extracts were washed with brine, dried ($MgSO_4$), filtered and concentrated in vacuo. The residue was purified by flash silica gel chromatography (0-10% EtOAc/hexanes gradient) to afford (4S,6S)-6-[3,5-bis(trifluoromethyl)phenyl]-3-{[4'-fluoro-5'-isopropyl-2'-methoxy-4-(trifluoromethyl)biphenyl-2-yl]methyl}-4-methyl-1,3-oxazinan-2-one as a white solid. LCMS=652.3 $(M+1)^+$. $^1$H NMR ($CDCl_3$, 500 MHz, mixture of atropisomers): δ 7.87 (s, 2H), 7.79 (s, 1H), 7.65 (s, 1H), 7.62-7.59 (m, 1H), 7.36-7.32 (m, 1H), 7.03 (d, J=10.9 Hz, 1H), 6.70 (d, J=11.9 Hz, 1H), 5.21 (d, J=10.5 Hz, 1H), 5.10 (d, J=16.3 Hz, 1H), 4.39 (d, J=16 Hz, 1H), 3.78 (s, 3H), 3.45-3.37 (m, 1H), 3.25-3.18 (m, 1H), 2.32-2.22 (m, 1H), 1.91-1.78 (m, 1H), 1.27-1.21 (m, 6H), 1.02 (d, J=6.2 Hz, 3H).

The compounds in Table 1 were prepared by methods analogous to those described in Examples 11-12.

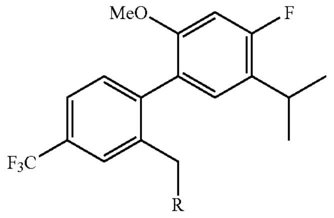

| EXAMPLE | R | LCMS $(M + 1)^+$ |
|---|---|---|
| 13 | 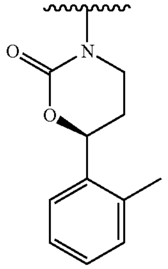 [SMILES: *N1CC[C@@H](c2ccccc2C)OC1=O] | 516.3 |
| 14 | 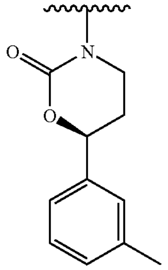 [SMILES: *N1CC[C@@H](c2cccc(C)c2)OC1=O] | 516.4 |
| 15 | 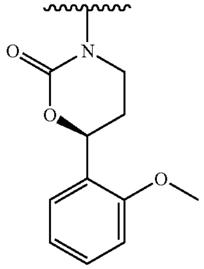 [SMILES: *N1CC[C@@H](c2ccccc2OC)OC1=O] | 532.2 |
| 16 | 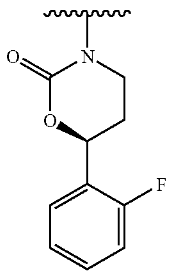 [SMILES: *N1CC[C@@H](c2ccccc2F)OC1=O] | 520.2 |

-continued
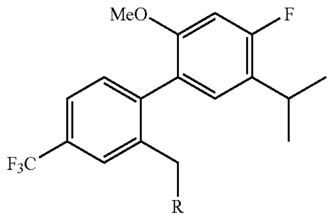
| EXAMPLE | R | LCMS (M + 1)+ |
|---|---|---|
| 17 | 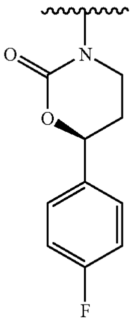 [SMILES: *N1CC[C@@H](c2ccc(F)cc2)OC1=O] | 520.3 |
| 18 | 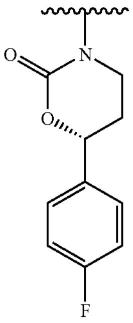 [SMILES: *N1CC[C@H](c2ccc(F)cc2)OC1=O] | 520.3 |
| 19 | 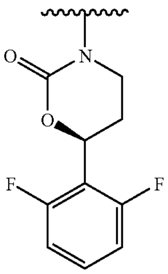 [SMILES: *N1CC[C@@H](c2c(F)cccc2F)OC1=O] | 538.2 |
| 20 | 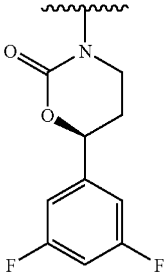 [SMILES: *N1CC[C@@H](c2cc(F)cc(F)c2)OC1=O] | 538.4 |
-continued
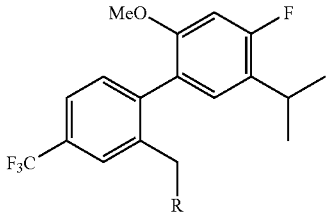
| EXAMPLE | R | LCMS (M + 1)+ |
|---|---|---|
| 21 | 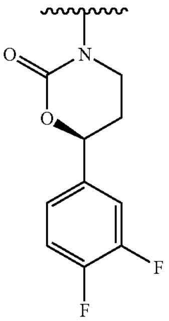 [SMILES: *N1CC[C@@H](c2ccc(F)c(F)c2)OC1=O] | 538.4 |
| 22 | 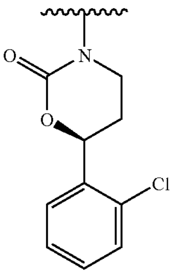 [SMILES: *N1CC[C@@H](c2ccccc2Cl)OC1=O] | 536.3 |
| 23 | 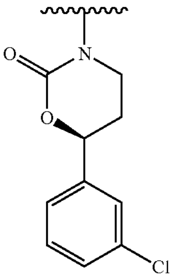 [SMILES: *N1CC[C@@H](c2cccc(Cl)c2)OC1=O] | 536.3 |
| 24 | 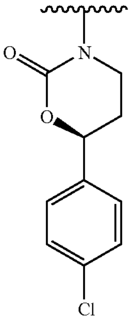 [SMILES: *N1CC[C@@H](c2ccc(Cl)cc2)OC1=O] | 536.3 |

-continued
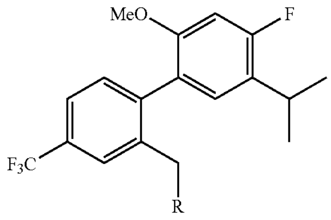
| EXAMPLE | R | LCMS (M + 1)$^+$ |
|---|---|---|
| 25 | 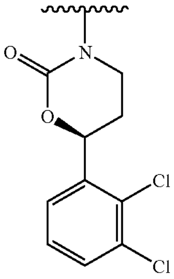 [SMILES: *N1CC[C@@H](c2cccc(Cl)c2Cl)OC1=O] | 570.2 |
| 26 | 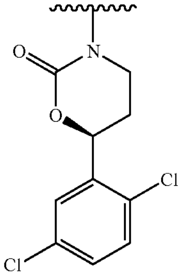 [SMILES: *N1CC[C@@H](c2cc(Cl)ccc2Cl)OC1=O] | 570.2 |
| 27 | 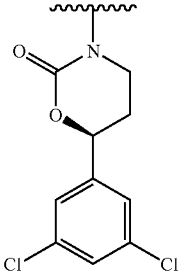 [SMILES: *N1CC[C@@H](c2cc(Cl)cc(Cl)c2)OC1=O] | 570.3 |
| 28 | 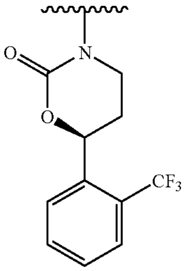 [SMILES: *N1CC[C@@H](c2ccccc2C(F)(F)F)OC1=O] | 570.3 |
-continued
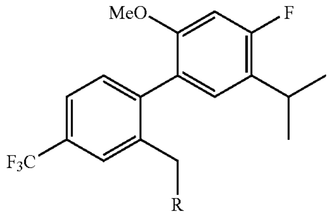
| EXAMPLE | R | LCMS (M + 1)$^+$ |
|---|---|---|
| 29 | 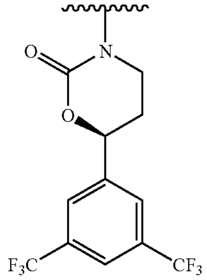 [SMILES: *N1CC[C@@H](c2cc(C(F)(F)F)cc(C(F)(F)F)c2)OC1=O] | 638.4 |
| 30 | 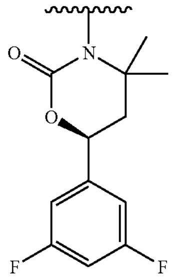 [SMILES: *N1C(=O)O[C@H](c2cc(F)cc(F)c2)CC1(C)C] | 566.3 |
| 31 | 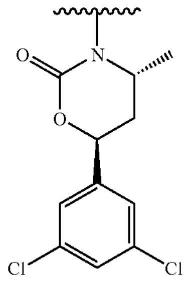 racemic | 584.3 |
| 32 | 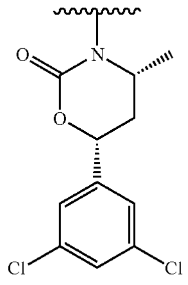 racemic | 584.3 |

-continued

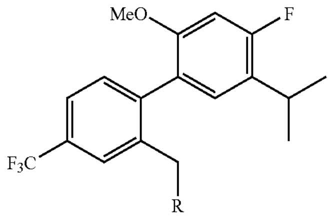

| EXAMPLE | R | LCMS (M + 1)$^+$ |
|---|---|---|
| 33 | 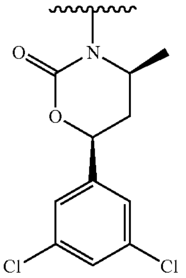 [SMILES: *N1C(=O)O[C@H](c2cc(Cl)cc(Cl)c2)C[C@@H]1C] | 584.1 |
| 34 | 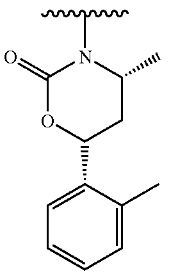 | 530.2 |
| 35 | 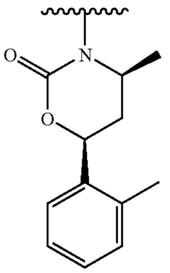 [SMILES: *N1C(=O)O[C@H](c2ccccc2C)C[C@@H]1C] | 530.2 |

Example 36

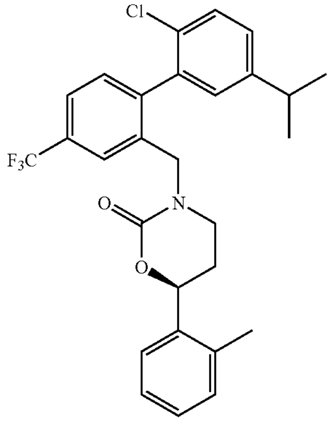 [SMILES: Cc1ccccc1[C@@H]1CCN(Cc2cc(C(F)(F)F)ccc2-c2cc(C(C)C)ccc2Cl)C(=O)O1]

(6S)-3-{[2'-chloro-5'-isopropyl-4-(trifluoromethyl)biphenyl-2-yl]methyl}-6-(2-methylphenyl)-1,3-oxazinan-2-one (6S)-6-(2-methylphenyl)-1,3-oxazinan-2-one (prepared from ethyl-4-(2-methylphenyl)-4-oxobutyrate by a procedure analogous to that reported for Intermediate 21; 20 mg; 0.10 mmol) was treated with sodium hydride (60% in oil; 8.0 mg; 0.20 mmol) and 2-(bromomethyl)-2'-chloro-5'-isopropyl-4-(trifluoromethyl)biphenyl (Intermediate 27; 41 mg; 0.10 mmol) as described in Example 11 to afford (6S)-3-{[2'-chloro-5'-isopropyl-4-(trifluoromethyl)biphenyl-2-yl]methyl}-6-(2-methylphenyl)-1,3-oxazinan-2-one as a white solid. LCMS=502.1 (M+1)$^+$. $^1$H NMR ($CDCl_3$, 500 MHz, mixture of atropisomers): δ 7.78 (s, 1H), 7.67-7.64 (m, 1H), 7.48 (d, J=8.1 Hz, 1H), 7.45 (s, 1H), 7.40-7.37 (m, 1H), 7.28-7.24 (m, 3H), 7.19-7.17 (m, 1H), 7.11 (dd, J=8, 2.1 Hz, 1H), 5.51 (dd, J=9.9, 2.8 Hz, 1H), 4.69 (d, J=15.8 Hz, 1H), 4.45 (d, J=15.8 Hz, 1H), 3.31-3.21 (m, 1H), 3.14-3.10 (m, 1H), 2.98-2.93 (m, 1H), 2.35 (s, 3H), 2.20-2.15 (m, 1H), 2.14-2.04 (m, 1H) 1.29 (d, J=6.9 Hz, 6H).

Example 37

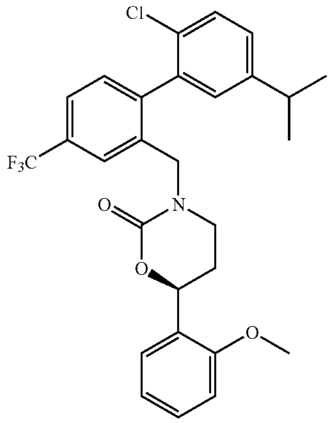 [SMILES: COc1ccccc1[C@@H]1CCN(Cc2cc(C(F)(F)F)ccc2-c2cc(C(C)C)ccc2Cl)C(=O)O1]

(6S)-3-{[2'-chloro-5'-isopropyl-4-(trifluoromethyl)biphenyl-2-yl]methyl}-6-(2-methoxyphenyl)-1,3-oxazinan-2-one (6S)-6-(2-methoxyphenyl) 1,3-oxazinan-2-one (prepared from ethyl-4-(2-methoxyphenyl)-4-oxobutyrate by a procedure analogous to that reported for Intermediate 21; 20 mg; 0.10 mmol) was treated with sodium hydride (60% in oil; 8.0 mg; 0.20 mmol) and 2-(bromomethyl)-2'-chloro-5'-isopropyl-4-(trifluoromethyl)-biphenyl (Intermediate 27; 39 mg; 0.10 mmol) as described in Example 11 to afford (6S)-3-{[2'-chloro-5'-isopropyl-4-(trifluoromethyl)biphenyl-2-yl]methyl}-6-(2-methoxyphenyl)-1,3-oxazinan-2-one as a white solid. LCMS=518.1 $(M+1)^+$. $^1H$ NMR ($CDCl_3$, 500 MHz, mixture of atropisomers): δ 7.76 (s, 1H), 7.64 (d, J=8.1 Hz, 1H), 7.50 (d, J=6.4 Hz, 1H), 7.44 (s, 1H), 7.37-7.35 (m, 1H), 7.34-30 (m, 1H), 7.26-7.24 (m, 1H), 7.09 (dd, J=7.8, 2.3 Hz, 1H), 7.06-7-7.00 (m, 1H), 6.90 (d, J=8.2 Hz, 1H), 5.66 (dd, J=8.7, 3.0 Hz, 1H), 4.71 (d, J=15.8 Hz, 1H), 4.39 (d, J=15.8 Hz, 1H), 3.85 (s, 3H), 3.25-3.17 (m, 1H), 3.09-3.04 (m, 1H), 2.97-2.92 (m, 1H), 2.31-2.25 (m, 1H), 2.06-1.99 (m, 1H) 1.28 (d, J=7.1 Hz, 6H).

Example 38

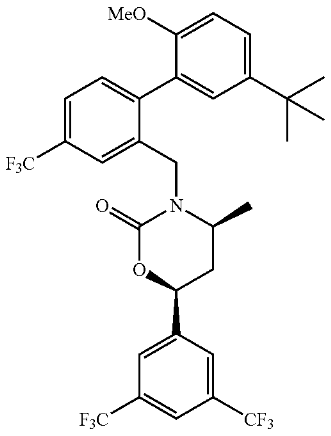 [SMILES: COc1ccc(C(C)(C)C)cc1-c1ccc(C(F)(F)F)cc1CN1C(=O)O[C@H](c2cc(C(F)(F)F)cc(C(F)(F)F)c2)C[C@@H]1C]

(4S,6S)-6-[3,5-bis(trifluoromethyl)phenyl]-3-{[5'-tert-butyl-2'-methoxy-4-(trifluoromethyl)biphenyl-2-yl]methyl}-4-methyl-1,3-oxazinan-2-one (4S,6S)-6-[3,5-bis(trifluoromethyl)phenyl]-3-[2-iodo-5-(trifluoromethyl)benzyl]-4-methyl-1,3-oxazinan-2-one (Intermediate 23; 25 mg; 0.041 mmol), (5-tert-butyl-2-methoxyphenyl)boronic acid (11.1 mg; 0.053 mmol), 1-1'-bis(di tert-butylphosphino)ferrocene palladium dichloride (2.7 mg; 0.0041 mmol), 1 N $K_2CO_3$ (1.2 mL) and THF (1.2 mL) were combined in a sealed tube and heated at 80° C. for 1.5 h. The reaction was diluted with $H_2O$ (10 mL) and extracted with EtOAc (3×10 mL). The combined extracts were washed with brine (10 mL), dried ($Na_2SO_4$), filtered and concentrated in vacuo. The residue was purified by flash silica gel chromatography (0-30% EtOAc/hexanes gradient) to afford (4S,6S)-6-[3,5-bis(trifluoromethyl)phenyl]-3-{[5'-tert-butyl-2'-methoxy-4-(trifluoromethyl)biphenyl-2-yl]methyl}-4-methyl-1,3-oxazinan-2-one as a white solid. LCMS=648.0 $(M+1)^+$. $^1H$ NMR ($CDCl_3$, 500 MHz, mixture of atropisomers): δ 7.86-7.83 (m, 2H), 7.78 (s, 1H), 7.68 (s, 1H), 7.63-7.59 (m, 1H), 7.44-7.36 (m, 2H), 7.18 (dd, J=6.7, 2.4 Hz, 1H), 6.94 (d, J=8.7 Hz, 1H), 5.20 (d, J=16 Hz, 1H), 5.16 (d, J=11.2 Hz, 1H), 4.38 (d, J=15.8 Hz, 1H), 3.80 (s, 3H), 3.41-3.34 (m, 1H), 2.29-2.24 (m, 1H), 1.88-1.81 (m, 1H), 1.32 (s, 9H), 1.02 (d, J=6.2 Hz, 3H).

Example 39

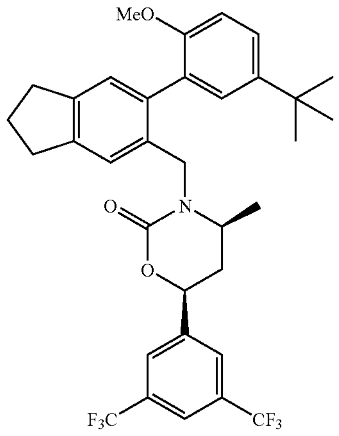 [SMILES: COc1ccc(C(C)(C)C)cc1-c1cc2c(cc1CN1C(=O)O[C@H](c3cc(C(F)(F)F)cc(C(F)(F)F)c3)C[C@@H]1C)CCC2]

(4S,6S)-6-[3,5-bis(trifluoromethyl)phenyl]-3-{[6-(5-tert-butyl-2-methoxyphenyl)-2,3-dihydro-1H-inden-5-yl]methyl}-4-methyl-1,3-oxazinan-2-one (4S,6S)-6-[3,5-bis(trifluoromethyl)phenyl]-3-[(6-iodo-2,3-dihydro-1H-inden-5-yl)methyl]-4-methyl-1,3-oxazinan-2-one (Intermediate 25; 25 mg; 0.043 mmol) was treated with (5-tert-butyl-2-methoxyphenyl)boronic acid (11.6 mg; 0.056 mmol), 1-1'-bis(di tert-butylphosphino)ferrocene palladium dichloride (2.8 mg; 0.0043 mmol), 1 N $K_2CO_3$ (1.2 mL) and THF (1.2 mL) as described in Example 38 to afford (4S,6S)-6-[3,5-bis(trifluoromethyl)phenyl]-3-{[6-(5-tert-butyl-2-methoxyphenyl)-2,3-dihydro-1H-inden-5-yl]methyl}-4-methyl-1,3-oxazinan-2-one as a clear glass. LCMS=620.1 $(M+1)^+$. $^1H$ NMR ($CDCl_3$, 500 MHz, mixture of atropisomers): δ 7.84-7.82 (m, 2H), 7.75 (s, 1H), 7.36 (dd, J=8.5, 2.6 Hz, 1H), 7.31 (s, 1H), 7.22 (d, J=2.5 Hz, 1H), 7.12 (s, 1H), 6.91 (d, J=8.7 Hz, 1H), 5.22 (d, J=15.4 Hz, 1H), 5.13 (d, J=10.3 Hz, 1H), 4.22 (d, J=15.5 Hz, 1H), 3.81 (s, 3H), 3.41-

3.32 (m, 1H), 2.99-2.93 (m, 4H), 2.24-2.20 (m, 1H), 2.16-2.11 (m, 2H), 1.82-1.75 (m, 1H), 1.31 (s, 9H), 1.02 (d, J=6.1 Hz, 3H).

Example 40

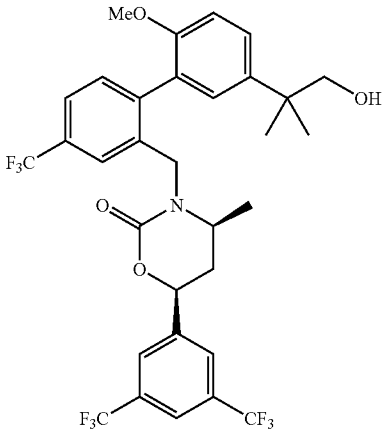

(4S,6S)-6-[3,5-bis(trifluoromethyl)phenyl]-3-{[5'-(2-hydroxy-1,1-dimethylethyl)-2'-methoxy-4-(trifluoromethyl)biphenyl-2-yl]methyl}-4-methyl-1,3-oxazinan-2-one (4S,6S)-6-[3,5-bis(trifluoromethyl)phenyl]-3-[2-iodo-5-trifluoromethyl)benzyl]-4-methyl-1,3-oxazinan-2-one (Intermediate 23; 30 mg; 0.049 mmol) was treated with 2-[4-methoxy-3-(4,4,5,5-tetramethyl-1,3,2-dioxaborolan-2-yl) phenyl]-2-methylpropan-1-ol (intermediate 26; 20 mg; 0.065 mmol), 1-1'-bis(di tert-butylphosphino)ferrocene palladium dichloride (3.2 mg; 0.0049 mmol), 1 N $K_2CO_3$ (1.2 mL) and THF (1.2 mL) as described in Example 38 to afford (4S,6S)-6-[3,5-bis(trifluoromethyl)phenyl]-3-{[5'-(2-hydroxy-1,1-dimethylethyl)-2'-methoxy-4-(trifluoromethyl)biphenyl-2-yl]methyl}-4-methyl-1,3-oxazinan-2-one as a clear glass. LCMS=664.0 $(M+1)^+$. $^1$H NMR ($CDCl_3$, 500 MHz, mixture of atropisomers): δ 7.86-7.80 (m, 2H), 7.76 (s, 1H), 7.67-7.61 (m, 2H), 7.41-7.37 (m, 2H), 7.21 (d, J=2.3 Hz, 1H), 6.96 (d, J=8.7 Hz, 1H), 5.38 (d, J=15.5 Hz, 1H), 4.95 (d, J=11 Hz, 1H), 4.09 (d, J=15.5 Hz, 1H), 3.81 (s, 3H), 3.65-3.63 (m, 1H), 3.58-3.55 (m, 1H), 3.41-3.35 (m, 1H), 2.25-2.20 (m, 1H), 1.80-1.72 (m, 1H), 1.28-1.25 (m, 6H), 1.07-1.03 (m, 3H).

Example 41

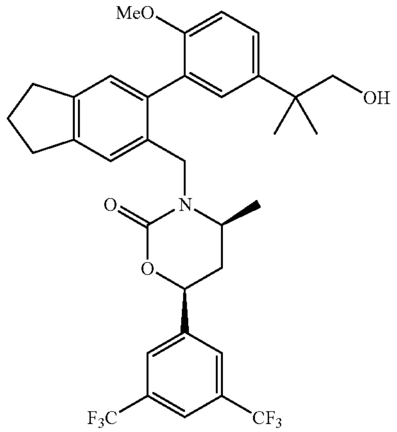 [SMILES: COc1ccc(C(C)(C)CO)cc1-c1cc2c(cc1CN1C(=O)O[C@H](c3cc(C(F)(F)F)cc(C(F)(F)F)c3)C[C@@H]1C)CCC2]

(4S,6S)-6-[3,5-bis(trifluoromethyl)phenyl]-3-({6-[5-(2-hydroxy-1,1-dimethylethyl)-2-methoxyphenyl]-2,3-dihydro-1H-inden-5-yl}methyl)-4-methyl-1,3-oxazinan-2-one (4S,6S)-6-[3,5-bis(trifluoromethyl)phenyl]-3-[(6-iodo-2,3-dihydro-1H-inden-5-yl)methyl]-4-methyl-1,3-oxazinan-2-one (Intermediate 25; 30 mg; 0.052 mmol) was treated with 2-[4-methoxy-3-(4,4,5,5-tetramethyl-1,3,2-dioxaborolan-2-yl)phenyl]-2-methylpropan-1-ol (Intermediate 26; 20 mg; 0.067 mmol), 1-1'-bis(di tert-butylphosphino)ferrocene palladium dichloride (3.4 mg; 0.0052 mmol), 1 N $K_2CO_3$ (1.2mL) and THF (1.2 mL) as described in Example 38 to afford (4S,6S)-6-[3,5-bis(trifluoromethyl)phenyl]-3-({6-[5-(2-hydroxy-1,1-dimethylethyl)-2-methoxyphenyl]-2,3-dihydro-1H-inden-5-yl}methyl)-4-methyl-1,3-oxazinan-2-one as a clear glass. LCMS=636.1 $(M+1)^+$. $^1$H NMR ($CDCl_3$, 500 MHz, mixture of atropisomers): δ 7.84-7.79 (m, 2H), 7.75 (s, 1H), 7.33 (dd, J=8.7, 2.5 Hz, 1H), 7.29 (s, 1H), 7.23 (d, J=2.3 Hz, 1H), 7.13 (s, 1H), 6.95-6.92 (m, 1H), 5.41 (d, J=15.3 Hz, 1H), 4.93 (d, J=10.5 Hz, 1H), 3.93 (d, J=15.4 Hz, 1H), 3.81 (s, 3H), 3.65-3.61 (m, 1H), 3.57-3.54 (m, 1H), 3.44-3.36 (m, 1H), 2.99-2.94 (m, 4H), 2.20-2.10 (m, 3H), 1.76-1.64 (m, 1H), 1.33-1.25 (m, 6H), 1.05-1.02 (m, 3H).

Example 42

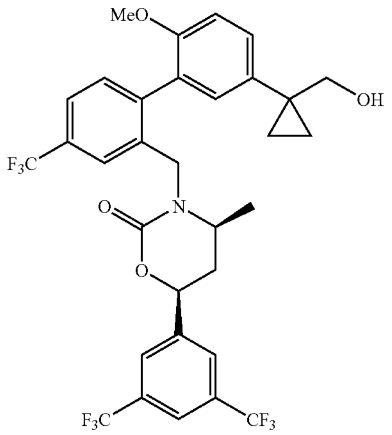 [SMILES: COc1ccc(C2(CO)CC2)cc1-c1ccc(C(F)(F)F)cc1CN1C(=O)O[C@H](c2cc(C(F)(F)F)cc(C(F)(F)F)c2)C[C@@H]1C]

(4S,6S)-6-[3,5-bis(trifluoromethyl)phenyl]-3-{[5'-[1-(hydroxymethyl)cyclopropyl]-2'-methoxy-4-(trifluoromethyl)biphenyl-2-yl]methyl}-4-methyl-1,3-oxazinan-2-one (4S,6S)-6-[3,5-bis(trifluoromethyl)phenyl]-3-[2-iodo-5-(trifluoromethyl)benzyl]-4-methyl-1,3-oxazinan-2-one (Intermediate 23; 28 mg; 0.046 mmol) was treated with {1-[4-methoxy-3-(4,4,5,5-tetramethyl-1,3,2-dioxaborolan-2-yl)phenyl]cyclopropyl}methanol (Intermediate 28; 18 mg; 0.060 mmol), 1-1'-bis(di tert-butylphosphino) ferrocene palladium dichloride (3.0 mg; 0.0046 mmol), 1 N $K_2CO_3$ (2 mL) and THF (2 mL) as described in Example 38 to afford (4S,6S)-6-[3,5-bis(trifluoromethyl)phenyl]-3-{[5'-[1-(hydroxymethyl)cyclopropyl]-2'-methoxy-4-(trifluoromethyl)biphenyl-2-yl]methyl}-4-methyl-1,3-oxazinan-2-one as a white solid. LCMS=662.0 $(M+1)^+$. $^1$H NMR ($CDCl_3$, 500 MHz, mixture of atropisomers): δ 7.86-7.82 (m, 2H), 7.76 (s, 1H), 7.66-7.61 (m, 2H), 7.40-7.37 (m, 1H), 7.27-7.24 (m, 2H), 6.96-6.93 (m, 1H), 5.40 (d, J=15.6 Hz, 1H), 4.91 (d, J=10.5 Hz, 1H), 4.11 (d, J=15.6 Hz, 1H), 3.91 (s, 3H), 3.68-3.56 (m, 2H), 3.39-3.32 (m, 1H), 2.24-2.16 (m, 1H), 1.80-1.64 (m, 1H), 1.05 (d, J=6.2 Hz, 3H), 0.88-0.74 (m, 4H).

Example 43

The compound below was prepared by methods analogous to those described in Examples 11-12. LC/MS (M+1) is 633.9.

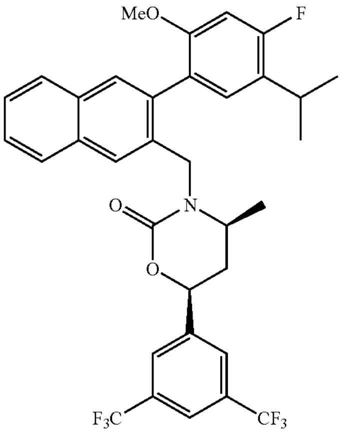 [SMILES: COc1cc(F)c(C(C)C)cc1-c1cc2ccccc2cc1CN1C(=O)O[C@H](c2cc(C(F)(F)F)cc(C(F)(F)F)c2)C[C@@H]1C]

Example 44

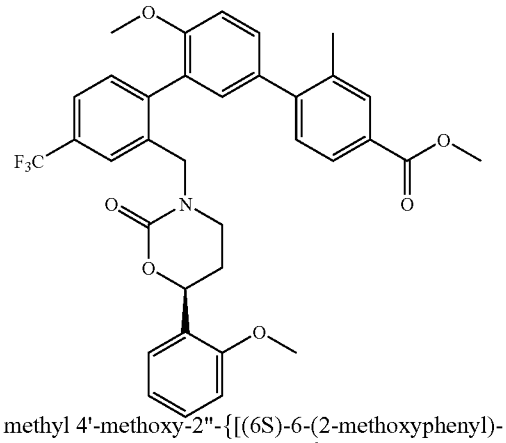

methyl 4'-methoxy-2"-{[(6S)-6-(2-methoxyphenyl)-2-oxo-1,3-oxazinan-3-yl]methyl}-2-methyl-4"-(trifluoromethyl)-1,1':3',1"-terphenyl-4-carboxylate To a solution of (6S)-6-(2-methoxyphenyl)-1,3-oxazinan-2-one (31.6 mg, 0.152 mmol) in DMF (1.5 mL) was added t-BuOK (16.5 mg, 0.144 mmol). The reaction was stirred for 15 minutes, then a solution of 2"-(bromomethyl)-4'-methoxy-2-methyl-4"-(trifluoromethyl)-1,1':3',1"-terphenyl-4-carboxylate (75 mg, 0.152 mmol) in DMF (15 mL) was added via cannula. The reaction was stirred at room temperature for 1 hour, and then quenched with saturated $NH_4Cl$ solution (10 mL), diluted with EtOAc (20 mL), washed with brine (10 mL), dried over $Na_2SO_4$, filtered, and concentrated. The residue was purified by silica gel chromatography (10 to 50% EtOAc/hexanes) to afford methyl 4'-methoxy-2"-{[(6S)-6-(2-methoxyphenyl)-2-oxo-1,3-oxazinan-3-yl]methyl}-2-methyl-4"-(trifluoromethyl)-1,1':3',1"-terphenyl-4-carboxylate LCMS=619.8 $(M+1)^+$. $^1$H NMR ($CDCl_3$, 500 MHz, rotamers present) δ 7.78-7.94 (m, 2H), 7.68 (s, 1H), 7.60 (t, J=9.0 Hz, 1H), 7.25-7.44 (m, 5H), 6.79-7.15 (m, 4H), 5.58 (dd, J=9.2, 2.5 Hz), 5.32 (dd, J=9.2, 2.5 Hz), 4.76 (d, J=15.3 Hz, 1H), 4.57 (d, J=15.3 Hz), 4.48 (d, J=15.6 Hz), 3.92 (s, 3H), 3.86 (s), 3.84 (s), 3.80 (s), 3.65 (s), 2.88-3.16 (m, 2H), 2.35 (s), 2.32 (s), 1.85-2.20 (m, 2H).

In a similar manner, the following compound was synthesized:

| Compound | Molecular structure | LCMS $(M + 1)^+$ |
|---|---|---|
| 45 | 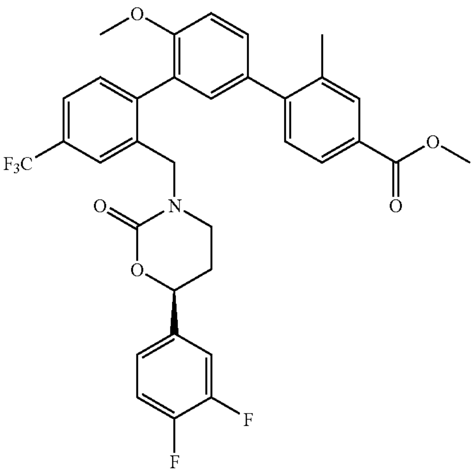 [SMILES: COC(=O)c1ccc(-c2ccc(OC)c(-c3ccc(C(F)(F)F)cc3CN3CC[C@@H](c4ccc(F)c(F)c4)OC3=O)c2)c(C)c1] | 626.1 |

Example 46

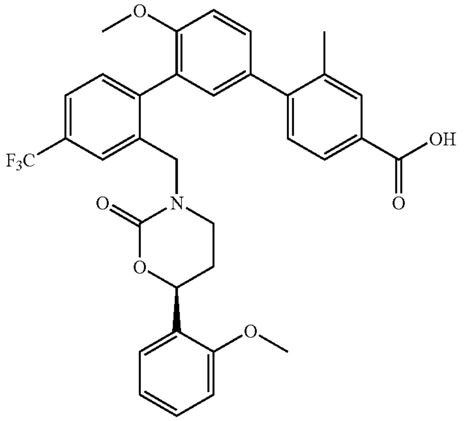 [SMILES: COc1ccc(-c2ccc(C(=O)O)cc2C)cc1-c1ccc(C(F)(F)F)cc1CN1CC[C@@H](c2ccccc2OC)OC1=O]

4'-methoxy-2"-{[(6S)-6-(2-methoxyphenyl)-2-oxo-1,3-oxazinan-3-yl]methyl}-2-methyl-4"-(trifluoromethyl)-1,1':3',1"-terphenyl-4-carboxylic acid To a solution of methyl 4'-methoxy-2"-{[(6S)-6-(2-methoxyphenyl)-2-oxo-1,3-oxazinan-3-yl]methyl}-2-methyl-4"-(trifluoromethyl)-1,1':3',1"-terphenyl-4-carboxylate (55.4 mg, 0.0358 mmol) in MeOH (1.5 mL) was added 4 M KOH solution (0.8 mL). The reaction was stirred at room temperature for 6 hours, and then quenched with 1 N HCl (5 mL) and diluted with EtOAc (15 mL). The aqueous layer was extracted with EtOAc (10 mL), and the combined organic extracts were washed with brine (10 mL), dried over $Na_2SO_4$, filtered, and concentrated. The residue was purified by reverse-phase chromatography (C-18, 10 to 95% MeCN/water with 0.1% TFA) to afford 4'-methoxy-2"-{[(6S)-6-(2-methoxyphenyl)-2-oxo-1,3-oxazinan-3-yl]methyl}-2-methyl-4"-(trifluoromethyl)-1,1':3',1"-terphenyl-4-carboxylic acid. LCMS=606.0 $(M+1)^+$. $^1H$ NMR ($CDCl_3$, 500 MHz, rotamers present) δ 7.84-8.01 (m, 2H), 7.60-7.67 (m, 2H), 7.26-7.42 (m, 5H), 6.79-7.16 (m, 4H), 5.58 (dd, J=9.3, 2.7 Hz), 5.27 (dd, J=9.4, 2.6 Hz), 4.84 (d, J=14.9 Hz), 4.77 (d, J=15.6 Hz), 4.48-4.54 (m, 1H), 3.87 (s), 3.85 (s), 3.81 (s), 3.64 (s), 2.86-3.20 (m, 2H), 2.38 (s), 2.33 (s), 1.80-2.24 (m, 2H).

In a similar manner, the following compound was synthesized:

| Compound | Molecular structure | LCMS $(M + 1)^+$ |
|---|---|---|
| 47 | 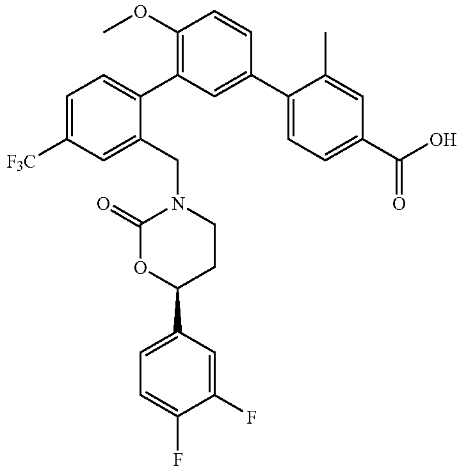 [SMILES: COc1ccc(-c2ccc(C(=O)O)cc2C)cc1-c1ccc(C(F)(F)F)cc1CN1CC[C@@H](c2ccc(F)c(F)c2)OC1=O] | 611.9 |

Example 48

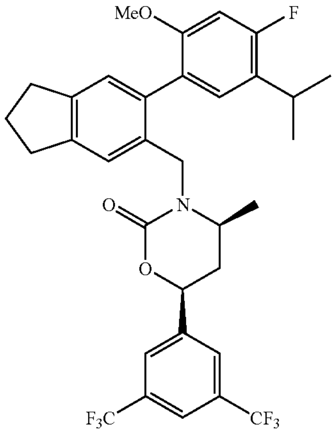 [SMILES: COc1cc(F)c(C(C)C)cc1-c1cc2c(cc1CN1C(=O)O[C@H](c3cc(C(F)(F)F)cc(C(F)(F)F)c3)C[C@@H]1C)CCC2]

(4S,6S)-6-[3,5-bis(trifluoromethyl)phenyl]-3-{[6-5-isopropyl-2-methoxyphenyl)-2,3-dihydro-1H-inden-5-yl]methyl}-4-methyl-1,3-oxazinan-2-one A mixture of (4S,6S)-6-[3,5-bis(trifluoromethyl)phenyl]-3-[(6-iodo-2,3-dihydro-1H-inden-5-yl)methyl]-4-methyl-1,3-oxazinan-2-one (8 mg; 0.014 mmol), (4-fluoro-5-isopropyl-2-methoxyphenyl)boronic acid (4 mg; 0.018 mmol) and 1-1'-bis(di tert-butylphosphino)ferrocene palladium dichloride (1.0 mg; 0.0014 mmol) in 1:1 1N $K_2CO_3$/THF (1.4 mL) was degassed three times and heated at 80° C. for 2 h. The reaction was diluted with water (10 mL) and extracted with EtOAc (3×10 mL). The combined extracts were washed with brine (10 mL), dried ($Na_7SO_4$), filtered and concentrated in vacuo. The residue was purified by flash silica gel chromatography (0-30% EtOAc/hexanes gradient) to afford (4S,6S)-6-[3,5-bis(trifluoromethyl)phenyl]-3-{[6-5-isopropyl-2-methoxyphenyl)-2,3-dihydro-1H-inden-5-yl]methyl}-4-methyl-1,3-oxazinan-2-one as a colorless glass.). LCMS=623.8 $(M+1)^+$. $^1H$ NMR ($CDCl_3$, 500 MHz, mixture of atropisomers) δ 7.84 (s, 2H), 7.76 (s, 1H), 7.29 (s, 1H), 7.08-7.01 (m, 2H), 6.66 (d, J=5.0 Hz, 1H), 5.22 (d, J=15.8 Hz, 1H), 4.68 (d, J=10.5 Hz, 1H), 4.21 (d, J=15.8 Hz, 1H), 3.78 (s, 3H), 3.44-3.34 (m, 1H), 3.24-3.16 (m, 1H), 2.98-2.92 (m, 4H), 2.27-2.22 (m, 1H), 2.14-2.09 (m, 2H) 1.86-1.78 (m, 1H), 1.27-1.19 (m, 6H), 1.03 (d, J=6.1 Hz, 3H).

Example 49

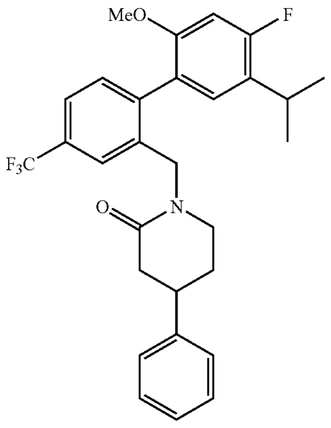 [SMILES: COc1cc(F)c(C(C)C)cc1-c1ccc(C(F)(F)F)cc1CN1CCC(c2ccccc2)CC1=O]

1-{[4'-fluoro-5'-isopropyl-2'-methoxy-4-(trifluoromethyl)biphenyl-2-yl]methyl}-4-phenylpiperidin-2-one 4-phenyl-piperidin-2-one (28.6 mg; 0.163 mmol) was treated with sodium hydride (60% in oil; 14 mg; 0.359 mmol) and 2-(bromomethyl)-4-fluoro-5-isopropyl-2-methoxy-4'-(trifluoromethyl)biphenyl (63 mg; 0.156 mmol) as described previously to afford 1-{[4'-fluoro-5'-isopropyl-2'-methoxy-4-(trifluoromethyl)biphenyl-2-yl]methyl}4-phenylpiperidin-2-one as a colorless glass. LCMS=499.9 $(M+1)^+$. $^1H$ NMR ($CDCl_3$, 500 MHz, mixture of atropisomers) δ 7.57-7.53 (m, 2H), 7.35-7.29 (m, 3H), 7.27-7.22 (m, 1H), 7.19-7.15 (m, 2H), 6.96 (d, J=8.7 Hz, 1H), 6.66 (d, J=12.1 Hz, 1H), 4.74 (d, J=15.3 Hz, 1H), 4.39 (d, J=15.1 Hz, 1H), 3.75 (s, 3H), 3.24-3.18 (m, 1H), 3.12-2.96 (m, 3H), 2.79-2.69 (m, 1H), 2.59-2.48 (m, 1H), 2.04-2.99 (m, 1H) 1.88-1.80 (m, 1H), 1.27-1.20 (m, 6H).

The enantiomers were separated on chiral HPLC (ChiralPak IA column, 5% IPA/heptane) to afford (4S)-1-{[4'-fluoro-5'-isopropyl-2'-methoxy-4-(trifluoromethyl)biphenyl-2-yl]-methyl}-4-phenylpiperidin-2-one and (4R)-1-{[4'-fluoro-5'-isopropyl-2'-methoxy-4-(trifluoromethyl)biphenyl-2-yl]methyl}-4-phenylpiperidin-2-one.

Example 50

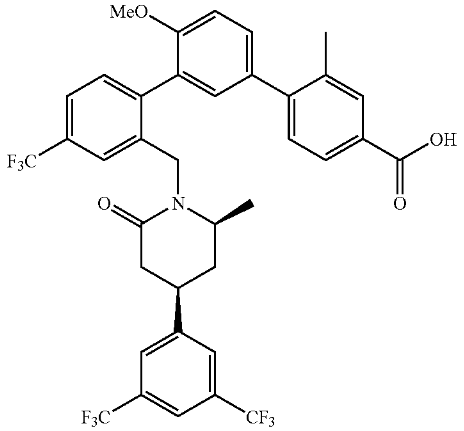 [SMILES: COc1ccc(-c2ccc(C(=O)O)cc2C)cc1-c1ccc(C(F)(F)F)cc1CN1C(=O)C[C@H](c2cc(C(F)(F)F)cc(C(F)(F)F)c2)C[C@@H]1C]

2''-({(4S,6S)-6-[3,5-bis(trifluoromethyl)phenyl]-4-methyl-2-oxo-1,3-oxazinan-3-yl}methyl)-4'-methoxy-2-methyl-4''-(trifluoromethyl)-1,1':3',1''-terphenyl-4-carboxylic acid Step A: Methyl 2''-({(4S,6S)-6-[3,5-bis(trifluoromethyl)phenyl]-4-methyl-2-oxo-1,3-oxazinan-3-yl}methyl)-4'-methoxy-2-methyl-4''-(trifluoromethyl)-1,1':3',1''-terphenyl-4-carboxylate To a stirred solution of methyl 2''-(bromomethyl)-4'-methoxy-2-methyl-4''-(trifluoromethyl)-1,1':3',1''-terphenyl-4-carboxylate (78.5 mg; 0.159 mmol) and (4S,6S)-6-[3,5-bis(trifluoromethyl)phenyl]-4-methyl-1,3-oxazinan-2-one (43.4 mg; 0-133 mmol) in DMF (1 mL) was added potassium tert-butoxide (14.9 mg; 0.133 mmol). The reaction was stirred at room temperature for 2 h, quenched with sat. $NH_4Cl$, and partitioned between EtOAc (10 mL) and sat. $NH_4Cl$ (10 mL). The aqueous layer was extracted with EtOAc (4×25 mL) and the combined extracts were washed with brine, dried ($MgSO_4$), filtered and concentrated in vacuo. The residue was purified by flash silica gel chromatography (0-100% EtOAc/hexanes gradient) to afford methyl 2''-({(4S,6S)-6-[3,5-bis(trifluoromethyl)phenyl]-4-methyl-2-oxo-1,3-oxazinan-3-yl}methyl)-4'-methoxy-2-methyl-4''-(trifluoromethyl)-1,1':3',1''-terphenyl-4-carboxylate as a colorless glass. LCMS=740.0 $(M+1)^+$. $^1H$ NMR ($CDCl_3$, 500 MHz, mixture of atropisomers) δ 7.89-7.82 (m, 3H), 7.71-7.66 (m, 2H), 7.59 (s, 1H), 7.43 (d, J=8.5 Hz, 1H), 7.41-7.38 (m, 1H), 7.30 (d, J=8 Hz, 1H), 7.22 (d, J=2.2 Hz, 1H), 7.16 (d, J=8 Hz, 1H) 7.11-7.07 (m, 1H), 5.38 (d, J=15.6 Hz, 1H), 4.65 (d, J=11.5 Hz, 1H), 4.32 (d, J=15.8 Hz, 1H), 3.93 (s, 3H), 3.92 (s, 3H), 3.30-3.25 (m, 1H), 2.34 (s, 3H), 2.17-2.12 (m, 1H), 1.73-1.65 (m, 1H), 1.08 (d, J=6.2 Hz, 3).

Step B: 2"-({(4S,6S)-6-[3,5-bis(trifluoromethyl)-phenyl]-4-methyl-2-oxo-1,3-oxazinan-3-yl}methyl)-4'-methoxy-2-methyl-4"-(trifluoromethyl)-1,1':3',1"-terphenyl-4-carboxylic acid To a stirred solution of methyl 2"-({(4S,6S)-6-[3,5-bis(trifluoromethyl)phenyl]-4-methyl-2-oxo-1,3-oxazinan-3-yl}methyl)-4'-methoxy-2-methyl-4"-(trifluoromethyl)-1,1':3',1"-terphenyl-4-carboxylate (Step A; 48 mg; 0.065 mmol) in MeOH (5 mL), was added 4 M KOH (800 μL). The reaction was stirred at room temperature for 4 h, quenched with saturated citric acid and partitioned between EtOAc (25 mL) and water (25 mL). The aqueous layer was extracted with EtOAc (3×25 mL) and the combined extracts were washed with brine, dried ($MgSO_4$), filtered and concentrated in vacuo. The residue was purified by preparatory thin layer chromatography, eluting with 2:1 hexanes:EtOAc+1% AcOH to afford 2"-({(4S,6S)-6-[3,5-bis(trifluoromethyl)phenyl]-4-methyl-2-oxo-1,3-oxazinan-3-yl}methyl)-4'-methoxy-2-methyl-4"-(trifluoromethyl)-1,1':3',1"-terphenyl-4-carboxylic acid as a white solid. LCMS=725.9 $(M+1)^+$. $^1H$ NMR ($CDCl_3$, 500 MHz, mixture of atropisomers) δ 7.97-7.94 (m, 1H), 7.86-7.82 (m, 2H), 7.78 (d, J=8 Hz, 1H), 7.68-7.66 (m, 1H), 7.63-7.61 (m, 1H), 7.45-7.39 (m, 2H), 7.34 (d, J=8 Hz, 1H), 7.25-7.20 (m, 2H), 7.12-7.09 (m, 1H), 5.37 (d, J=15.5 Hz, 1H), 4.67 (d, J=11.4 Hz, 1H), 4.34 (d, J=15.6 Hz, 1H), 3.91 (s, 3H), 3.32-3.26 (m, 1H), 2.36 (s, 3H), 2.19-2.13 (m, 1H), 1.75-1.67 (m, 1H), 1.09 (d, J=6.1 Hz, 3H).

What is claimed is:

1. A compound of formula Ia, or a pharmaceutically acceptable salt thereof,

Ia

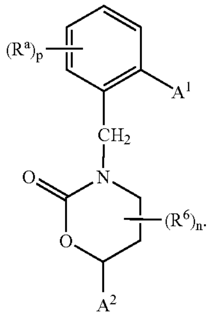

wherein the phenyl ring may optionally have —N═ in place of the —(CH)═ at the unsubstituted position that is ortho to the methylene group in formula Ia;

$A^1$ is phenyl, which is optionally substituted with 1-3 substituents independently selected from (a) halogen, (b) $C_{1-5}$alkyl optionally substituted with 1-5 halogens and optionally 1 group —OH, (c) —$OC_{1-3}$alkyl optionally substituted with 1-3 halogens, (d) $C_{2-4}$alkenyl optionally substituted with 1-3 halogens, and (e) optionally one group selected from phenyl and C3-6cycloalkyl, said phenyl and cycloalkyl being optionally substituted with 1-3 substituents independently selected from halogen, —$CO_2H$, —$CO_2C_{1-3}$alkyl optionally substituted with 1-3 halogens, $C_{1-3}$alkyl optionally substituted with 1-3 halogens and optionally one —OH, and —$OC_{1-3}$alkyl optionally substituted with 1-3 halogens;

$A^2$ is phenyl optionally substituted with 1-3 groups independently selected from halogen, $C_{1-3}$alkyl optionally substituted with 1-3 halogens, —$OCH_3$ and —$OCF_3$;

each $R^a$ is independently selected from the group consisting of halogen, $C_{1-4}$-alkyl optionally substituted with 1-3 halogens, $C_{2-3}$alkenyl optionally substituted with 1-3 halogens, —$OCH_3$, and —$OCF_3$, wherein two $R^a$ groups on adjacent carbon atoms of the phenyl ring optionally may be joined to form a bridging moiety selected from —$CH_2CH_2CH_2$—, —$CH_2CH_2CH_2CH_2$—, and —CH═CH—CH═CH—, thereby yielding a cyclopentyl, cyclohexyl, or phenyl ring fused to the phenyl ring, said cyclopentyl, cyclohexyl, and phenyl ring being optionally substituted with 1-2 groups independently selected from halogen, $CH_3$, $CF_3$, —$OCH_3$, and —$OCF_3$;

$R^6$ is $C_{1-3}$alkyl optionally substituted with 1-3 halogens;

p is an integer from 1-3; and n is an integer from 0-2.

2. The compound of claim 1, which is selected from the group consisting of the following compounds, or a pharmaceutically acceptable salt thereof:

Ex. 1

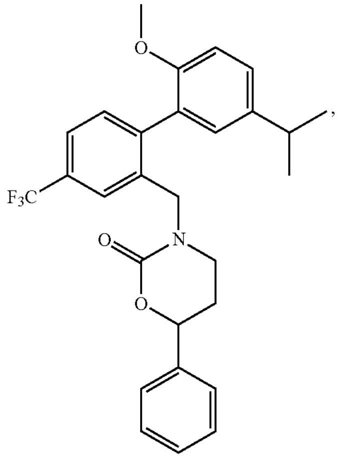

Ex. 2

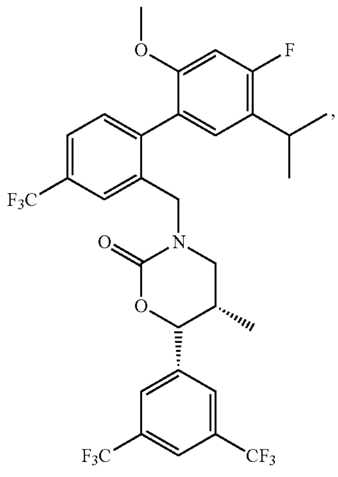

-continued
Ex. 3
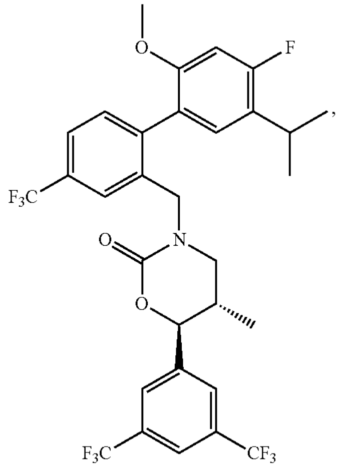
Ex. 4
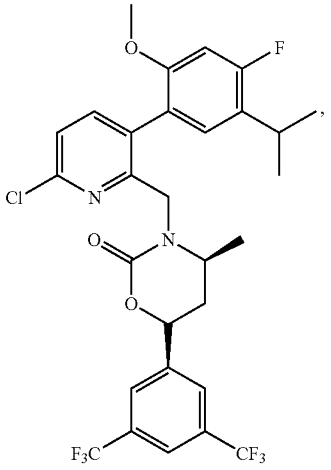
Ex. 5
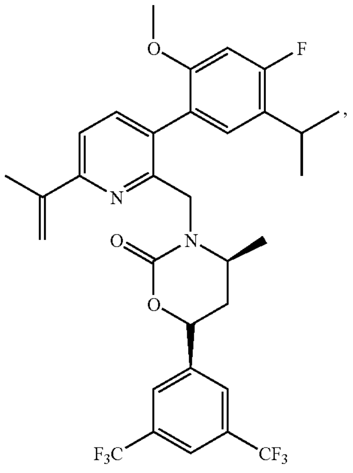
-continued
Ex. 6
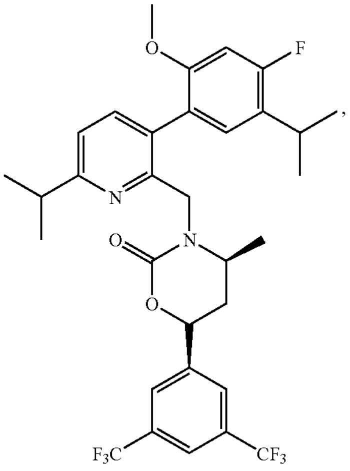
Ex. 7
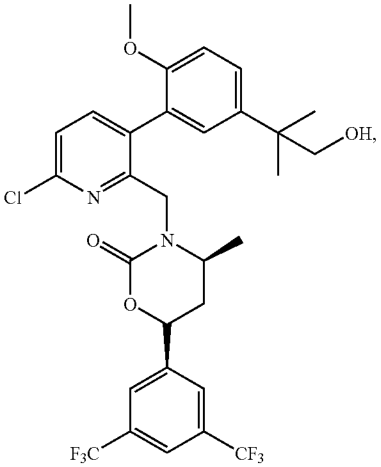
Ex. 10
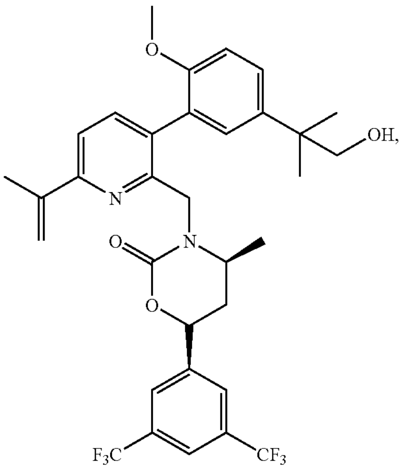

-continued
Ex. 11
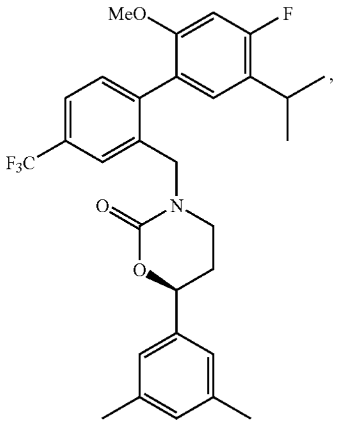
Ex. 12
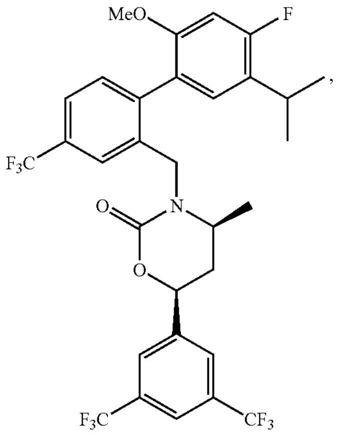
Ex. 36
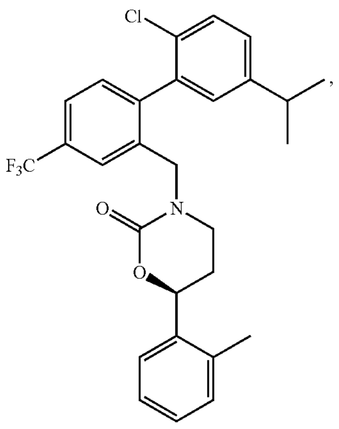
-continued
Ex. 37
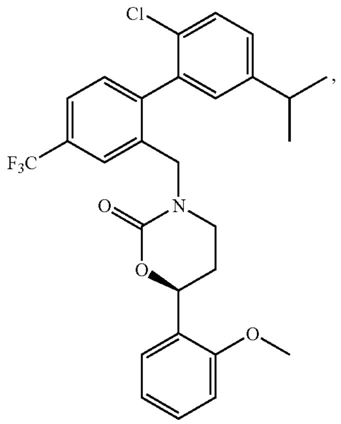
Ex. 38
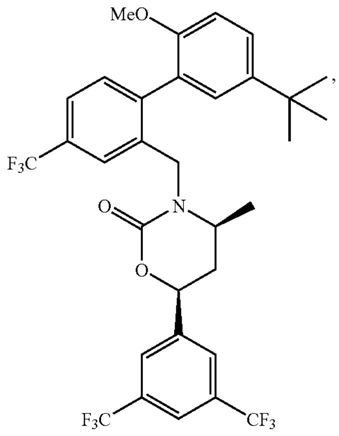
Ex. 39
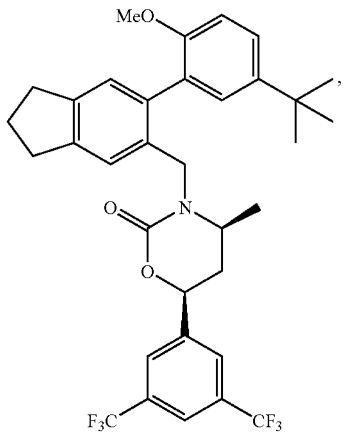

-continued
Ex. 40
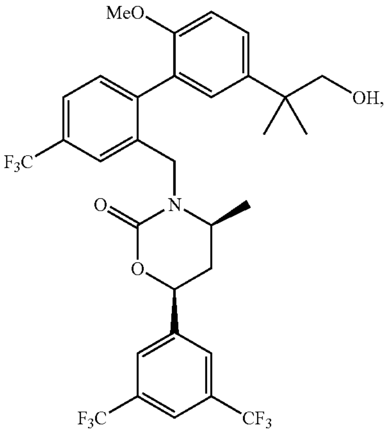
Ex. 41
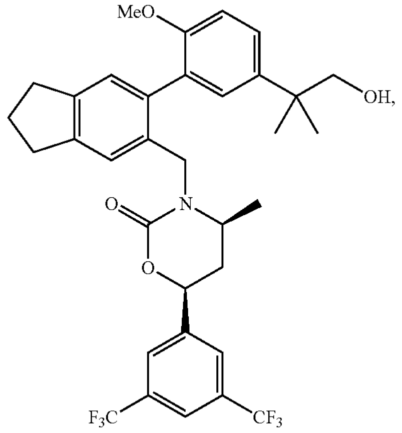
Ex. 42
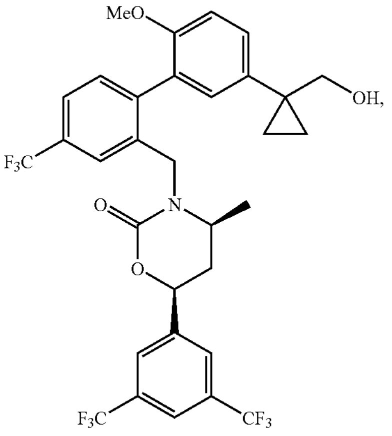
-continued
Ex. 43
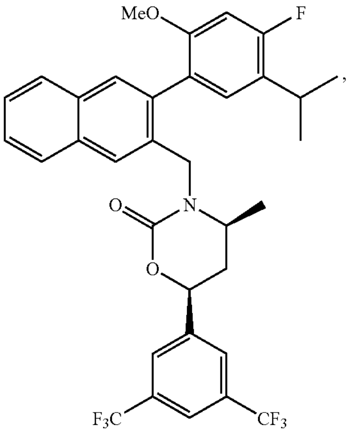
Ex. 44
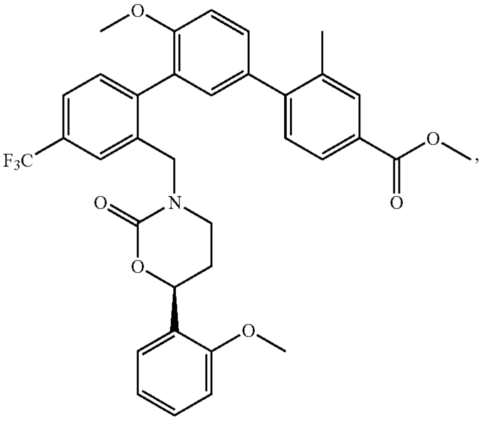
Ex. 45
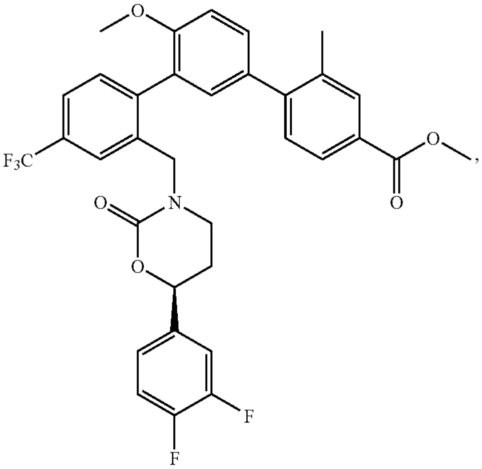

-continued
Ex. 46
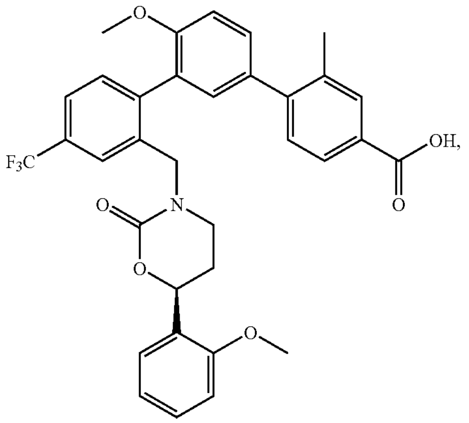
Ex. 47
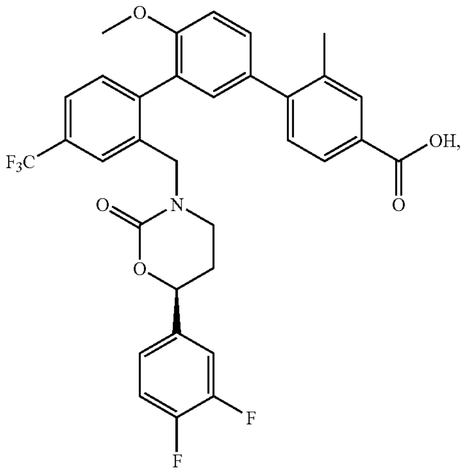
Ex. 48
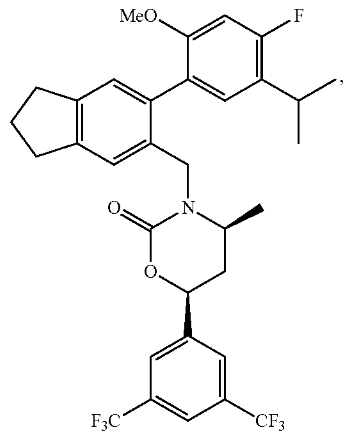
-continued
Ex. 50
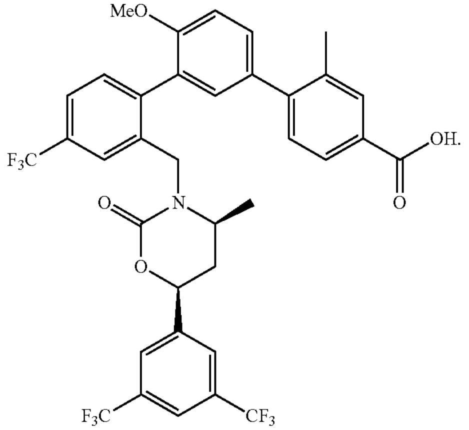
3. The compound of claim 1, which is selected from the following compounds, or a pharmaceutically acceptable salt thereof:
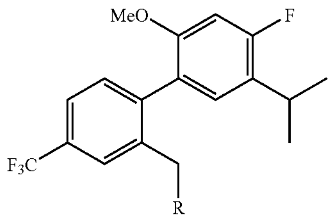
wherein R is selected from the group consisting of:
Ex. 13
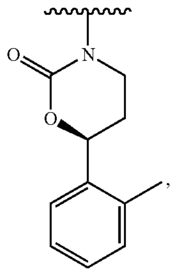
Ex. 14
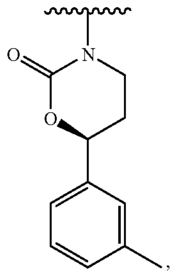
Ex.15
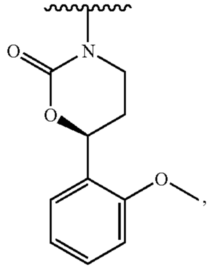

-continued
Ex. 16
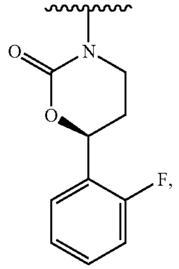
Ex. 17
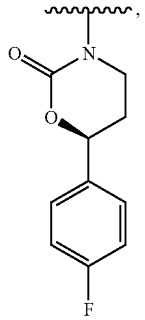
Ex. 18
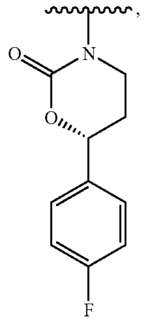
Ex. 19
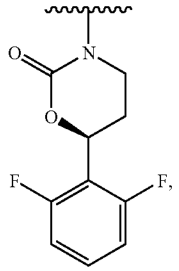
Ex. 20
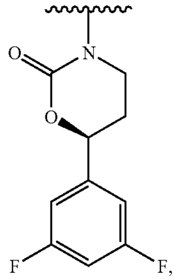
-continued
Ex. 21
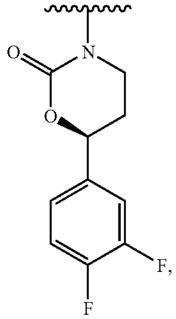
Ex. 22
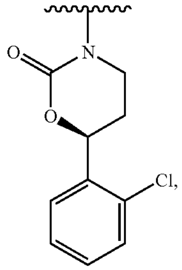
Ex. 23
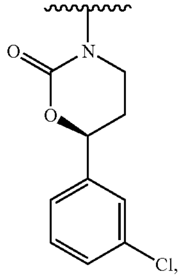
Ex. 24
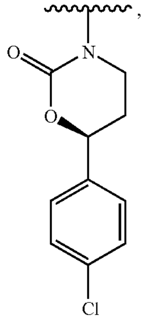
Ex. 25
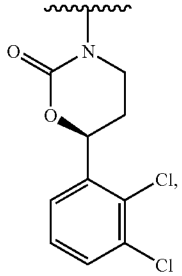

-continued

Ex. 26

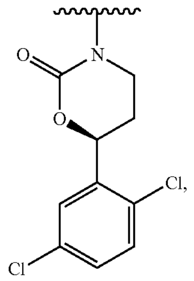

Ex. 27

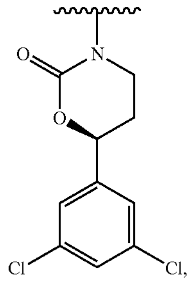

Ex. 28

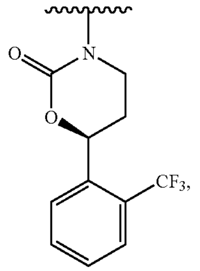

Ex. 29

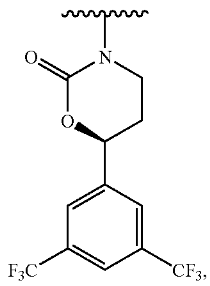

Ex. 30

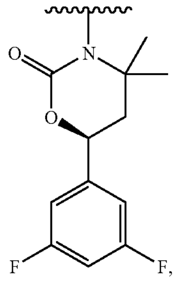

-continued

Ex. 31

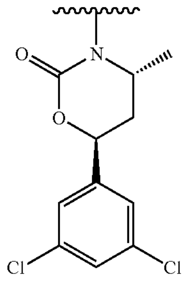

(racemic),

Ex. 32

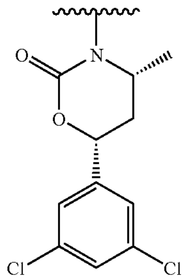

(racemic),

Ex. 33

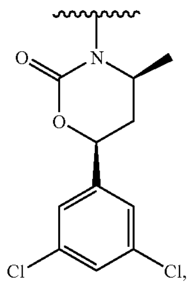

Ex. 34

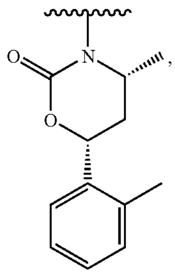

, and

Ex. 35

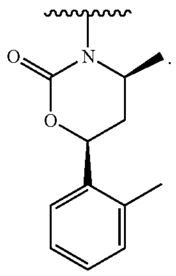

4. A method of treating atherosclerosis in a patient in need of treatment comprising the administration of a therapeutically effective amount of the compound of claim 1, or a pharmaceutically acceptable salt thereof, to said patient.

5. A method of raising HDL-C in a patient in need of treatment comprising the administration of a therapeutically effective amount of the compound of claim 1, or a pharmaceutically acceptable salt thereof, to said patient.

6. A method of lowering LDL-C in a patient in need of treatment comprising the administration of a therapeutically effective amount of the compound of claim 1, or a pharmaceutically acceptable salt thereof, to said patient.

7. A pharmaceutical composition comprising the compound of claim 1, or a pharmaceutically acceptable salt thereof, and a pharmaceutically acceptable carrier.

8. A pharmaceutical composition comprising the compound of claim 1, or a pharmaceutically acceptable salt thereof, and one or more active ingredients selected from the group consisting of:

(a) PPAR gamma agonists and partial agonists;

(b) biguanides;

(c) protein tyrosine phosphatase-1B (PTP-1B) inhibitors, (d) dipeptidyl peptidase IV (DP-IV) inhibitors;

(e) insulin or insulin mimetics;

(f) sulfonylureas;

(g) α-glucosidase inhibitors;

(h) one or more compounds selected from the group consisting of (a) HMG-CoA reductase inhibitors; (b) bile acid sequestrants; (c) niacin, nicotinyl alcohol, nicotinamide, and nicotinic acid or a salt thereof; (d) PPARα agonists; (e) cholesterol absorption inhibitors; (f) acyl CoA:cholesterol acyltransferase (ACAT) inhibitors; (g) phenolic anti-oxidants, such as probucol, and (h) a microsomal triglyceride transfer protein (MTP)/ApoB secretion inhibitor;

(i) PPAR α/γ dual agonists;

(j) PPAR δ agonists;

(k) antiobesity compounds (l) ileal bile acid transporter inhibitors;

(m) anti-inflammatory agents;

(n) glucagon receptor antagonists;

(o) GLP-1, (p) GIP-1, and (q) GLP-1 analogs.

* * * * *